US008715997B2

(12) United States Patent
Aehle et al.

(10) Patent No.: US 8,715,997 B2
(45) Date of Patent: May 6, 2014

(54) **VARIANT *HYPOCREA JECORINA* CBH2 CELLULASES**

(75) Inventors: Wolfgang Aehle, Leiden (NL); Frits Goedegebuur, Leiden (NL); Lydia Dankmeyer, Leiden (NL); Colin Mitchinson, Half Moon Bay, CA (US); Paulien Neefe, Leiden (NL); Bradley Kelemen, Menlo Park, CA (US); Robert Caldwell, Belmont, CA (US); Pauline Teunissen, Leiden (NL)

(73) Assignee: Danisco US Inc., Palo Alto, CA (US)

( * ) Notice: Subject to any disclaimer, the term of this patent is extended or adjusted under 35 U.S.C. 154(b) by 437 days.

(21) Appl. No.: 13/178,227

(22) Filed: Jul. 7, 2011

(65) Prior Publication Data

US 2012/0040435 A1 Feb. 16, 2012

Related U.S. Application Data

(62) Division of application No. 11/317,110, filed on Dec. 22, 2005, now Pat. No. 8,008,056.

(60) Provisional application No. 60/640,398, filed on Dec. 30, 2004, provisional application No. 60/656,863, filed on Feb. 25, 2005.

(51) Int. Cl.
*C12N 9/42* (2006.01)
*C12N 9/14* (2006.01)
*C12P 21/06* (2006.01)
*C12P 19/34* (2006.01)
*C12N 15/00* (2006.01)
*C12N 1/20* (2006.01)
*C12N 1/00* (2006.01)
*C07H 21/04* (2006.01)
*C07K 1/00* (2006.01)

(52) U.S. Cl.
USPC ......... 435/209; 435/195; 435/69.1; 435/91.1; 435/320.1; 435/252.3; 435/254.1; 536/23.1; 536/23.2; 530/350

(58) Field of Classification Search
USPC ......... 435/209, 195, 69.1, 91.1, 320.1, 252.3, 435/254.1; 536/23.1, 23.2; 530/350
See application file for complete search history.

(56) References Cited

U.S. PATENT DOCUMENTS

| 4,435,307 A | 3/1984 | Barbesgaard et al. |
| 4,822,516 A | 4/1989 | Suzuki et al. |
| 5,246,853 A | 9/1993 | Clarkson et al. |
| 5,275,944 A | 1/1994 | Himmel et al. |
| 5,475,101 A | 12/1995 | Ward et al. |
| 5,536,655 A | 7/1996 | Thomas et al. |
| 5,648,263 A | 7/1997 | Schulein et al. |
| 5,650,322 A | 7/1997 | Clarkson et al. |
| 5,691,178 A | 11/1997 | Schulein et al. |
| 5,776,757 A | 7/1998 | Schulein et al. |
| 5,861,271 A | 1/1999 | Fowler et al. |
| 6,114,158 A | 9/2000 | Li et al. |
| 6,162,782 A | 12/2000 | Clarkson et al. |
| 6,403,362 B1 | 6/2002 | Moriya et al. |
| 6,599,722 B2 | 7/2003 | Boston et al. |
| 7,452,707 B2 | 11/2008 | Goedegebuur et al. |
| 8,008,056 B2 | 8/2011 | Aehle et al. |

FOREIGN PATENT DOCUMENTS

| GB | 1368599 | 10/1974 |
| GB | 2094826 | 9/1982 |
| GB | 2095275 | 9/1982 |
| WO | WO 91/05039 | 4/1991 |
| WO | WO 92/06209 | 4/1992 |
| WO | WO 93/15188 | 8/1993 |
| WO | WO 94/28117 | 12/1994 |
| WO | WO 96/02551 | 2/1996 |
| WO | WO 98/14597 | 4/1998 |
| WO | WO 98/21339 | 5/1998 |
| WO | WO 99/01544 | 1/1999 |
| WO | WO 00/70031 | 11/2000 |
| WO | WO 01/96382 | 12/2001 |
| WO | WO 2004/056981 | 7/2004 |

OTHER PUBLICATIONS

Aro et al., J. Biol. Chem., vol. 276, No. 26, pp. 24309-24314, Jun. 29, 2001.
Altschul, et al., *J. Mol. Biol.* 215:403-410 (1990).
Aleksenko and Clutterbuck, Molecular Microbiology 1996 19:565-574.
Aubert, J. P. et al., Academic Press, pp. 71-86, 1988.
Ausubel et al., eds., *Current Protocols in Molecular Biology* (1994)).
Baker et al, Appl Biochem Biotechnol 1998 Spring; 70-72():395-403.
Berges & Barreau, Curr. Genet. 19:359-365 (1991.
Bhikhabhai et al., J. Appl. Biochem. 6:336-345, 1984.
Blakeney, A.B. & Mutton, L.L. (1980) Journal of Science of Food and Agriculture, 31, 889.
Brumbauer, et al., Bioseparation 7:287-295, 1999.
Brigidi, DeRossi, Bertarini, Riccardi and Matteuzzi, 1990, FEMS Microbiol. Lett. 55: 135-138.
Bajar, Podila and Kolattukudy, 1991, Proc. Natl. Acad. Sci. USA 88: 8202-8212.
Burley, et al., Science 229:23-29 (1985.
Cadwell et al., PCR Methods and Applications, vol. 2, 28-33 (1992).
Campbell, E.I. et al., Curr. Genet. 16:53-56, 1989.
Carter et al. Nucleic Acids Res. 13:4431-4443 (1985).
Coughlan, et al., "Comparative Biochemistry of Fungal and Bacterial Cellulolytic Enzyme Systems" Biochemistry and Genetics of Cellulose Degradation, pp. 11-30 1988.
Cummings and Fowler, Curr. Genet. 29:227-233, 1996).
Davies GJ, Brzozowski AM, Dauter M, Varrot A, Schulein M, Biochem J May 15, 2000;348 Pt 1 :201-7.

(Continued)

*Primary Examiner* — Ganapathirama Raghu
(74) *Attorney, Agent, or Firm* — Danisco US Inc.

(57) ABSTRACT

Described herein are variants of *H. jecorina* CBH2, a Cel6A enzyme. The present invention provides novel cellobiohydrolases that have altered thermostability.

43 Claims, 19 Drawing Sheets

(56) References Cited

OTHER PUBLICATIONS

Database UniProt [Online] Oct. 1, 2002 Collins C.M. et al., "Cellobiohyrolase II (EC 3.2.1.91). Talaromyces emersonii." XP002616639, retrieved from ebi Database accession No. Q8NIB5, Jan. 13, 2011.
Database UniProt [Online] Watanabe M. "Cellobiohydrolase II Acremonium cellulolyticus", XP002616640, retrieved from ebi Database accession No. O93837, Jan. 12, 2011.
Database UniProt [Online] Chow C.-M., "Exoglucanase 3 ; EC=3.2.1.91 Agaricus bioporus (Common mushroom)", XP002616641, retrieved from ebi Database accession No. P49075, Jan. 12, 2011.
Database EMBL [Online] Feb. 6, 2001 Zhu L. "Trichoderma koningii cellobiohydrolase II (cbh2) gene, complete cds.", XP002616642, retrieved from EBI accession No. EMBL:AF315681, Database accession No. AF315681.
Database EMBL [Online] Jul. 29, 1995 Tempelaars, C.A. "cbhII=exocellobiohydrolase [Phanerochaete chrysosporium, ME446, Genomic/mRNA, 2239 nt].", XP002616643, retrieved from EBI accession No. EMBL:S76141, Database accession No. S76141.
Database EMBL [Online] Apr. 2, 2001 Zhao J.. "Lentinula edodes cellobiohydrolase (cbhII-1) mRNA, complete cds.", XP002616644, retrieved from EBI accession No. EMBL:AF244369, Database accession No. AF244369.
Deutscher, Methods in Enzymology, vol. 182, No. 57, pp. 779, 1990.
Ellouz et al., J. Chromatography 396:307-317, 1987.
Fliess et al., Eur. J. Appl. Microbiol. Biotechnol. 17:314-318, 1983.
Filho et al., Can. J. Microbiol. 42:1-5, 1996.
Freer, J. Biol. Chem. vol. 268, No. 13, pp. 9337-9342, 1993.
Goedegebuur et al, Curr. Genet (2002) 41: 89-98.
Goldman, VanMontagu and Herrera-Estrella, 1990, Curr. Genet. 17:169-174.
Goyal et al., Bioresource Technol. 36:37-50, 1991.
Guo et al., "Protein Tolerance to Random Amino Acid Change," PNAS (2004) 101 pp. 9205-9210.
Halldorsdottir S et al., Appl Microbiol Biotechnol. 49(3):277-84, 1998.
Henikoff & Henikoff, *Proc. Natl. Acad. Sci. USA* 89:10915 (1989.
Henry, R.J. (1984) Journal of the Institute of Brewing, 90, 37.
Hu et al., Mol Cell Biol. vol. 11, No. 11, pp. 5792-5799, 1991.
Ilmen, M. et al., Appl. Environ. Microbiol. 63:1298-1306, 1997.
International Search Report PCT/US05/047266 dated Jul. 24, 2006.
Karlin & Altschul, *Proc. Nat'l. Acad. Sci. USA* 90:5873-5787 (1993).
Karlsson, J. et al. (2001), Eur. J. Biochem, 268, 6498-6507.
Kellis, et al., Nature 333:784-786 (1988)).
Kriegler, *Gene Transfer and Expression: A Laboratory Manual* (1990).
Kunkel et al., Proc. Natl. Acad.Sci.USA 82:488 (1987)).
Kumar et al., Textile Chemist and Colorist, 29:37-42, 1997.
Krishna et al., Bioresource Tech. 77:193-196, 2001.
Knowles et al., TIBTECH 5, 255-261, 1987.
Kuhls et al., PNAS (1996) 93:7755-7760.
Lever, M. (1972) Analytical Biochemistry, 47, 273).
Lorito, Hayes, DiPietro and Harman, 1993, Curr. Genet. 24: 349-356.
Li and Ljungdahl, Appl. Environ. Microbiol. 62, No. 1, pp. 209-213, 1996.
Linder and Teeri, J. Biotechnol. 57:15-28, 1997.
Lipman, *Proc. Nat'l Acad. Sci. USA* 85:2444,1988.
Matthews, et al., Proc. Natl. Acad. Sci. USA 84; 6663-6667 (1987).
Matthews, Ann. Rev. Biochem. 62:139-160 (1993).
Medve et al., J. Chromatography A 808:153-165, 1998.
Moriya et al., Bioscience Biotechnology Biochemistry, Japan Society for Bioscience, Biotechnology, and Agrochemistry (2003) 67:6 pp. 1434-1437.
Needleman, S. B. and Wunsch, C. D., (1970), Journal of Molecular Biology, 48, 443-45.
Ohmiya et al., Biotechnol. Gen. Engineer. Rev. vol. 14, pp. 365-414, 1997.
Ooi et al., Nucleic Acids Research, vol. 18, No. 19, 1990.
Penttila et al., Yeast vol. 3, pp. 175-185, 1987.
Penttila et al., Gene, 63: 103-112, (1988).
Penttila, Nevalainen, Ratto, Salminen and Knowles, 1987, Gene 6: 155-164.
Pere et al., In Proc. Tappi Pulping Conf., Nashville, TN, 27-31, pp. 693-696, 1996.
Rothstein et al., Gene 55:353-356, 1987.
Russel, et al., Current Opinions in Biotechnology 6:370-374 (1995)).
Sambrook, et al, 1989, Chapters 9 and 11, Current Protocols in Molecular Biology, John Wiley & Sons, New York, NY, 1993.
Schülein, Methods Enzymol., 160, 25, pp. 234-243, 1988.
Schomburg, D.; J. Reichelt, J. Mol. Graphics, 6:161-165 1988.
Scopes, Methods Enzymol. 90: 479-91, 1982.
Sheehan and Himmel *Biotechnology Progress 15*, pp. 817-827 (1999).
Sheir-Neiss, et al., Appl. Microbiol. Biotechnol. 20:46-53 (1984).
Shoemaker, S. et al., Bio/Technology, 1:691-696, 1983.
Singleton, et al., Dictionary of Microbiology and Molecular Biology, 2d Ed., John Wiley and Sons, New York (1994).
Smith & Waterman, *Adv. Appl. Math.* 2:482 (1981).
Stahlberg et al., Bio/Technol. 9:286-290, 1991.
Suurnakki, et al. Cellulose 7:189-209, 2000.
Tilbeurgh et al., FEBS Lett. 16:215, 1984.
Tomaz and Queiroz, J. Chromatography A 865:123-128, 1999.
Teeri, T. et al., Gene, 51:43-52, 1987.
Tomme et al., Eur. J. Biochem. 170:575-581, 1988.
Tormo et al., EMBO J. vol. 15, No. 21, pp. 5739-5751, 1996.
Teeri *Trends in Biotechnology 15*, pp. 160-167 (1997).
Teeri et al. Spec. Publ.—R. Soc. Chem., 246 (Recent Advances in Carbohydrate Bioengineering), pp. 302-308. (1999).
Tuohy Maria G. et al., "Kinetic Parameters and Mode of Actio of the Cellobiohydrolases Produced by Talaromyces emersonii," Biochimica et Biophysica Acta (2002) 1596:2 pp. 366-380.
UniProtKB/Swiss-Prot P07987 (GUX2_TRIRE) Jul. 24, 2007 Version 75 Exoglucanase 2 [Precursor] EC 3.2.1.91.
Vallette et al., Nuc. Acids Res. 17:723-733 (1989).
van Hartingsveldt et al., (1986) Development of a homologous transformation system for *Aspergillus niger* based on the *pyrG* gene. Mol. Gen. Genet. 206:71-75.
van Tilbeurgh et al., .FEBS Lett. 204:223-227, 1986.
Van Rensburg et al., Yeast, vol. 14, pp. 67-76, 1998.
Varrot A, Schulein M, Davies GJ, Biochemistry Jul. 13, 1999;38(28):8884-91.
Ward, M, Wilson, L.J. and Kodama, K.H., 1993, Appl. Microbiol. Biotechnol. 39:738-743.
Wells et al., Gene 34:315-323 (1985).
Wood, Biochemical Society Transactions, 611th Meeting, Galway, vol. 13, pp. 407-410, 1985.
Wood et al., Methods in Enzymology, vol. 160, No. 9, pp. 87-116, 1988.
Wood Biochem J. 121:353 (1971).
Wood, T. et al., Methods in Enzymology, vol. 160. (1988) pp. 19-25.
Zou, G.J. Kleywegt, J. Stahlberg, H. Drigues, W. Nerinckx, M. Claeyssens, A. Koivula, T.T. Teeri, T.A Jones, *Structure* (London), V. 7 p. 1035 (1999).
Zuber, Biophys. Chem. 29:171-179 (1988).

```
MIVGILTTLA TLATLAASVP LEERQACSSV WGQCGGQNWS GPTCCASGST
CVYSNDYYSQ CLPGAASSSS STRAASTTSR VSPTTSRSSS ATPPPGSTTT
RVPPVGSGTA TYSGNPFVGV TPWANAYYAS EVSSLAIPSL TGAMATAAAA
VAKVPSFMWL DTLDKTPLME QTLADIRTAN KNGGNYAGQF VVYDLPDRDC
AALASNGEYS IADGGVAKYK NYIDTIRQIV VEYSDIRTLL VIEPDSLANL
VTNLGTPKCA NAQSAYLECI NYAVTQLNLP NVAMYLDAGH AGWLGWPANQ
DPAAQLFANV YKNASSPRAL RGLATNVANY NGWNITSPPS YTQGNAVYNE
KLYIHAIGPL LANHGWSNAF FITDQGRSGK QPTGQQQWGD WCNVIGTGFG
IRPSANTGDS LLDSFVWVKP GGECDGTSDS SAPRFDSHCA LPDALQPAPQ
AGAWFQAYFV QLLTNANPSF L
```

Figure 1: *Hypocrea jecorina* (P07987 in Figure 3) CBH2 amino acid sequence.

```
atgattgtcg gcattctcac cacgctggct acgctggcca cactcgcagc tagtgtgcct   60
ctagaggagc ggcaagcttg ctcaagcgtc tggggccaat gtggtggcca gaattggtcg  120
ggtccgactt gctgtgcttc cggaagcaca tgcgtctact ccaacgacta ttactcccag  180
tgtcttcccg gcgctgcaag ctcaagctcg tccacgcgcg ccgcgtcgac gacttctcga  240
gtatccccca caacatcccg gtcgagctcc gcgacgcctc cacctggttc tactactacc  300
agagtacctc cagtcggatc gggaaccgct acgtattcag gcaacccttt tgttggggtc  360
actccttggg ccaatgcata ttacgcctct gaagttagca gcctcgctat tcctagcttg  420
actggagcca tggccactgc tgcagcagct gtcgcaaagg ttcctctttt tatgtggcta  480
gatactcttg acaagacccc tctcatggag caaaccttgg ccgacatccg caccgccaac  540
aagaatggcg gtaactatgc cggacagttt gtggtgtatg acttgccgga tcgcgattgc  600
gctgcccttg cctcgaatgg cgaatactct attgccgatg gtggcgtcgc caaatataag  660
aactatatcg acaccattcg tcaaattgtc gtggaatatt ccgatatccg gaccctcctg  720
gttattgagc ctgactctct tgccaacctg gtgaccaacc tcggtactcc aaagtgtgcc  780
aatgctcagt cagcctacct tgagtgcatc aactacgccg tcacacagct gaaccttcca  840
aatgttgcga tgtatttgga cgctggccat gcaggatggc ttggctggcc ggcaaaccaa  900
gacccggccg ctcagctatt tgcaaatgtt tacaagaatg catcgtctcc gagagctctt  960
cgcggattgg caaccaatgt cgccaactac aacggtgga acattaccag ccccccatcg 1020
tacacgcaag gcaacgctgt ctacaacgag aagctgtaca tccacgctat tggacctctt 1080
cttgccaatc acggctggtc caacgccttc ttcatcactg atcaaggtcg atcgggaaag 1140
cagcctaccg gacagcaaca gtggggagac tggtgcaatg tgatcggcac cggatttggt 1200
attcgcccat ccgcaaacac tgggactcg ttgctggatt cgtttgtctg ggtcaagcca 1260
ggcggcgagt gtgacggcac cagcgacagc agtgcgccac gatttgactc ccactgtgcg 1320
ctcccagatg ccttgcaacc ggcgcctcaa gctggtgctt ggttccaagc ctactttgtg 1380
cagcttctca aaacgcaaa cccatcgttc ctgtaa                            1416
```

Figure 2: cDNA sequence CBH2 (M16190)

Figure 3A

```
                   1                                                50
Q9C1S9     (1)   -MAKFFLTAAFAAAALAAPVVEERQNCAPTWGQCGGIGFNGPTCCQSGST
O93837     (1)   --------MLRYLSIVAATAILTGVEAQQSVWGQCGGQGWSGATSCAAGST
P49075     (1)   ------MFKFAALLALASLVPGFVQAQSPVWGQCGGNGWTGPTTCASGST
AF315681   (1)   MIVGILTTLATLATLAASVPLEERQACSSVWGQCGGQNWSGPTCCASGST
S76141     (1)   ------MKSTAFFAALVTLLPAYVAGQASEWGQCGGIGWTGPTTCVSGTT
Q8N1B5     (1)   --------MRNLLALAPAALLVGAAEAQQSLWGQCGGSSWTGATSCAAGAT
AF411251   (1)   -------MKITSTGLLALSSLLPFALGQSQLYAQCGGIGWSGATTCVSGAT
P07987     (1)   MIVGILTTLATLATLAASVPLEERQACSSVWGQCGGQNWSGPTCCASGST
Consensus  (1)        M L  LALAAASLLL   QAQSSVWGQCGGQGWSGPTTCASGST 51                                               100
Q9C1S9     (50)  CVKQNDWYSQCLPGSQVTTTSTTSTSSSSTTSRATSTTRTGGVTSITTAP
O93837     (44)  CSTLNPYYAQCIPGTATSTTLVKTTSSTSVG---------------TTSPPT
P49075     (45)  CVKQNDFYSQCLPNNQAPPS---------------------TTTQPGT
AF315681   (51)  CVYSNDYYSQCLPGAASSSSSTRAASTTSRVSPTTSRSSS----ATPPPG
S76141     (45)  CTVLNPYYSQCLPGSAVTTTSVITSHSSSVS---------S------VSSHSGS
Q8N1B5     (44)  CSTINPYYAQCVPATATPTTLTTTTKPTSTGGAAP----------TTPPPT
AF411251   (45)  CTVVNAYYSQCLPGSASAPP--------------------T----STSSIGT
P07987     (51)  CVYSNDYYSQCLPGAASSSSSTRAASTTSRVSPTTSRSSS----ATPPPG
Consensus (51)   CV LNDYYSQCLPGSASSTTST TTSSTS           S     TT PPT 101                                              150
Q9C1S9     (100) TRTVTIPGGATTTASYN-----GNPFEGVQLWANNYYRSEVHTLAIPQITD
O93837     (81)  TTTTKASTTATTTAAAS-----GNPFSGYQLYANPYYSSEVHTLAIPSLTG
P49075     (72)  TPPATTSGGTGPTSG----AGNPYTGKTVWLSPFYADEVAQAAADISNP
AF315681   (97)  STTTRVPPVGSTATYS-----GNPFVGVTPWANAYYASEVSSLAIPSLTG
S76141     (84)  STSTSSPTGPTGTNPPPPPSANNPWTGFQIFLSPYYANEVAAAAKQITDP
Q8N1B5     (85)  TTGTTTSPVVTRPASAS-----GNPFEGYQLYANPYYASEVISLAIPSLSS
AF411251   (73)  GTTTSSAPGSTGTTTP-----AAGNPFT-EQIYLSPYYANEIAAAVTQISDP
P07987     (97)  STTTRVPPVGSTATYS-----GNPFVGVTPWANAYYASEVSSLAIPSLTG
Consensus (101) TTTTTSPPGGTGTAS S    GNPFTG QLWANPYYASEVASLAIPSLT 151                                              200
Q9C1S9     (146) PALRAAASAVAEVPSFQWLDRNVTVDTLLVETLSEIRAANQAGANPPYAA
O93837     (127) -SLAAAATKAAEIPSFVWLDTAAKVP-TMGTYLANIEAANKAGASPPIAG
P49075     (118) -SLATKAASVAKIPTFVWFDTVAKVP-DLGGYLADARS-------KN-QLV
AF315681  (143) -AMATAAAAVAKVPSFMWLDTLDKTP-LMEQTLADIRTANKNGGN--YAG
S76141     (134) -TLSSKAASVANIPTFTWLDSVAKIP-DLGTYLASASALGKSTGTK-QLV
Q8N1B5     (131) -ELVPKASEVAKVPSFVWLDQAAKVP-SMGDYLKDIQSQNAAGADPPIAG
AF411251  (119) -TTAAAAAKVANIPTFIWLDQVAKVP-DLGTYLADASAKQKSEGKN-YLV
P07987    (143) -AMATAAAAVAKVPSFMWLDTLDKTP-LMEQTLADIRTANKNGGN--YAG
Consensus151)    ALATAAAAVAKIPSFVWLDTVAKVP LG YLADIRAANKAGG   YAG
```

Figure 3B

```
                201                                                250
Q9C1S9    (196) QIVVYDLPDRDCAAAASNGEWAIANNGANNYKGYINRIREILISFSDVRT
O93837    (175) IFVVYDLPDRDCAAAASNGEYTVANNGVANYKAYIDSIVAQLKAYPDVHT
P49075    (159) QIVVYDLPDRDCAALASNGEFSLANDGLNKYKNYVDQIAAQIKQFPDVSV
AF315681  (189) QFVVYDLPDRDCAALASNGEYSIADGGVAKYKNYIDTIRQIVVEYSDIRT
S76141    (181) QIVIYDLPDRDCAAKASNGEFSIANNGQANYENYIDQIVAQIQQFPDVRV
Q8N1B5    (179) IFVVYDLPDRDCAAAASNGEFSIANNGVALYKQYIDSIREQLTTYSDVHT
AF411251  (166) QIVVYDLPDRDCAALASNGEFTIADNGEANYHDYIDQIVAQIKQYPDVHV
P07987    (189) QFVVYDLPDRDCAALASNGEYSIADGGVAKYKNYIDTIRQIVVEYSDIRT
Consensus (201) QIVVYDLPDRDCAALASNGEFSIANNGVANYKNYIDSIRAQI  YSDVRT 251                                                300
Q9C1S9    (246) ILVIEPDSLANMVTNMNVAKCSGAASTYRELTIYALKQLDLPHVAMYMDA
O93837    (225) ILIIEPDSLANMVTNLSTAKCAEAQSAYYECVNYALINLNLANVAMYIDA
P49075    (209) VAVIEPDSLANLVTNLNVQKCANAQSAYKEGVIYAVQKLNAVGVTMYIDA
AF315681  (239) LLVIEPDSLANLVTNLGTPKCANAQSAYLECINYAVTQLNLPNVAMYLDA
S76141    (231) VAVIEPDSLANLVTNLNVQKCANAKTTYLACVNYALTNLAKVGVYMYMDA
Q8N1B5    (229) ILVIEPDSLANVVTNLNVPKCANAQDAYLECINYAITQLDLPNVAMYLDA
AF411251  (216) VAVIEPDSLANLVTNLSVAKCANAQTTYLECVTYAMQQLSAVGVTMYLDA
P07987    (239) LLVIEPDSLANLVTNLGTPKCANAQSAYLECINYAVTQLNLPNVAMYLDA
Consensus (251) ILVIEPDSLANLVTNLNV KCANAQSAYLECVNYALTQLNLPNVAMYLDA 301                                                350
Q9C1S9    (296) GHAGWLGWPANIQPAAELFAKIYEDAGKPRAVRGLATNVANYNAWSISSP
O93837    (275) GHAGWLGWSANLSPAAQLFATVYKNASAPASLRGLATNVANYNAWSISSP
P49075    (259) GHAGWLGWPANLSPAAQLFAQIYRDAGSPRNLRGIATNVANFNALRASSP
AF315681  (289) GHAGWLGWPANQDPAAQLFANVYKNASSPRALRGLATNVANYNGWNITSP
S76141    (281) GHAGWLGWPANLSPAAQLFTQVWQNAGKSPFIKGLATNVANYNALQAASP
Q8N1B5    (279) GHAGWLGWQANLAPAAQLFASVYKNASSPASVRGLATNVANYNAWSISRC
AF411251  (266) GHAGWLGWPANLSPAAQLFTSLYSNAGSPSGVRGLATNVANYNALVATTP
P07987    (289) GHAGWLGWPANQDPAAQLFANVYKNASSPRALRGLATNVANYNGWNITSP
Consensus (301) GHAGWLGWPANLSPAAQLFANVYKNASSPRALRGLATNVANYNAW ISSP 351                                                400
Q9C1S9    (346) PPYTSPNPNYDEKHYIEAFRPLLEARGFP-AQFIVDQGRSGKQPTGQKEW
O93837    (325) PSYTSGDSNYDEKLYINALSPLLTSNGWPNAHFIMDTSRNGVQPTKQQAW
P49075    (309) DPITQGNSNYDEIHYIEALAPMLSN-AGFPAHFIVDQGRSGVQNIR-DQW
AF315681  (339) PSYTQGNAVYNEKLYIHAIGRLLANHGWSNAFFITDQGRSGKQPTGQQQW
S76141    (331) DPITQGNPNYDEIHYINALAPLLQQ-AGWDATFIVDQGRSGVQNIR-QQW
Q8N1B5    (329) PSYTQGDANCDEEDYVNALGPLFQEQGFP-AYFIIDTSRNGVRPTKQSQW
AF411251  (316) DPITQGDPNYDEMLYIEALAPLLG----SFPAHFIVDQGRSGVQDIR-QQW
P07987    (339) PSYTQGNAVYNEKLYIHAIGPLLANHGWSNAFFITDQGRSGKQPTGQQQW
Consensus (351) PSYTQGNANYDEKLYI ALAPLL N GW  AHFIVDQGRSGVQPTRQQQW
```

Figure 3C

```
              401                                                450
Q9C1S9   (395) GHWCNAIGTGFGMRPTANTGHQYVDAFVWVKPGGECDGTSDTTAARYDYH
O93837   (375) GDWCNVIGTGFGVQPTTNTGDPLEDAFVWVKPGGESDGTSNSSATRYDFH
P49075   (357) GDWCNVKGAGFGQRPTTNTGSSLIDAIVWVKPGGECDGTSDNSSPRFDSH
AF315681 (389) GDWCNVIGTGFGIRPSANTGDSLLDSFVWVKPGGECDGTSDSSAPRFDSH
S76141   (379) GDWCNIKGAGFGTRPTTNTGSQFIDSIVWVKPGGECDGTSNSSSPRYDST
Q8N1B5   (378) GDWCNVIGTGFGVRPTTDTGNPLEDAFVWVKPGGESDGTSNTTSPRYDYH
AF411251 (362) GDWCNVLGAGFGTQPTTNTGSSLIDSIVWVKPGGECDGTSNTSSPRYDAH
P07987   (389) GDWCNVIGTGFGIRPSANTGDSLLDSFVWVKPGGECDGTSDSSAPRFDSH
Consensus(401) GDWCNVIGTGFGIRPTTNTG SLIDAFVWVKPGGECDGTSNSSAPRYDSH 451                    484
Q9C1S9   (445) CGLEDALKPAPEAGQWFQAYFEQLLRNANPPF---
O93837   (425) CGYSDALQPAPEAGTWFQAYFVQLLTNANPALV-
P49075   (407) CSLSDAHQPAPEAGTWFQAYFETLVANANPAL---
AF315681 (439) CALPDALQPAPQAGAWFQAYFVQLLTNANPSFL-
S76141   (429) CSLPDAAQPAPEAGTWFQAYFQTLVSAANPPL---
Q8N1B5   (428) CGLSDALQPAPEAGTWFQAYFEQLLTNANPLF---
AF411251 (412) CGLPDATPNAPEAGTWFQAYFETLVEKANPPL---
P07987   (439) CALPDALQPAPQAGAWFQAYFVQLLTNANPSFL-
Consensus(451) CGLPDALQPAPEAGTWFQAYFEQLLTNANPAL
```

Figure 3: Alignment H. jecorina CBH2 with molecules derived from *Humicola insolens* (Q9C1S9), *Acremonium cellulotyticus* (O93837), *Agaricus bisporus* (P49075), *Hypocrea koningii* (AF315681), *Phanerochaete chrysosporium* (S76141), *Talaromyces emersonii* (Q8N1B5), *Lentinula edodes* (AF411251), *Hypocrea jecorina* (P07987).

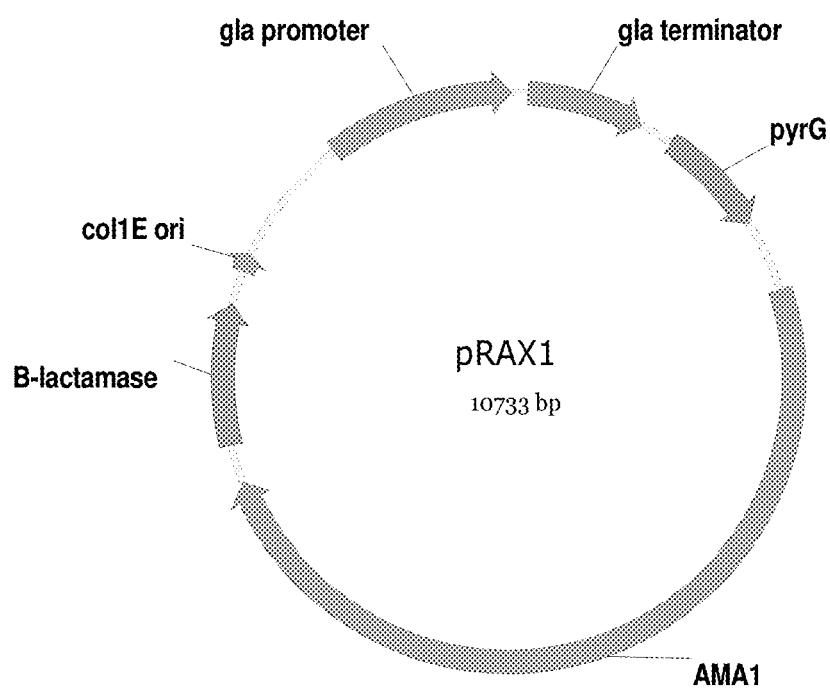
Figure 4: pRAX1

Figure 5: Destination vector pRAXdes2 for expression in *A. niger*
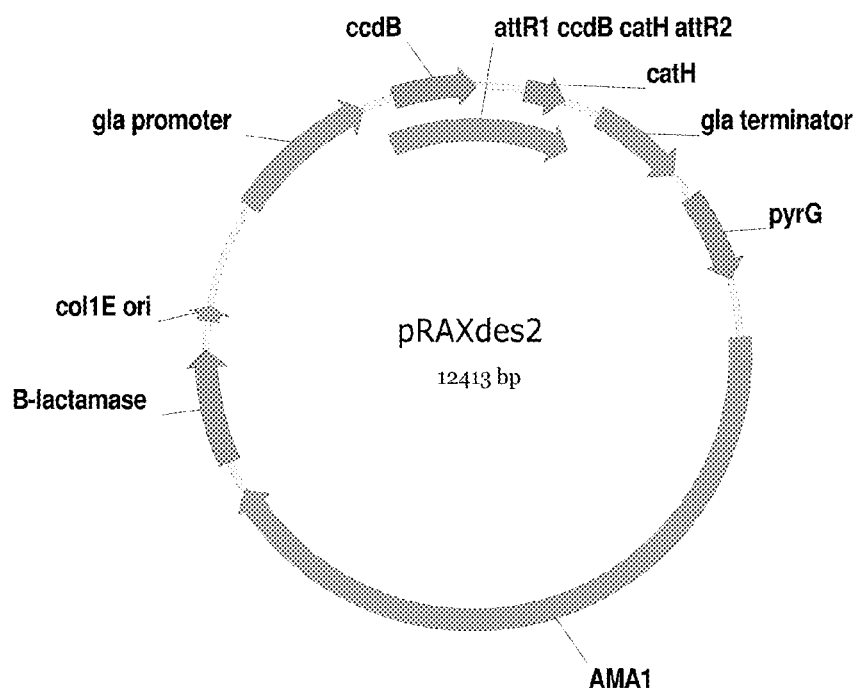

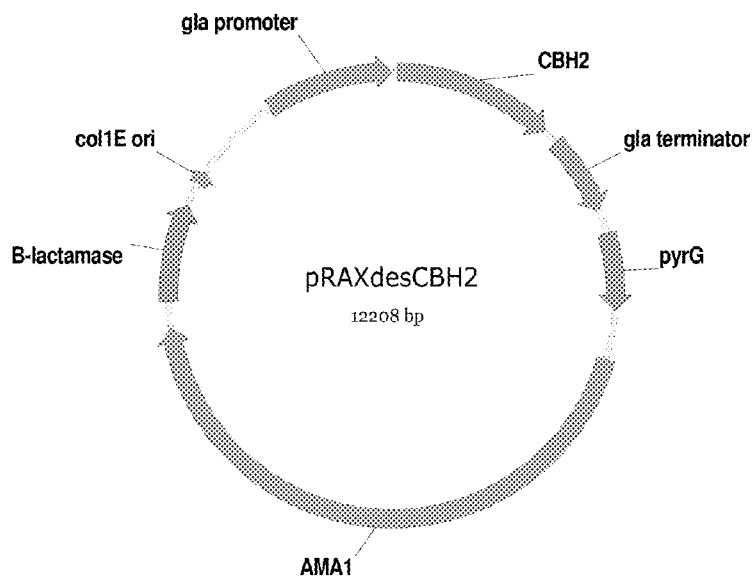
Figure 6: Replicative expression pRAXdesCBH2 vector of CBH2 genes under the control of the glucoamylase promotor. (The CBH2 gene denoted in this figure as CBH2 is the attB1-CBH2-attB2 gene construct.)

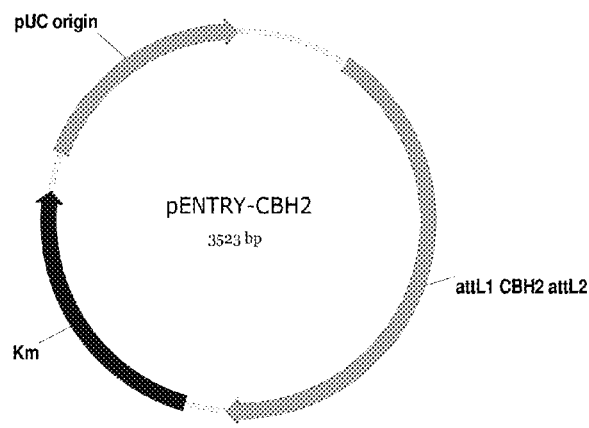
Figure 7: pENTRY-CBH2 used to prepare the expression vector pRAXdesCBH2 through Gateway technology and as template for Quikchange Multi Site-Directed Mutagenesis.

SEQUENCE LISTING

```
<160> NUMBER OF SEQ ID NOS: 95

<210> SEQ ID NO 1
<211> LENGTH: 1416
<212> TYPE: DNA
<213> ORGANISM: Humicola jecorina

<400> SEQUENCE: 1
atgattgtcg gcattctcac cacgctggct acgctggcca cactcgcagc tagtgtgcct      60
ctagaggagc ggcaagcttg ctcaagcgtc tggggccaat gtggtggcca gaattggtcg     120
ggtccgactt gctgtgcttc cggaagcaca tgcgtctact ccaacgacta ttactcccag     180
tgtcttcccg gcgctgcaag ctcaagctcg tccacgcgcg ccgcgtcgac gacttctcga     240
gtatccccca caacatcccg gtcgagctcc gcgacgcctc cacctggttc tactactacc     300
agagtacctc cagtcggatc gggaaccgct acgtattcag gcaacccttt tgttggggtc     360
actccttggg ccaatgcata ttacgcctct gaagttagca gcctcgctat tcctagcttg     420
actggagcca tggccactgc tgcagcagct gtcgcaaagg ttccctcttt tatgtggcta     480
gatactcttg acaagacccc tctcatggag caaaccttgg ccgacatccg caccgccaac     540
aagaatggcg gtaactatgc cggacagttt gtggtgtatg acttgccgga tcgcgattgc     600
```

```
gctgcccttg cctcgaatgg cgaatactct attgccgatg gtggcgtcgc caaatataag    660
aactatatcg acaccattcg tcaaattgtc gtggaatatt ccgatatccg gacccttcctg   720 gttattgagc ctgactctct tgccaacctg gtgaccaacc tcggtactcc aaagtgtgcc    780
aatgctcagt cagcctacct tgagtgcatc aactacgccg tcacacagct gaaccttcca    840
aatgttgcga tgtatttgga cgctggccat gcaggatggc ttggctggcc ggcaaaccaa    900
gacccggccg ctcagctatt tgcaaatgtt tacaagaatg catcgtctcc gagagctctt    960
cgcggattgg caaccaatgt cgccaactac aacgggtgga acattaccag ccccccatcg   1020
tacacgcaag gcaacgctgt ctacaacgag aagctgtaca tccacgctat tggacctctt   1080
cttgccaatc acggctggtc caacgccttc ttcatcactg atcaaggtcg atcgggaaag   1140
cagcctaccg gacagcaaca gtggggagac tggtgcaatg tgatcggcac cggatttggt   1200
attcgcccat ccgcaaacac tgggactcg ttgctggatt cgtttgtctg ggtcaagcca    1260
ggcggcgagt gtgacggcac cagcgacagc agtgcgccac gatttgactc ccactgtgcg   1320
ctcccagatg ccttgcaacc ggcgcctcaa gctggtgctt ggttccaagc ctactttgtg   1380
cagcttctca caaacgcaaa cccatcgttc ctgtaa                             1416

<210> SEQ ID NO 2
<211> LENGTH: 471
<212> TYPE: PRT
<213> ORGANISM: Humicola jecorina

<400> SEQUENCE: 2

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Gly
                85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
        130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
        195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
```

```
                225                 230                 235                 240
Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
                260                 265                 270

Ala Val Thr Gln Leu Asn Leu Pro Asn Val Ala Met Tyr Leu Asp Ala
                275                 280                 285

Gly His Ala Gly Trp Leu Gly Trp Pro Ala Asn Gln Asp Pro Ala Ala
                290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
                340                 345                 350

Tyr Ile His Ala Ile Gly Pro Leu Leu Ala Asn His Gly Trp Ser Asn
                355                 360                 365

Ala Phe Phe Ile Thr Asp Gln Gly Arg Ser Gly Lys Gln Pro Thr Gly
                370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Ser Ser Ser Ala
                420                 425                 430

Pro Arg Phe Asp Ser His Cys Ala Leu Pro Asp Ala Leu Gln Pro Ala
                435                 440                 445

Pro Gln Ala Gly Ala Trp Phe Gln Ala Tyr Phe Val Gln Leu Leu Thr
                450                 455                 460

Asn Ala Asn Pro Ser Phe Leu
465                 470

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgattgtcg gcattctcac                                               20

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ttacaggaac gatgggtttg cg                                            22

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
```
acgtattcag gcaaccc					17

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
gcagtggcca tggctcc					17

<210> SEQ ID NO 7
<211> LENGTH: 34
<212> TYPE: DNA
<213> ORGANISM: Artificial Sequence
<220> FEATURE:
<223> OTHER INFORMATION: primer

<400> SEQUENCE: 7
caggcaaccc ttttgaaggg gtcactcctt ggcg					34

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
caaccctttt gttggggtca ctctttgggc caatgc					36

<210> SEQ ID NO 9
<211> LENGTH: 37
<212> TYPE: DNA
<213> ORGANISM: Artificial Sequence
<220> FEATURE:
<223> OTHER INFORMATION: primer

<400> SEQUENCE: 9
gctattccta gcttgactcc agccatggcc actgctg					37

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
tcctagcttg actggagccc tggccactgc tgc					33

<210> SEQ ID NO 11
<211> LENGTH: 43
<212> TYPE: DNA
<213> ORGANISM: Artificial Sequence
<220> FEATURE:
<223> OTHER INFORMATION: primer

<400> SEQUENCE: 11
gctgtcgcaa aggttccctc ttttgtgtgg ctagatactc ttg					43

<210> SEQ ID NO 12
<211> LENGTH: 42
<212> TYPE: DNA
<213> ORGANISM: Artificial Sequence -continued

```
<220> FEATURE:
<223> OTHER INFORMATION: primer

<400> SEQUENCE: 12
gatactcttg acaaggtccc tctcatggag caaaccttgg cc                    42

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
caagacccct ctcctggagc aaaccttggc cgac                             34

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14
gacccctctc atggagcaat acttggccga catccg                           36

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
cgacatccgc gccgccaaca agaatggcgg                                  30

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
cgattgcgct gccgctgcct cgaatggcg                                   29

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
cgacaccatt cgtgaaattg tcgtggaata ttccgatatc cg                    42

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
cgacaccatt cgtcaaattc tcgtggaata ttccgatatc cg                    42
```

```
<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
gaatattccg atgtccggac cctcctggtt attgagcctg                              40

<210> SEQ ID NO 20
<211> LENGTH: 43
<212> TYPE: DNA
<213> ORGANISM: Artificial Sequence
<220> FEATURE:
<223> OTHER INFORMATION: primer

<400> SEQUENCE: 20
ggaatattcc gatatccgga ccatcctggt tattgagcct gac                          43

<210> SEQ ID NO 21
<211> LENGTH: 42
<212> TYPE: DNA
<213> ORGANISM: Artificial Sequence
<220> FEATURE:
<223> OTHER INFORMATION: primer

<400> SEQUENCE: 21
ctggtgacca acctcaatac tccaaagtgt gccaatgctc ag                           42

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
gaccaacctc ggtgttccaa agtgtgccaa tgctcag                                 37

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
tgagtgcatc aactacgcca tcacacagct gaaccttcc                               39

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
ccggcaaacc tagacccggc cgctcagcta tttg                                    34

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
```

-continued ggccgctcag ctatttgcac aagtttacaa gaatgcatcg                    40

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
gtttacaaga atgcagggtc tccgagagct cttcgcgg                      38

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
gtcgccaact acaacgcgtg gaacattacc agccc                         35

<210> SEQ ID NO 28
<211> LENGTH: 34
<212> TYPE: DNA
<213> ORGANISM: Artificial Sequence
<220> FEATURE:
<223> OTHER INFORMATION: primer

<400> SEQUENCE: 28
caacgggtgg aacattagca gcccccatc gtac                           34

<210> SEQ ID NO 29
<211> LENGTH: 31
<212> TYPE: DNA
<213> ORGANISM: Artificial Sequence
<220> FEATURE:
<223> OTHER INFORMATION: primer

<400> SEQUENCE: 29
cattaccagc cccccaccgt acacgcaagg c                             31

<210> SEQ ID NO 30
<211> LENGTH: 41
<212> TYPE: DNA
<213> ORGANISM: Artificial Sequence
<220> FEATURE:
<223> OTHER INFORMATION: primer

<400> SEQUENCE: 30
caaggcaacg ctaactacaa cgagaagctg tacatccacg c                  41

<210> SEQ ID NO 31
<211> LENGTH: 39
<212> TYPE: DNA
<213> ORGANISM: Artificial Sequence
<220> FEATURE:
<223> OTHER INFORMATION: primer

<400> SEQUENCE: 31
caaggcaacg ctgtctacga cgagaagctg tacatccac                     39

<210> SEQ ID NO 32
<211> LENGTH: 40
<212> TYPE: DNA
<213> ORGANISM: Artificial Sequence

```
<220> FEATURE:
<223> OTHER INFORMATION: primer

<400> SEQUENCE: 32
gctgtacatc cacgctcttg gacctcttct tgccaatcac                              40

<210> SEQ ID NO 33
<211> LENGTH: 38
<212> TYPE: DNA
<213> ORGANISM: Artificial Sequence
<220> FEATURE:
<223> OTHER INFORMATION: primer

<400> SEQUENCE: 33
tacatccacg ctattgcacc tcttcttgcc aatcacgg                                38

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ccaatcacgg ctggcccaac gccttcttca tc                                      32

<210> SEQ ID NO 35
<211> LENGTH: 40
<212> TYPE: DNA
<213> ORGANISM: Artificial Sequence
<220> FEATURE:
<223> OTHER INFORMATION: primer

<400> SEQUENCE: 35
caacgccttc ttcatccttg atcaaggtcg atcgggaaag                              40

<210> SEQ ID NO 36
<211> LENGTH: 38
<212> TYPE: DNA
<213> ORGANISM: Artificial Sequence
<220> FEATURE:
<223> OTHER INFORMATION: primer

<400> SEQUENCE: 36
gaaagcagcc taccagacag caacagtggg gagactgg                                38

<210> SEQ ID NO 37
<211> LENGTH: 33
<212> TYPE: DNA
<213> ORGANISM: Artificial Sequence
<220> FEATURE:
<223> OTHER INFORMATION: primer

<400> SEQUENCE: 37
ggtattcgcc caaccgcaaa cactggggac tcg                                     33

<210> SEQ ID NO 38
<211> LENGTH: 36
<212> TYPE: DNA
<213> ORGANISM: Artificial Sequence
<220> FEATURE:
<223> OTHER INFORMATION: primer

<400> SEQUENCE: 38
ggtattcgcc catccacaaa cactggggac tcgttg                                  36
```

```
<210> SEQ ID NO 39
<211> LENGTH: 35
<212> TYPE: DNA
<213> ORGANISM: Artificial Sequence
<220> FEATURE:
<223> OTHER INFORMATION: primer

<400> SEQUENCE: 39
gactcgttgc tggatgcgtt tgtctgggtc aagcc                              35

<210> SEQ ID NO 40
<211> LENGTH: 33
<212> TYPE: DNA
<213> ORGANISM: Artificial Sequence
<220> FEATURE:
<223> OTHER INFORMATION: primer

<400> SEQUENCE: 40
agtgcgccac gatatgactc ccactgtgcg ctc                                33

<210> SEQ ID NO 41
<211> LENGTH: 35
<212> TYPE: DNA
<213> ORGANISM: Artificial Sequence
<220> FEATURE:
<223> OTHER INFORMATION: primer

<400> SEQUENCE: 41
gccacgattt gactaccact gtgcgctccc agatg                              35

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
tttgactccc actgtgggct cccagatgcc ttg                                33

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
caaccggcgc ctgaagctgg tgcttggttc                                    30

<210> SEQ ID NO 44
<211> LENGTH: 39
<212> TYPE: DNA
<213> ORGANISM: Artificial Sequence
<220> FEATURE:
<223> OTHER INFORMATION: primer

<400> SEQUENCE: 44
gcgcctcaag ctggtacttg gttccaagcc tactttgtg                          39

<210> SEQ ID NO 45
<211> LENGTH: 36
<212> TYPE: DNA
<213> ORGANISM: Artificial Sequence
<220> FEATURE:
<223> OTHER INFORMATION: primer

<400> SEQUENCE: 45
```
caaccctttt gttggggtca ctctttgggc caatgc       36

<210> SEQ ID NO 46
<211> LENGTH: 43
<212> TYPE: DNA
<213> ORGANISM: Artificial Sequence
<220> FEATURE:
<223> OTHER INFORMATION: primer

<400> SEQUENCE: 46
gctgtcgcaa aggttccctc ttttgtgtgg ctagatactc ttg       43

<210> SEQ ID NO 47
<211> LENGTH: 42
<212> TYPE: DNA
<213> ORGANISM: Artificial Sequence
<220> FEATURE:
<223> OTHER INFORMATION: primer

<400> SEQUENCE: 47
cgacaccatt cgtcaaattc tcgtggaata ttccgatatc cg       42

<210> SEQ ID NO 48
<211> LENGTH: 40
<212> TYPE: DNA
<213> ORGANISM: Artificial Sequence
<220> FEATURE:
<223> OTHER INFORMATION: primer

<400> SEQUENCE: 48
gaatattccg atgtccggac cctcctggtt attgagcctg       40

<210> SEQ ID NO 49
<211> LENGTH: 40
<212> TYPE: DNA
<213> ORGANISM: Artificial Sequence
<220> FEATURE:
<223> OTHER INFORMATION: primer

<400> SEQUENCE: 49
cgtcaaattc tcgtggaata ttccgatgtc cggaccctcc       40

<210> SEQ ID NO 50
<211> LENGTH: 34
<212> TYPE: DNA
<213> ORGANISM: Artificial Sequence
<220> FEATURE:
<223> OTHER INFORMATION: primer

<400> SEQUENCE: 50
caacgggtgg aacattagca gccccccatc gtac       34

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51
cattaccagc cccccaccgt acacgcaagg c       31

<210> SEQ ID NO 52
<211> LENGTH: 38
<212> TYPE: DNA
<213> ORGANISM: Artificial Sequence
<220> FEATURE:
<223> OTHER INFORMATION: primer

<400> SEQUENCE: 52
ggtggaacat tagcagcccc ccaccgtaca cgcaaggc                                    38

<210> SEQ ID NO 53
<211> LENGTH: 33
<212> TYPE: DNA
<213> ORGANISM: Artificial Sequence
<220> FEATURE:
<223> OTHER INFORMATION: primer

<400> SEQUENCE: 53
agtgcgccac gatatgactc ccactgtgcg ctc                                         33

<210> SEQ ID NO 54
<211> LENGTH: 35
<212> TYPE: DNA
<213> ORGANISM: Artificial Sequence
<220> FEATURE:
<223> OTHER INFORMATION: primer

<400> SEQUENCE: 54
gccacgattt gactaccact gtgcgctccc agatg                                       35

<210> SEQ ID NO 55
<211> LENGTH: 39
<212> TYPE: DNA
<213> ORGANISM: Artificial Sequence
<220> FEATURE:
<223> OTHER INFORMATION: primer

<400> SEQUENCE: 55
gtgcgccacg atatgactac cactgtgcgc tcccagatg                                   39

<210> SEQ ID NO 56
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 56
cgtcaaattc tcgtggaata tnnsgatatc cggnnsctcc tggttattg                        49

<210> SEQ ID NO 57
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 57
caataaccag gagsnnccgg atatcsnnat attccacgag aatttgacg         49

<210> SEQ ID NO 58
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 58
gtcacacagn nsaacnnscc annsnnsgcg atgtatttg                    39

<210> SEQ ID NO 59
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 59
caaatacatc gcsnnsnntg gsnngttsnn ctgtgtgac                    39

<210> SEQ ID NO 60
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 60
gcgccacgan nsgacnnsca cnnsgcgctc ccagatgcc                                      39

<210> SEQ ID NO 61
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 61
ggcatctggg agcgcsnngt gsnngtcsnn tcgtggcgc                                      39

<210> SEQ ID NO 62
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 62
gcgccacgat ttnnstccnn stgtnnsctc ccagatgcct tg                                  42

<210> SEQ ID NO 63
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 63
caaggcatct gggagsnnac asnnggasnn aaatcgtggc gc                                  42

<210> SEQ ID NO 64
<211> LENGTH: 43
<212> TYPE: DNA
<213> ORGANISM: Artificial Sequence

```
<220> FEATURE:
<223> OTHER INFORMATION: primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t

<400> SEQUENCE: 64
caacgggtgg aacattnnsn nsccccacc gtacacgcaa ggc              43

<210> SEQ ID NO 65
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 65
gccttgcgtg tacggtgggg gsnnsnnaat gttccacccg ttg              43

<210> SEQ ID NO 66
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(29)
<223> OTHER INFORMATION: n is a, c, g, or t

<400> SEQUENCE: 66
cccccaccgt acacgcaagg caacgctnns tacaacgaga ag               42

<210> SEQ ID NO 67
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (14)..(15)
<223> OTHER INFORMATION: n is a, c, g, or t

<400> SEQUENCE: 67
cttctcgttg tasnnagcgt tgccttgcgt gtacggtggg gg               42

<210> SEQ ID NO 68
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(14)
<223> OTHER INFORMATION: n is a, c, g, or t

<400> SEQUENCE: 68
```

```
gaatattccg atnnscggac cctcctggtt attgagcctg                40
```

<210> SEQ ID NO 69
<211> LENGTH: 40
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (27)..(28)
<223> OTHER INFORMATION: n is a, c, g, or t

<400> SEQUENCE: 69

```
caggctcaat aaccaggagg gtccgsnnat cggaatattc                40
```

<210> SEQ ID NO 70
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 70

```
cctctcatgg agcaaaccnn sgccgacnns cgcaccgcc                 39
```

<210> SEQ ID NO 71
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t

<400> SEQUENCE: 71

```
ggcggtgcgs nngtcggcsn nggtttgctc catgagagg                 39
```

<210> SEQ ID NO 72
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 72

```
ccctcttttn nstggctaga tactcttgac aagacccctn nsatggagca aacc    54
```

<210> SEQ ID NO 73
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 73
ggtttgctcc atsnnagggg tcttgtcaag agtatctagc casnnaaaag aggg         54

<210> SEQ ID NO 74
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t

<400> SEQUENCE: 74 caacccttttt gttggggtca ctnnstgggc caatgc                            36

<210> SEQ ID NO 75
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(14)
<223> OTHER INFORMATION: n is a, c, g, or t

<400> SEQUENCE: 75
gcattggccc asnnagtgac cccaacaaaa gggttg                             36

<210> SEQ ID NO 76
<211> LENGTH: 47
<212> TYPE: DNA
<213> ORGANISM: Artificial Sequence
<220> FEATURE:
<223> OTHER INFORMATION: primer

<400> SEQUENCE: 76 ccagccccc accgtacacg caaggcaacg cttactacaa cgagaag                  47

<210> SEQ ID NO 77
<211> LENGTH: 47
<212> TYPE: DNA
<213> ORGANISM: Artificial Sequence
<220> FEATURE:
<223> OTHER INFORMATION: primer

<400> SEQUENCE: 77
cttctcgttg tagtaagcgt tgccttgcgt gtacggtggg gggctgg                 47

<210> SEQ ID NO 78
<211> LENGTH: 49
<212> TYPE: DNA
<213> ORGANISM: Artificial Sequence

```
<220> FEATURE:
<223> OTHER INFORMATION: primer

<400> SEQUENCE: 78
cgtcaaattg tcgtggaata tcgcgatatc cggtacctcc tggttattg            49

<210> SEQ ID NO 79
<211> LENGTH: 49
<212> TYPE: DNA
<213> ORGANISM: Artificial Sequence
<220> FEATURE:
<223> OTHER INFORMATION: primer

<400> SEQUENCE: 79
caataaccag gaggtaccgg atatcgcgat attccacgac aatttgacg             49

<210> SEQ ID NO 80
<211> LENGTH: 49
<212> TYPE: DNA
<213> ORGANISM: Artificial Sequence
<220> FEATURE:
<223> OTHER INFORMATION: primer

<400> SEQUENCE: 80
cgtcaaattg tcgtggaata tctcgatatc cggtacctcc tggttattg             49

<210> SEQ ID NO 81
<211> LENGTH: 49
<212> TYPE: DNA
<213> ORGANISM: Artificial Sequence
<220> FEATURE:
<223> OTHER INFORMATION: primer

<400> SEQUENCE: 81
caataaccag gaggtaccgg atatcgagat attccacgac aatttgacg             49

<210> SEQ ID NO 82
<211> LENGTH: 49
<212> TYPE: DNA
<213> ORGANISM: Artificial Sequence
<220> FEATURE:
<223> OTHER INFORMATION: primer

<400> SEQUENCE: 82
cgtcaaattc tcgtggaata tcgcgatatc cggtacctcc tggttattg             49

<210> SEQ ID NO 83
<211> LENGTH: 49
<212> TYPE: DNA
<213> ORGANISM: Artificial Sequence
<220> FEATURE:
<223> OTHER INFORMATION: primer

<400> SEQUENCE: 83
caataaccag gaggtaccgg atatcgcgat attccacgag aatttgacg             49

<210> SEQ ID NO 84
<211> LENGTH: 54
<212> TYPE: DNA
<213> ORGANISM: Artificial Sequence
<220> FEATURE:
<223> OTHER INFORMATION: primer

<400> SEQUENCE: 84
ccctcttttc tgtggctaga tactcttgac aagacccctc gcatggagca aacc        54
```

```
<210> SEQ ID NO 85
<211> LENGTH: 54
<212> TYPE: DNA
<213> ORGANISM: Artificial Sequence
<220> FEATURE:
<223> OTHER INFORMATION: primer

<400> SEQUENCE: 85
ggtttgctcc atgcgagggg tcttgtcaag agtatctagc cacagaaaag aggg      54

<210> SEQ ID NO 86
<211> LENGTH: 476
<212> TYPE: PRT
<213> ORGANISM: Humicola insolens

<400> SEQUENCE: 86
```

| Met | Ala | Lys | Phe | Phe | Leu | Thr | Ala | Ala | Phe | Ala | Ala | Ala | Leu | Ala |
|---|---|---|---|---|---|---|---|---|---|---|---|---|---|---|
| 1 | | | | 5 | | | | | 10 | | | | | 15 |

| Ala | Pro | Val | Val | Glu | Glu | Arg | Gln | Asn | Cys | Ala | Pro | Thr | Trp | Gly | Gln |
|---|---|---|---|---|---|---|---|---|---|---|---|---|---|---|---|
| | | | 20 | | | | | 25 | | | | | 30 | | |

Cys Gly Gly Ile Gly Phe Asn Gly Pro Thr Cys Cys Gln Ser Gly Ser
         35                  40                  45

Thr Cys Val Lys Gln Asn Asp Trp Tyr Ser Gln Cys Leu Pro Gly Ser
 50                  55                  60

Gln Val Thr Thr Thr Ser Thr Thr Ser Thr Ser Ser Ser Ser Thr Thr
 65                  70                  75                  80

Ser Arg Ala Thr Ser Thr Thr Arg Thr Gly Gly Val Thr Ser Ile Thr
                 85                  90                  95

Thr Ala Pro Thr Arg Thr Val Thr Ile Pro Gly Gly Ala Thr Thr Thr
                100                 105                 110

Ala Ser Tyr Asn Gly Asn Pro Phe Glu Gly Val Gln Leu Trp Ala Asn
             115                 120                 125

Asn Tyr Tyr Arg Ser Glu Val His Thr Leu Ala Ile Pro Gln Ile Thr
 130                 135                 140

Asp Pro Ala Leu Arg Ala Ala Ser Ala Val Ala Glu Val Pro Ser
145                 150                 155                 160

Phe Gln Trp Leu Asp Arg Asn Val Thr Val Asp Thr Leu Leu Val Glu
                165                 170                 175

Thr Leu Ser Glu Ile Arg Ala Ala Asn Gln Ala Gly Ala Asn Pro Pro
            180                 185                 190

Tyr Ala Ala Gln Ile Val Val Tyr Asp Leu Pro Asp Arg Asp Cys Ala
        195                 200                 205

Ala Ala Ala Ser Asn Gly Glu Trp Ala Ile Ala Asn Asn Gly Ala Asn
210                 215                 220

Asn Tyr Lys Gly Tyr Ile Asn Arg Ile Arg Glu Ile Leu Ile Ser Phe
225                 230                 235                 240

Ser Asp Val Arg Thr Ile Leu Val Ile Glu Pro Asp Ser Leu Ala Asn
                245                 250                 255

Met Val Thr Asn Met Asn Val Ala Lys Cys Ser Gly Ala Ala Ser Thr
            260                 265                 270

Tyr Arg Glu Leu Thr Ile Tyr Ala Leu Lys Gln Leu Asp Leu Pro His
        275                 280                 285

Val Ala Met Tyr Met Asp Ala Gly His Ala Gly Trp Leu Gly Trp Pro
    290                 295                 300

Ala Asn Ile Gln Pro Ala Ala Glu Leu Phe Ala Lys Ile Tyr Glu Asp
305                 310                 315                 320

Ala Gly Lys Pro Arg Ala Val Arg Gly Leu Ala Thr Asn Val Ala Asn

```
                     325                 330                 335
Tyr Asn Ala Trp Ser Ile Ser Ser Pro Pro Tyr Thr Ser Pro Asn
            340                 345                 350

Pro Asn Tyr Asp Glu Lys His Tyr Ile Glu Ala Phe Arg Pro Leu Leu
                355                 360                 365

Glu Ala Arg Gly Phe Pro Ala Gln Phe Ile Val Asp Gln Gly Arg Ser
370                 375                 380

Gly Lys Gln Pro Thr Gly Gln Lys Glu Trp Gly His Trp Cys Asn Ala
385                 390                 395                 400

Ile Gly Thr Gly Phe Gly Met Arg Pro Thr Ala Asn Thr Gly His Gln
                405                 410                 415

Tyr Val Asp Ala Phe Val Trp Val Lys Pro Gly Gly Glu Cys Asp Gly
                420                 425                 430

Thr Ser Asp Thr Thr Ala Ala Arg Tyr Asp Tyr His Cys Gly Leu Glu
                435                 440                 445

Asp Ala Leu Lys Pro Ala Pro Glu Ala Gly Gln Trp Phe Gln Ala Tyr
450                 455                 460

Phe Glu Gln Leu Leu Arg Asn Ala Asn Pro Pro Phe
465                 470                 475

<210> SEQ ID NO 87
<211> LENGTH: 457
<212> TYPE: PRT
<213> ORGANISM: Acremonium cellulolyticus

<400> SEQUENCE: 87

Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
                20                  25                  30

Ser Gly Ala Thr Ser Cys Ala Ala Gly Ser Thr Cys Ser Thr Leu Asn
            35                  40                  45

Pro Tyr Tyr Ala Gln Cys Ile Pro Gly Thr Ala Thr Ser Thr Thr Leu
        50                  55                  60

Val Lys Thr Thr Ser Ser Thr Ser Val Gly Thr Thr Ser Pro Pro Thr
65                  70                  75                  80

Thr Thr Thr Thr Lys Ala Ser Thr Thr Thr Thr Thr Ala Ala Ala
                85                  90                  95

Ser Gly Asn Pro Phe Ser Gly Tyr Gln Leu Tyr Ala Asn Pro Tyr Tyr
                100                 105                 110

Ser Ser Glu Val His Thr Leu Ala Ile Pro Ser Leu Thr Gly Ser Leu
            115                 120                 125

Ala Ala Ala Ala Thr Lys Ala Ala Glu Ile Pro Ser Phe Val Trp Leu
        130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Pro Ile Ala Gly Ile Phe
                165                 170                 175

Val Val Tyr Asp Leu Pro Asp Arg Asp Cys Ala Ala Ala Ala Ser Asn
                180                 185                 190

Gly Glu Tyr Thr Val Ala Asn Asn Gly Val Ala Asn Tyr Lys Ala Tyr
            195                 200                 205

Ile Asp Ser Ile Val Ala Gln Leu Lys Ala Tyr Pro Asp Val His Thr
        210                 215                 220

Ile Leu Ile Ile Glu Pro Asp Ser Leu Ala Asn Met Val Thr Asn Leu
```

```
                225                 230                 235                 240
Ser Thr Ala Lys Cys Ala Glu Ala Gln Ser Ala Tyr Tyr Glu Cys Val
                245                 250                 255

Asn Tyr Ala Leu Ile Asn Leu Asn Leu Ala Asn Val Ala Met Tyr Ile
                260                 265                 270

Asp Ala Gly His Ala Gly Trp Leu Gly Trp Ser Ala Asn Leu Ser Pro
                275                 280                 285

Ala Ala Gln Leu Phe Ala Thr Val Tyr Lys Asn Ala Ser Ala Pro Ala
                290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
                340                 345                 350

Pro Asn Ala His Phe Ile Met Asp Thr Ser Arg Asn Gly Val Gln Pro
                355                 360                 365

Thr Lys Gln Gln Ala Trp Gly Asp Trp Cys Asn Val Ile Gly Thr Gly
                370                 375                 380

Phe Gly Val Gln Pro Thr Thr Asn Thr Gly Asp Pro Leu Glu Asp Ala
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Asp Ala Leu Gln
                420                 425                 430

Pro Ala Pro Glu Ala Gly Thr Trp Phe Gln Ala Tyr Phe Val Gln Leu
                435                 440                 445

Leu Thr Asn Ala Asn Pro Ala Leu Val
450                 455

<210> SEQ ID NO 88
<211> LENGTH: 438
<212> TYPE: PRT
<213> ORGANISM: Agaricus bisporus

<400> SEQUENCE: 88

Met Phe Lys Phe Ala Ala Leu Leu Ala Leu Ala Ser Leu Val Pro Gly
1               5                   10                  15

Phe Val Gln Ala Gln Ser Pro Val Trp Gly Gln Cys Gly Gly Asn Gly
                20                  25                  30

Trp Thr Gly Pro Thr Thr Cys Ala Ser Gly Ser Thr Cys Val Lys Gln
                35                  40                  45

Asn Asp Phe Tyr Ser Gln Cys Leu Pro Asn Asn Gln Ala Pro Pro Ser
        50                  55                  60

Thr Thr Gln Pro Gly Thr Thr Pro Ala Thr Thr Ser Gly
65                  70                  75              80

Gly Thr Gly Pro Thr Ser Gly Ala Gly Asn Pro Tyr Thr Gly Lys Thr
                85                  90                  95

Val Trp Leu Ser Pro Phe Tyr Ala Asp Glu Val Ala Gln Ala Ala Ala
                100                 105                 110

Asp Ile Ser Asn Pro Ser Leu Ala Thr Lys Ala Ala Ser Val Ala Lys
            115                 120                 125

Ile Pro Thr Phe Val Trp Phe Asp Thr Val Ala Lys Val Pro Asp Leu
            130                 135                 140

Gly Gly Tyr Leu Ala Asp Ala Arg Ser Lys Asn Gln Leu Val Gln Ile
```

```
                145                 150                 155                 160
Val Val Tyr Asp Leu Pro Asp Arg Asp Cys Ala Ala Leu Ala Ser Asn
                    165                 170                 175

Gly Glu Phe Ser Leu Ala Asn Asp Gly Leu Asn Lys Tyr Lys Asn Tyr
                    180                 185                 190

Val Asp Gln Ile Ala Ala Gln Ile Lys Gln Phe Pro Asp Val Ser Val
                    195                 200                 205

Val Ala Val Ile Glu Pro Asp Ser Leu Ala Asn Leu Val Thr Asn Leu
            210                 215                 220

Asn Val Gln Lys Cys Ala Asn Ala Gln Ser Ala Tyr Lys Glu Gly Val
225                 230                 235                 240

Ile Tyr Ala Val Gln Lys Leu Asn Ala Val Gly Val Thr Met Tyr Ile
                    245                 250                 255

Asp Ala Gly His Ala Gly Trp Leu Gly Trp Pro Ala Asn Leu Ser Pro
                    260                 265                 270

Ala Ala Gln Leu Phe Ala Gln Ile Tyr Arg Asp Ala Gly Ser Pro Arg
                    275                 280                 285

Asn Leu Arg Gly Ile Ala Thr Asn Val Ala Asn Phe Asn Ala Leu Arg
            290                 295                 300

Ala Ser Ser Pro Asp Pro Ile Thr Gln Gly Asn Ser Asn Tyr Asp Glu
305                 310                 315                 320

Ile His Tyr Ile Glu Ala Leu Ala Pro Met Leu Ser Asn Ala Gly Phe
                    325                 330                 335

Pro Ala His Phe Ile Val Asp Gln Gly Arg Ser Gly Val Gln Asn Ile
                    340                 345                 350

Arg Asp Gln Trp Gly Asp Trp Cys Asn Val Lys Gly Ala Gly Phe Gly
                    355                 360                 365

Gln Arg Pro Thr Thr Asn Thr Gly Ser Ser Leu Ile Asp Ala Ile Val
            370                 375                 380

Trp Val Lys Pro Gly Gly Glu Cys Asp Gly Thr Ser Asp Ser Ser Ser
385                 390                 395                 400

Pro Arg Phe Asp Ser His Cys Ser Leu Ser Asp Ala His Gln Pro Ala
                    405                 410                 415

Pro Glu Ala Gly Thr Trp Phe Gln Ala Tyr Phe Glu Thr Leu Val Ala
                    420                 425                 430

Asn Ala Asn Pro Ala Leu
            435

<210> SEQ ID NO 89
<211> LENGTH: 471
<212> TYPE: PRT
<213> ORGANISM: Hypocrea koningii

<400> SEQUENCE: 89

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
                    20                  25                  30

Gln Cys Gly Gly Gln Asn Trp Ser Gly Pro Thr Cys Cys Ala Ser Gly
                    35                  40                  45

Ser Thr Cys Val Tyr Ser Asn Asp Tyr Tyr Ser Gln Cys Leu Pro Gly
            50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Pro Gly
```

-continued

```
                85                  90                  95
Ser Thr Thr Thr Arg Val Pro Val Gly Ser Gly Thr Ala Thr Tyr
            100                 105                 110
Ser Gly Asn Pro Phe Val Gly Val Thr Pro Trp Ala Asn Ala Tyr Tyr
            115                 120                 125
Ala Ser Glu Val Ser Ser Leu Ala Ile Pro Ser Leu Thr Gly Ala Met
            130                 135                 140
Ala Thr Ala Ala Ala Val Ala Lys Val Pro Ser Phe Met Trp Leu
145                 150                 155                 160
Asp Thr Leu Asp Lys Thr Pro Leu Met Glu Gln Thr Leu Ala Asp Ile
                165                 170                 175
Arg Thr Ala Asn Lys Asn Gly Gly Asn Tyr Ala Gly Gln Phe Val Val
                180                 185                 190
Tyr Asp Leu Pro Asp Arg Asp Cys Ala Ala Leu Ala Ser Asn Gly Glu
                195                 200                 205
Tyr Ser Ile Ala Asp Gly Gly Val Ala Lys Tyr Lys Asn Tyr Ile Asp
            210                 215                 220
Thr Ile Arg Gln Ile Val Val Glu Tyr Ser Asp Ile Arg Thr Leu Leu
225                 230                 235                 240
Val Ile Glu Pro Asp Ser Leu Ala Asn Leu Val Thr Asn Leu Gly Thr
                245                 250                 255
Pro Lys Cys Ala Asn Ala Gln Ser Ala Tyr Leu Glu Cys Ile Asn Tyr
                260                 265                 270
Ala Val Thr Gln Leu Asn Leu Pro Asn Val Ala Met Tyr Leu Asp Ala
            275                 280                 285
Gly His Ala Gly Trp Leu Gly Trp Pro Ala Asn Gln Asp Pro Ala Ala
            290                 295                 300
Gln Leu Phe Ala Asn Val Tyr Lys Asn Ala Ser Ser Pro Arg Ala Leu
305                 310                 315                 320
Arg Gly Leu Ala Thr Asn Val Ala Asn Tyr Asn Gly Trp Asn Ile Thr
                325                 330                 335
Ser Pro Pro Ser Tyr Thr Gln Gly Asn Ala Val Tyr Asn Glu Lys Leu
                340                 345                 350
Tyr Ile His Ala Ile Gly Arg Leu Leu Ala Asn His Gly Trp Ser Asn
                355                 360                 365
Ala Phe Phe Ile Thr Asp Gln Gly Arg Ser Gly Lys Gln Pro Thr Gly
            370                 375                 380
Gln Gln Gln Trp Gly Asp Trp Cys Asn Val Ile Gly Thr Gly Phe Gly
385                 390                 395                 400
Ile Arg Pro Ser Ala Asn Thr Gly Asp Ser Leu Leu Asp Ser Phe Val
                405                 410                 415
Trp Val Lys Pro Gly Gly Glu Cys Asp Gly Thr Ser Asp Ser Ser Ala
            420                 425                 430
Pro Arg Phe Asp Ser His Cys Ala Leu Pro Asp Ala Leu Gln Pro Ala
            435                 440                 445
Pro Gln Ala Gly Ala Trp Phe Gln Ala Tyr Phe Val Gln Leu Leu Thr
450                 455                 460
Asn Ala Asn Pro Ser Phe Leu
465                 470
```

<210> SEQ ID NO 90
<211> LENGTH: 460
<212> TYPE: PRT
<213> ORGANISM: Phanerochaete chrysosporium

<400> SEQUENCE: 90

```
Met Lys Ser Thr Ala Phe Phe Ala Ala Leu Val Thr Leu Leu Pro Ala
1               5                   10                  15

Tyr Val Ala Gly Gln Ala Ser Glu Trp Gly Gln Cys Gly Gly Ile Gly
            20                  25                  30

Trp Thr Gly Pro Thr Thr Cys Val Ser Gly Thr Thr Cys Thr Val Leu
        35                  40                  45

Asn Pro Tyr Tyr Ser Gln Cys Leu Pro Gly Ser Ala Val Thr Thr Thr
    50                  55                  60

Ser Val Ile Thr Ser His Ser Ser Val Ser Ser Val Ser Ser His
65                  70                  75                  80

Ser Gly Ser Ser Thr Ser Thr Ser Ser Pro Thr Gly Pro Thr Gly Thr
                85                  90                  95

Asn Pro Pro Pro Pro Ser Ala Asn Asn Pro Trp Thr Gly Phe Gln
                100                 105                 110

Ile Phe Leu Ser Pro Tyr Tyr Ala Asn Glu Val Ala Ala Ala Lys
            115                 120                 125

Gln Ile Thr Asp Pro Thr Leu Ser Ser Lys Ala Ala Ser Val Ala Asn
130                 135                 140

Ile Pro Thr Phe Thr Trp Leu Asp Ser Val Ala Lys Ile Pro Asp Leu
145                 150                 155                 160

Gly Thr Tyr Leu Ala Ser Ala Ser Ala Leu Gly Lys Ser Thr Gly Thr
                165                 170                 175

Lys Gln Leu Val Gln Ile Val Tyr Asp Leu Pro Asp Arg Asp Cys
            180                 185                 190

Ala Ala Lys Ala Ser Asn Gly Glu Phe Ser Ile Ala Asn Asn Gly Gln
            195                 200                 205

Ala Asn Tyr Glu Asn Tyr Ile Asp Gln Ile Val Ala Gln Ile Gln Gln
210                 215                 220

Phe Pro Asp Val Arg Val Val Ala Val Ile Glu Pro Asp Ser Leu Ala
225                 230                 235                 240

Asn Leu Val Thr Asn Leu Asn Val Gln Lys Cys Ala Asn Ala Lys Thr
                245                 250                 255

Thr Tyr Leu Ala Cys Val Asn Tyr Ala Leu Thr Asn Leu Ala Lys Val
            260                 265                 270

Gly Val Tyr Met Tyr Met Asp Ala Gly His Ala Gly Trp Leu Gly Trp
            275                 280                 285

Pro Ala Asn Leu Ser Pro Ala Ala Gln Leu Phe Thr Gln Val Trp Gln
290                 295                 300

Asn Ala Gly Lys Ser Pro Phe Ile Lys Gly Leu Ala Thr Asn Val Ala
305                 310                 315                 320

Asn Tyr Asn Ala Leu Gln Ala Ala Ser Pro Asp Pro Ile Thr Gln Gly
                325                 330                 335

Asn Pro Asn Tyr Asp Glu Ile His Tyr Ile Asn Ala Leu Ala Pro Leu
            340                 345                 350

Leu Gln Gln Ala Gly Trp Asp Ala Thr Phe Ile Val Asp Gln Gly Arg
            355                 360                 365

Ser Gly Val Gln Asn Ile Arg Gln Gln Trp Gly Asp Trp Cys Asn Ile
370                 375                 380

Lys Gly Ala Gly Phe Gly Thr Arg Pro Thr Thr Asn Thr Gly Ser Gln
385                 390                 395                 400

Phe Ile Asp Ser Ile Val Trp Val Lys Pro Gly Gly Glu Cys Asp Gly
                405                 410                 415
```

```
Thr Ser Asn Ser Ser Pro Arg Tyr Asp Ser Thr Cys Ser Leu Pro
            420                 425                 430

Asp Ala Ala Gln Pro Ala Pro Glu Ala Gly Thr Trp Phe Gln Ala Tyr
        435                 440                 445

Phe Gln Thr Leu Val Ser Ala Ala Asn Pro Pro Leu
        450                 455                 460

<210> SEQ ID NO 91
<211> LENGTH: 459
<212> TYPE: PRT
<213> ORGANISM: Talaromyces emersonii

<400> SEQUENCE: 91

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
        35                  40                  45

Pro Tyr Tyr Ala Gln Cys Val Pro Ala Thr Ala Thr Pro Thr Thr Leu
50                  55                  60

Thr Thr Thr Thr Lys Pro Thr Ser Thr Gly Gly Ala Ala Pro Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
210                 215                 220

Asp Val His Thr Ile Leu Val Ile Glu Pro Asp Ser Leu Ala Asn Val
225                 230                 235                 240

Val Thr Asn Leu Asn Val Pro Lys Cys Ala Asn Ala Gln Asp Ala Tyr
                245                 250                 255

Leu Glu Cys Ile Asn Tyr Ala Ile Thr Gln Leu Asp Leu Pro Asn Val
            260                 265                 270

Ala Met Tyr Leu Asp Ala Gly His Ala Gly Trp Leu Gly Trp Gln Ala
        275                 280                 285

Asn Leu Ala Pro Ala Ala Gln Leu Phe Ala Ser Val Tyr Lys Asn Ala
290                 295                 300

Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
                325                 330                 335
```

-continued

```
Asn Cys Asp Glu Glu Asp Tyr Val Asn Ala Leu Gly Pro Leu Phe Gln
            340                 345                 350

Glu Gln Gly Phe Pro Ala Tyr Phe Ile Ile Asp Thr Ser Arg Asn Gly
        355                 360                 365

Val Arg Pro Thr Lys Gln Ser Gln Trp Gly Asp Trp Cys Asn Val Ile
370                 375                 380

Gly Thr Gly Phe Gly Val Arg Pro Thr Thr Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Leu Phe
    450                 455

<210> SEQ ID NO 92
<211> LENGTH: 443
<212> TYPE: PRT
<213> ORGANISM: Lentinula edodes

<400> SEQUENCE: 92

Met Lys Ile Thr Ser Thr Gly Leu Leu Ala Leu Ser Ser Leu Leu Pro
1               5                   10                  15

Phe Ala Leu Gly Gln Ser Gln Leu Tyr Ala Gln Cys Gly Gly Ile Gly
            20                  25                  30

Trp Ser Gly Ala Thr Thr Cys Val Ser Gly Ala Thr Cys Thr Val Val
        35                  40                  45

Asn Ala Tyr Tyr Ser Gln Cys Leu Pro Gly Ser Ala Ser Ala Pro Pro
    50                  55                  60

Thr Ser Thr Ser Ser Ile Gly Thr Gly Thr Thr Thr Ser Ser Ala Pro
65                  70                  75                  80

Gly Ser Thr Gly Thr Thr Thr Pro Ala Ala Gly Asn Pro Phe Thr Glu
                85                  90                  95

Gln Ile Tyr Leu Ser Pro Tyr Tyr Ala Asn Glu Ile Ala Ala Ala Val
            100                 105                 110

Thr Gln Ile Ser Asp Pro Thr Thr Ala Ala Ala Ala Lys Val Ala
        115                 120                 125

Asn Ile Pro Thr Phe Ile Trp Leu Asp Gln Val Ala Lys Val Pro Asp
    130                 135                 140

Leu Gly Thr Tyr Leu Ala Asp Ala Ser Ala Lys Gln Lys Ser Glu Gly
145                 150                 155                 160

Lys Asn Tyr Leu Val Gln Ile Val Val Tyr Asp Leu Pro Asp Arg Asp
                165                 170                 175

Cys Ala Ala Leu Ala Ser Asn Gly Glu Phe Thr Ile Ala Asp Asn Gly
            180                 185                 190

Glu Ala Asn Tyr His Asp Tyr Ile Asp Gln Ile Val Ala Gln Ile Lys
        195                 200                 205

Gln Tyr Pro Asp Val His Val Val Ala Val Ile Glu Pro Asp Ser Leu
    210                 215                 220

Ala Asn Leu Val Thr Asn Leu Ser Val Ala Lys Cys Ala Asn Ala Gln
225                 230                 235                 240

Thr Thr Tyr Leu Glu Cys Val Thr Tyr Ala Met Gln Gln Leu Ser Ala
                245                 250                 255
```

```
Val Gly Val Thr Met Tyr Leu Asp Ala Gly His Ala Gly Trp Leu Gly
            260                 265                 270

Trp Pro Ala Asn Leu Ser Pro Ala Gln Leu Phe Thr Ser Leu Tyr
            275                 280                 285

Ser Asn Ala Gly Ser Pro Ser Gly Val Arg Gly Leu Ala Thr Asn Val
            290                 295                 300

Ala Asn Tyr Asn Ala Leu Val Ala Thr Thr Pro Asp Pro Ile Thr Gln
305                 310                 315                 320

Gly Asp Pro Asn Tyr Asp Glu Met Leu Tyr Ile Glu Ala Leu Ala Pro
                325                 330                 335

Leu Leu Gly Ser Phe Pro Ala His Phe Ile Val Asp Gln Gly Arg Ser
            340                 345                 350

Gly Val Gln Asp Ile Arg Gln Gln Trp Gly Asp Trp Cys Asn Val Leu
            355                 360                 365

Gly Ala Gly Phe Gly Thr Gln Pro Thr Thr Asn Thr Gly Ser Ser Leu
            370                 375                 380

Ile Asp Ser Ile Val Trp Val Lys Pro Gly Gly Glu Cys Asp Gly Thr
385                 390                 395                 400

Ser Asn Thr Ser Ser Pro Arg Tyr Asp Ala His Cys Gly Leu Pro Asp
                405                 410                 415

Ala Thr Pro Asn Ala Pro Glu Ala Gly Thr Trp Phe Gln Ala Tyr Phe
            420                 425                 430

Glu Thr Leu Val Glu Lys Ala Asn Pro Pro Leu
            435                 440

<210> SEQ ID NO 93
<211> LENGTH: 471
<212> TYPE: PRT
<213> ORGANISM: Hypocrea jecorina

<400> SEQUENCE: 93

Met Ile Val Gly Ile Leu Thr Thr Leu Ala Thr Leu Ala Thr Leu Ala
1               5                   10                  15

Ala Ser Val Pro Leu Glu Glu Arg Gln Ala Cys Ser Ser Val Trp Gly
            20                  25                  30

Gln Cys Gly Gly Gln Asn Trp Ser Gly Pro Thr Cys Cys Ala Ser Gly
        35                  40                  45

Ser Thr Cys Val Tyr Ser Asn Asp Tyr Tyr Ser Gln Cys Leu Pro Gly
    50                  55                  60

Ala Ala Ser Ser Ser Ser Thr Arg Ala Ala Ser Thr Thr Ser Arg
65                  70                  75                  80

Val Ser Pro Thr Thr Ser Arg Ser Ser Ser Ala Thr Pro Pro Pro Gly
            85                  90                  95

Ser Thr Thr Thr Arg Val Pro Pro Val Gly Ser Gly Thr Ala Thr Tyr
            100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
            130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190
```

```
Tyr Asp Leu Pro Asp Arg Asp Cys Ala Ala Leu Ala Ser Asn Gly Glu
            195                 200                 205

Tyr Ser Ile Ala Asp Gly Gly Val Ala Lys Tyr Lys Asn Tyr Ile Asp
        210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
        275                 280                 285

Gly His Ala Gly Trp Leu Gly Trp Pro Ala Asn Gln Asp Pro Ala Ala
    290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
        355                 360                 365

Ala Phe Phe Ile Thr Asp Gln Gly Arg Ser Gly Lys Gln Pro Thr Gly
    370                 375                 380

Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Asp Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 94
<211> LENGTH: 476
<212> TYPE: PRT
<213> ORGANISM: Artificial Sequence
<220> FEATURE:
<223> OTHER INFORMATION: consensus of the alignment of SEQ ID NO:86-93
<220> FEATURE:
<221> NAME/KEY: misc_feature
<222> LOCATION: (2)..(2)
<223> OTHER INFORMATION: Xaa can be Met, Phe, Lys, or Thr
<220> FEATURE:
<221> NAME/KEY: misc_feature
<222> LOCATION: (4)..(4)
<223> OTHER INFORMATION: Xaa can be Ala, Arg, Asn, Phe, or Thr
<220> FEATURE:
<221> NAME/KEY: misc_feature
<222> LOCATION: (5)..(5)
<223> OTHER INFORMATION: Xaa can be Ala, Leu, Ser, Phe, Thr or Tyr
<220> FEATURE:
<221> NAME/KEY: misc_feature
<222> LOCATION: (16)..(16)
<223> OTHER INFORMATION: Xaa can be Ala, Glu, Gly, Pro, or Thr
<220> FEATURE:
<221> NAME/KEY: misc_feature
<222> LOCATION: (17)..(17)
```

-continued

```
<223> OTHER INFORMATION: Xaa can be Ala, Glu, Gly, Phe, or Tyr
<220> FEATURE:
<221> NAME/KEY: misc_feature
<222> LOCATION: (18)..(18)
<223> OTHER INFORMATION: Xaa can be Ala, Arg, or Val
<220> FEATURE:
<221> NAME/KEY: misc_feature
<222> LOCATION: (47)..(47)
<223> OTHER INFORMATION: Xaa can be Lys, Thr, Tyr, or Val
<220> FEATURE:
<221> NAME/KEY: misc_feature
<222> LOCATION: (67)..(67)
<223> OTHER INFORMATION: Xaa can be Arg, Ile, Lys, Thr, or an alignment
      gap
<220> FEATURE:
<221> NAME/KEY: misc_feature
<222> LOCATION: (74)..(74)
<223> OTHER INFORMATION: Xaa can be Arg, Thr, Val, or an alignment gap
<220> FEATURE:
<221> NAME/KEY: misc_feature
<222> LOCATION: (75)..(75)
<223> OTHER INFORMATION: Xaa can be Gly, Ser, Thr, Val, or an alignment
      gap
<220> FEATURE:
<221> NAME/KEY: misc_feature
<222> LOCATION: (76)..(76)
<223> OTHER INFORMATION: Xaa can be Gly, Ser, or an alignment gap
<220> FEATURE:
<221> NAME/KEY: misc_feature
<222> LOCATION: (77)..(77)
<223> OTHER INFORMATION: Xaa can be Ala, Arg, Pro, or an alignment gap
<220> FEATURE:
<221> NAME/KEY: misc_feature
<222> LOCATION: (78)..(78)
<223> OTHER INFORMATION: Xaa can be Ala, Thr, or an alignment gap
<220> FEATURE:
<221> NAME/KEY: misc_feature
<222> LOCATION: (79)..(79)
<223> OTHER INFORMATION: Xaa can be Thr, Pro, or an alignment gap
<220> FEATURE:
<221> NAME/KEY: misc_feature
<222> LOCATION: (80)..(80)
<223> OTHER INFORMATION: Xaa can be Ser or an alignment gap
<220> FEATURE:
<221> NAME/KEY: misc_feature
<222> LOCATION: (81)..(81)
<223> OTHER INFORMATION: Xaa can be Arg, Thr, or an alignment gap
<220> FEATURE:
<221> NAME/KEY: misc_feature
<222> LOCATION: (82)..(82)
<223> OTHER INFORMATION: Xaa can be Ser, Thr, or an alignment gap
<220> FEATURE:
<221> NAME/KEY: misc_feature
<222> LOCATION: (84)..(84)
<223> OTHER INFORMATION: Xaa can be Ser, Thr, or an alignment gap
<220> FEATURE:
<221> NAME/KEY: misc_feature
<222> LOCATION: (85)..(85)
<223> OTHER INFORMATION: Xaa can be Gly or an alignment gap
<220> FEATURE:
<221> NAME/KEY: misc_feature
<222> LOCATION: (86)..(86)
<223> OTHER INFORMATION: Xaa can be Gly or an alignment gap
<220> FEATURE:
<221> NAME/KEY: misc_feature
<222> LOCATION: (87)..(87)
<223> OTHER INFORMATION: Xaa can be Val or an alignment gap
<220> FEATURE:
<221> NAME/KEY: misc_feature
<222> LOCATION: (88)..(88)
<223> OTHER INFORMATION: Xaa can be Ser, Thr, Val, or an alignment gap
<220> FEATURE:
<221> NAME/KEY: misc_feature
<222> LOCATION: (91)..(91)
<223> OTHER INFORMATION: Xaa can be Gln, His, Pro, Thr, Ser, or an
      alignment gap
<220> FEATURE:
<221> NAME/KEY: misc_feature
<222> LOCATION: (110)..(110)
<223> OTHER INFORMATION: Xaa can be Ala, Gly, Pro, Tyr, or an alignment
```

```
                                 gap
<220> FEATURE:
<221> NAME/KEY: misc_feature
<222> LOCATION: (112)..(112)
<223> OTHER INFORMATION: Xaa can be Pro or an alignment gap
<220> FEATURE:
<221> NAME/KEY: misc_feature
<222> LOCATION: (113)..(113)
<223> OTHER INFORMATION: Xaa can be Pro or an alignment gap
<220> FEATURE:
<221> NAME/KEY: misc_feature
<222> LOCATION: (114)..(114)
<223> OTHER INFORMATION: Xaa can be Ala, Ser, or an alignment gap
<220> FEATURE:
<221> NAME/KEY: misc_feature
<222> LOCATION: (115)..(115)
<223> OTHER INFORMATION: Xaa can be Ala or an alignment gap
<220> FEATURE:
<221> NAME/KEY: misc_feature
<222> LOCATION: (122)..(122)
<223> OTHER INFORMATION: Xaa can be Glu, Lys, Phe, Tyr, Val, or an
      alignment gap
<220> FEATURE:
<221> NAME/KEY: misc_feature
<222> LOCATION: (144)..(144)
<223> OTHER INFORMATION: Xaa can be Asp, Gly, Pro, Ser, or an alignment
      gap
<220> FEATURE:
<221> NAME/KEY: misc_feature
<222> LOCATION: (145)..(145)
<223> OTHER INFORMATION: Xaa can be Pro or an alignment gap
<220> FEATURE:
<221> NAME/KEY: misc_feature
<222> LOCATION: (171)..(171)
<223> OTHER INFORMATION: Xaa can be Thr or an alignment gap
<220> FEATURE:
<221> NAME/KEY: misc_feature
<222> LOCATION: (172)..(172)
<223> OTHER INFORMATION: Xaa can be Asp, Leu, Ser, Thr, or an alignment
      gap
<220> FEATURE:
<221> NAME/KEY: misc_feature
<222> LOCATION: (175)..(175)
<223> OTHER INFORMATION: Xaa can be Asp, Glu, Gly, Gln, Thr, or an
      alignment gap
<220> FEATURE:
<221> NAME/KEY: misc_feature
<222> LOCATION: (189)..(189)
<223> OTHER INFORMATION: Xaa can be Asn, Asp, Lys, Ser, Thr, or an
      alignment gap
<220> FEATURE:
<221> NAME/KEY: misc_feature
<222> LOCATION: (190)..(190)
<223> OTHER INFORMATION: Xaa can be Asn, Lys, Pro, or an alignment gap
<220> FEATURE:
<221> NAME/KEY: misc_feature
<222> LOCATION: (191)..(191)
<223> OTHER INFORMATION: Xaa can be Pro or an alignment gap
<220> FEATURE:
<221> NAME/KEY: misc_feature
<222> LOCATION: (237)..(237)
<223> OTHER INFORMATION: Xaa can be Ile, Lys, Gln, Thr, Val, or an
      alignment gap
<220> FEATURE:
<221> NAME/KEY: misc_feature
<222> LOCATION: (238)..(238)
<223> OTHER INFORMATION: Xaa can be Ala, Glu, Gln, Ser, Thr, or an
      alignment gap
<220> FEATURE:
<221> NAME/KEY: misc_feature
<222> LOCATION: (263)..(263)
<223> OTHER INFORMATION: Xaa can be Ala, Gln, Pro, or an alignment gap
<220> FEATURE:
<221> NAME/KEY: misc_feature
<222> LOCATION: (340)..(340)
<223> OTHER INFORMATION: Xaa can be Arg, Asn, Gln, Ser, Val, or an
      alignment gap
<220> FEATURE:
<221> NAME/KEY: misc_feature
<222> LOCATION: (361)..(361)
```

```
<223> OTHER INFORMATION: Xaa can be Asn, Glu, His, or an alignment gap
<220> FEATURE:
<221> NAME/KEY: misc_feature
<222> LOCATION: (368)..(368)
<223> OTHER INFORMATION: Xaa can be Ala, Gln, Glu, Gly, Ser, Thr, or an
      alignment gap
<220> FEATURE:
<221> NAME/KEY: misc_feature
<222> LOCATION: (370)..(370)
<223> OTHER INFORMATION: Xaa can be Asn, Arg, Gln, His, or an alignment
      gap
<220> FEATURE:
<221> NAME/KEY: misc_feature
<222> LOCATION: (373)..(373)
<223> OTHER INFORMATION: Xaa can be Pro, Phe, Ser, Trp, or an alignment
      gap
<220> FEATURE:
<221> NAME/KEY: misc_feature
<222> LOCATION: (374)..(374)
<223> OTHER INFORMATION: Xaa can be Asn, Asp, Pro, or an alignment gap
<220> FEATURE:
<221> NAME/KEY: misc_feature
<222> LOCATION: (415)..(415)
<223> OTHER INFORMATION: Xaa can be Asn, Asp, His, Ser, or an alignment
      gap

<400> SEQUENCE: 94

Met Xaa Leu Xaa Xaa Leu Ala Leu Ala Ala Ala Ser Leu Leu Xaa
1               5                   10                  15

Xaa Xaa Gln Ala Gln Ser Ser Val Trp Gly Gln Cys Gly Gly Gln Gly
            20                  25                  30

Trp Ser Gly Pro Thr Thr Cys Ala Ser Gly Ser Thr Cys Val Xaa Leu
        35                  40                  45

Asn Asp Tyr Tyr Ser Gln Cys Leu Pro Gly Ser Ala Ser Ser Thr Thr
    50                  55                  60

Ser Thr Xaa Thr Thr Ser Ser Thr Ser Xaa Xaa Xaa Xaa Xaa Xaa
65                  70                  75                  80

Xaa Xaa Ser Xaa Xaa Xaa Xaa Xaa Thr Thr Xaa Pro Pro Thr Thr Thr
            85                  90                  95

Thr Thr Thr Ser Pro Pro Gly Gly Thr Gly Thr Ala Ser Xaa Ser Xaa
            100                 105                 110

Xaa Xaa Xaa Gly Asn Pro Phe Thr Gly Xaa Gln Leu Trp Ala Asn Pro
        115                 120                 125

Tyr Tyr Ala Ser Glu Val Ala Ser Leu Ala Ile Pro Ser Leu Thr Xaa
    130                 135                 140

Xaa Ala Leu Ala Thr Ala Ala Ala Val Ala Lys Ile Pro Ser Phe
145                 150                 155                 160

Val Trp Leu Asp Thr Val Ala Lys Val Pro Xaa Xaa Leu Gly Xaa Tyr
                165                 170                 175

Leu Ala Asp Ile Arg Ala Ala Asn Lys Ala Gly Gly Xaa Xaa Xaa Tyr
            180                 185                 190

Ala Gly Gln Ile Val Val Tyr Asp Leu Pro Asp Arg Asp Cys Ala Ala
        195                 200                 205

Leu Ala Ser Asn Gly Glu Phe Ser Ile Ala Asn Asn Gly Val Ala Asn
    210                 215                 220

Tyr Lys Asn Tyr Ile Asp Ser Ile Arg Ala Gln Ile Xaa Xaa Tyr Ser
225                 230                 235                 240

Asp Val Arg Thr Ile Leu Val Ile Glu Pro Asp Ser Leu Ala Asn Leu
                245                 250                 255

Val Thr Asn Leu Asn Val Xaa Lys Cys Ala Asn Ala Gln Ser Ala Tyr
            260                 265                 270

Leu Glu Cys Val Asn Tyr Ala Leu Thr Gln Leu Asn Leu Pro Asn Val
```

```
                    275                 280                 285
Ala Met Tyr Leu Asp Ala Gly His Ala Gly Trp Leu Gly Trp Pro Ala
    290                 295                 300

Asn Leu Ser Pro Ala Ala Gln Leu Phe Ala Asn Val Tyr Lys Asn Ala
305                 310                 315                 320

Ser Ser Pro Arg Ala Leu Arg Gly Leu Ala Thr Asn Val Ala Asn Tyr
                325                 330                 335

Asn Ala Trp Xaa Ile Ser Ser Pro Pro Ser Tyr Thr Gln Gly Asn Ala
                340                 345                 350

Asn Tyr Asp Glu Lys Leu Tyr Ile Xaa Ala Leu Ala Pro Leu Leu Xaa
            355                 360                 365

Asn Xaa Gly Trp Xaa Xaa Ala His Phe Ile Val Asp Gln Gly Arg Ser
    370                 375                 380

Gly Val Gln Pro Thr Arg Gln Gln Gln Trp Gly Asp Trp Cys Asn Val
385                 390                 395                 400

Ile Gly Thr Gly Phe Gly Ile Arg Pro Thr Thr Asn Thr Gly Xaa Ser
                405                 410                 415

Leu Ile Asp Ala Phe Val Trp Val Lys Pro Gly Gly Glu Cys Asp Gly
            420                 425                 430

Thr Ser Asn Ser Ser Ala Pro Arg Tyr Asp Ser His Cys Gly Leu Pro
                435                 440                 445

Asp Ala Leu Gln Pro Ala Pro Glu Ala Gly Thr Trp Phe Gln Ala Tyr
            450                 455                 460

Phe Glu Gln Leu Leu Thr Asn Ala Asn Pro Ala Leu
465                 470                 475

<210> SEQ ID NO 95
<211> LENGTH: 447
<212> TYPE: PRT
<213> ORGANISM: Humicola jecorina

<400> SEQUENCE: 95

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
```

```
                180                 185                 190
Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
        435                 440                 445
```

VARIANT *HYPOCREA JECORINA* CBH2 CELLULASES

CROSS-REFERENCE TO RELATED APPLICATIONS

The present application is a divisional application of U.S. patent application Ser. No. 11/317,110, filed Dec. 22, 2005, which is now U.S. Pat. No. 8,008,056, which claims priority to U.S. Provisional Patent Application No. 60/640,398, filed Dec. 30, 2004 and U.S. Provisional Patent Application No. 60/656,863, filed Feb. 25, 2005, the disclosures of which are hereby incorporated by reference in their entirety.

STATEMENT AS TO RIGHTS TO INVENTIONS MADE UNDER FEDERALLY SPONSORED RESEARCH AND DEVELOPMENT

Portions of this work were funded by Subcontract No. ZCO-0-30017-01 with the National Renewable Energy Laboratory under Prime Contract No. DE-AC36-99GO10337 with the U.S. Department of Energy. Accordingly, the United States Government may have certain rights in this invention.

SEQUENCE LISTING

The sequence listing submitted via EFS, in compliance with 37 C.F.R. §1.52(e), is incorporated herein by reference. The sequence listing text file submitted via EFS contains the file "30864D1_seqlist.txt" created on Jun. 29, 2011, which is 67.717 bytes in size.

FIELD OF THE INVENTION

The present invention relates to variant cellobiohydrolase enzymes and isolated nucleic acid sequences which encode polypeptides having cellobiohydrolase activity. The invention also relates to nucleic acid constructs, vectors, and host cells comprising the nucleic acid sequences as well as methods for producing recombinant variant CBH polypeptides.

REFERENCES

1. Sheehan and Himmel *Biotechnology Progress* 15, pp 817-827 (1999)
2. Matti Linko Proceedings of the Second TRICEL Symposium on *Trichoderma reesei* Cellulases and Other Hydrolases pp 9-11 (1993)
3. Tuula T. Teeri *Trends in Biotechnology* 15, pp 160-167 (1997)
4. T. T. Teeri et al. Spec. Publ.-R. Soc. Chem., 246 (Recent Advances in Carbohydrate Bioengineering), pp 302-308. (1999)
5. PDB reference 1QK2 (Cel6A=CBH2) J.-Y. Zou, G. J. Kleywegt, J. Stahlberg, H. Drigues, W. Nerinckx, M. Claeyssens, A. Koivula, T. T. Teeri, T. A Jones, *Structure* (LONDON), V. 7 p. 1035 (1999)
6. PDB reference 2BVW Structural changes of the active site tunnel of *Humicola insolens* cellobiohydrolase, Cel6A, upon oligosaccharide binding, Varrot A, Schulein M, Davies G J, Biochemistry 1999 Jul. 13; 38(28):8884-91.
7. PDB reference 1DYS Structure and function of *Humicola insolens* family 6 cellulases: structure of the endoglucanase, Cel6B, at 1.6 A resolution, Davies G J, Brzozowski A M, Dauter M, Varrot A, Schulein M, Biochem J 2000 May 15; 348 Pt 1:201-7.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., J. Biol. Chem., vol. 276, no. 26, pp. 24309-24314, Jun. 29, 2001). As the limits of non-renewable resources approach, the potential of cellulose to become a major renewable energy resource is enormous (Krishna et al., Bioresource Tech. 77:193-196, 2001). The effective utilization of cellulose through biological processes is one approach to overcoming the shortage of foods, feeds, and fuels (Ohmiya et al., Biotechnol. Gen. Engineer. Rev. vol. 14, pp. 365-414, 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., TIBTECH 5, 255-261, 1987; Schiilein, Methods Enzymol., 160, 25, pp. 234-243, 1988). Endoglucanases act mainly on the amorphous parts of the cellulose fibre, whereas cellobiohydrolases are also able to degrade crystalline cellulose (Nevalainen and Penttilä, Mycota, 303-319, 1995). Thus, the presence of a cellobiohydrolase in a cellulase system is required for efficient solubilization of crystalline cellulose (Suurnakki, et al. Cellulose 7:189-209, 2000). Beta-glucosidase acts to liberate D-glucose units from cellobiose, cello-oligosaccharides, and other glucosides (Freer, J. Biol. Chem. vol. 268, no. 13, pp. 9337-9342, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. See, e.g., Aro et al., 2001; Biochemistry and Genetics of Cellulose Degradation, eds. Aubert, J. P. et al., Academic Press, 1988; Wood et al., Methods in Enzymology, vol. 160, no. 9, pp. 87-116, 1988, and Coughlan, et al., "Comparative Biochemistry of Fungal and Bacterial Cellulolytic Enzyme Systems" Biochemistry and Genetics of Cellulose Degradation, pp. 11-30 1988.

The fungal cellulase classifications of CBH, EG and BG can be further expanded to include multiple components within each classification. For example, multiple CBHs, EGs and BGs have been isolated from a variety of fungal sources including *Trichoderma reesei* (also referred to as *Hypocrea jecorina*) which contains known genes for 2 CBHs, i.e., CBH I ("CBH1") and CBH II ("CBH2"), at least 8 EGs, i.e., EG I, EG II, EG III, EGIV, EGV, EGVI, EGVII and EGVIII, and at least 5 BGs, i.e., BG1, BG2, BG3, BG4 and BG5. EGIV, EGVI and EGVIII also have xyloglucanase activity.

In order to efficiently convert crystalline cellulose to glucose the complete cellulase system comprising components from each of the CBH, EG and BG classifications is required, with isolated components less effective in hydrolyzing crystalline cellulose (Filho et al., Can. J. Microbiol. 42:1-5, 1996). A synergistic relationship has been observed between cellulase components from different classifications. In particular, the EG-type cellulases and CBH— type cellulases synergistically interact to more efficiently degrade cellulose. See, e.g., Wood, Biochemical Society Transactions, 611th Meeting, Galway, vol. 13, pp. 407-410, 1985.

Cellulases are known in the art to be useful in the treatment of textiles for the purposes of enhancing the cleaning ability of detergent compositions, for use as a softening agent, for improving the feel and appearance of cotton fabrics, and the like (Kumar et al., Textile Chemist and Colorist, 29:37-42, 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,358,599; The Shizuoka Prefectural Hammamatsu Textile Industrial Research Institute Report, Vol. 24, pp. 54-61, 1986), have been described.

Hence, cellulases produced in fungi and bacteria have received significant attention. In particular, fermentation of *Trichoderma* spp. (e.g., *Trichoderma longibrachiatum* or *Trichoderma reesei*) has been shown to produce a complete cellulase system capable of degrading crystalline forms of cellulose.

Although cellulase compositions have been previously described, there remains a need for new and improved cellulase compositions for use in household detergents, stone-washing compositions or laundry detergents, etc. Cellulases that exhibit improved performance are of particular interest.

BRIEF SUMMARY OF THE INVENTION

The invention provides an isolated cellulase protein, identified herein as variant CBH2, and nucleic acids which encode a variant CBH2.

In one embodiment the invention is directed to a variant CBH2 cellulase, wherein said variant comprises a substitution or deletion at a position corresponding to one or more of residues V94, P98, G118, M120, M134, T142, L144, M145, T148, T154, L179, Q204, V206, S210, I212, T214, L215, G231, T232, V250, Q276, N285, S291, G308, T312, S316, V323, N325, I333, G334, S343, T349, G360, S380, A381, S386, F411, S413, A416, Q426 and/or A429 in CBH2 from *Hypocrea jecorina* (SEQ ID NO: 95). In a first aspect, the invention encompasses a variant CBH2 cellulase, wherein said variant comprises a substitution or deletion at a position corresponding to one or more of residues V94E, P98L, G118P, M120L, M134G/L/V, T142V, L144G/R/S, M145L, T148Y, T154A, L179A, Q204E, V206L, S210L/R, I212V, T214M/Y, L215I, G231N, T232V, V250I, Q276L, N285Q, S291G, G308A, T312S, S316P, V323L/N/Y, N325D, I333L, G334A, S343P, T349L/V, G360R, S380T, A381T, S386P, F411Y, S413Y, A416G, Q426E and/or A429T in CBH2 from *Hypocrea jecorina* (SEQ ID NO: 95).

In a second embodiment the invention is directed to a variant CBH2 cellulase, wherein said variant comprises a substitution or deletion at a position corresponding to one or more of residues V94, P98, G118, M120, M134, T142, M145, T148, T154, L179, Q204, V206, I212, L215, G231, T232, V250, Q276, N285, S291, G308, T312, S316, V323, N325, I333, G334, S343, T349, G360, S380, A381, S386, F411, S413, A416, Q426 and/or A429 in CBH2 from *Hypocrea jecorina* (SEQ ID NO: 95). In a first aspect, the invention encompasses a variant CBH2 cellulase, wherein said variant comprises a substitution or deletion at a position corresponding to one or more of residues V94E, P98L, G118P, M120L, M134V, T142V, M145L, T148Y, T154A, L179A, Q204E, V206L, I212V, L215I, G231N, T232V, V250I, Q276L, N285Q, S291G, G308A, T312S, S316P, V323N, N325D, I333L, G334A, S343P, T349L, G360R, S380T, A381T, S386P, F411Y, S413Y, A416G, Q426E and/or A429T in CBH2 from *Hypocrea jecorina* (SEQ ID NO: 95).

In a third embodiment, the invention encompasses a variant CBH2 cellulase, wherein said variant comprises a substitution or deletion at a position corresponding to one or more of residues P98, M134, V206, I212, T312, S316, F411 and/or S413 in CBH2 from *Hypocrea jecorina* (SEQ ID NO: 95). In a first aspect, the invention encompasses a variant CBH2 cellulase, wherein said variant comprises a substitution or deletion at a position corresponding to one or more of residues P98L, M134G/L/V, V206L, I212V, T312S, S316P, F411Y and/or S413Y in CBH2 from *Hypocrea jecorina* (SEQ ID NO: 95).

In a fourth embodiment, the invention encompasses a variant CBH2 cellulase, wherein said variant comprises a substitution or deletion at a position corresponding to one or more residues in a spatial region and said spatial region is selected from the group consisting of (210, 214), (253, 255, 257, 258), (411, 413, 415), (412, 414, 416), (312, 313), 323, (212, 149, 152), (134, 144) and 98 in CBH2 from *Hypocrea jecorina* (SEQ ID NO: 95). In a first aspect, the invention encompasses a variant CBH2 cellulase, wherein said variant is selected from the group consisting of S316P/V323L, S316P/V323Y, V206L/S210R/S316P, V206L/S316P, V206L/S210L/T214M/S316P, V206L/S210R/T214Y/S316P, M134G/L144G/S316P, M134L/L144R/S316P and M134L/L144S/S316P in CBH2 from *Hypocrea jecorina* (SEQ ID NO: 95).

In a fifth embodiment, the invention encompasses a variant CBH2 cellulase, wherein said variant comprises a substitution or deletion at a position corresponding to one or more of residues P98, M134, L144, V206, S210, T214, S316, V323 and/or S413 in CBH2 from *Hypocrea jecorina* (SEQ ID NO: 95). In a first aspect, the invention encompasses a variant CBH2 cellulase, wherein said variant comprises a substitution or deletion at a position corresponding to one or more of residues P98L, M134L/V, L144R, V206L, S210L/R, T214Y, S316P, V323Y and/or S413Y in CBH2 from *Hypocrea jecorina* (SEQ ID NO: 95). In a second aspect, the invention encompasses a variant CBH2 cellulase, wherein said variant is selected from the group consisting of 98L/134V/206L/210R/214Y/316P/413Y, 98L/134L/144R/316P/413Y, 98L/134L/144R/206L/210R/214Y/316P/413Y, 98L/134V/316P/323Y/413Y, 98L/134V/206L/210R/214Y/316P/323Y/413Y, 98L/134L/144R/316P/323Y/413Y, 98L/134L/144R/206L/210R/214Y/316P/323Y/413Y, 98L/134L/144R/210R/214Y/316P/323Y/413Y and 98L/134L/144R/210L/214Y/316P/323Y/413Y in CBH2 from *Hypocrea jecorina* (SEQ ID NO: 95).

In a sixth embodiment, the invention encompasses an isolated nucleic acid encoding a polypeptide having cellobiohydrolase activity.

In a first aspect, the invention encompasses an isolated nucleic acid encoding a polypeptide having cellobiohydrolase activity, which polypeptide is a variant of a glycosyl hydrolase of family 6, and wherein said nucleic acid encodes a substitution at a residue which is sensitive to temperature stress in the polypeptide encoded by said nucleic acid, wherein said variant cellobiohydrolase is derived from *H. jecorina* cellobiohydrolase. In a second aspect, the invention encompasses an isolated nucleic acid encoding a polypeptide having cellobiohydrolase activity, which polypeptide is a variant of a glycosyl hydrolase of family 6, and wherein said nucleic acid encodes a substitution at a residue which is effects enzyme processitivity in the polypeptide encoded by said nucleic acid, wherein said variant cellobiohydrolase is derived from *H. jecorina* cellobiohydrolase. In a third aspect, the invention encompasses an isolated nucleic acid encoding a polypeptide having cellobiohydrolase activity, which polypeptide is a variant of a glycosyl hydrolase of family 6, and wherein said nucleic acid encodes a substitution at a residue which effects product inhibition in the polypeptide encoded by said nucleic acid, wherein said variant cellobiohydrolase is derived from *H. jecorina* cellobiohydrolase.

In another aspect the invention is directed to an isolated nucleic acid encoding a variant CBH2 cellulase, wherein said variant comprises a substitution at a position corresponding to one or more of residues V94, P98, G118, M120, M134, T142, M145, T148, T154, L179, Q204, V206, I212, L215, G231, T232, V250, Q276, N285, S291, G308, T312, S316, V323, N325, I333, G334, S343, T349, G360, S380, A381, S390, F411, S413, A416, Q426 and/or A429 in CBH2 from *Hypocrea jecorina* (SEQ ID NO: 2).

In an seventh embodiment the invention is directed to an expression cassette comprising a nucleic acid encoding a variant CBH2. In one aspect there is a construct comprising the nucleic acid of encoding the variant CBH2 operably linked to a regulatory sequence.

In an eighth embodiment the invention is directed to a vector comprising a nucleic acid encoding a variant CBH2. In one aspect there is a construct comprising the nucleic acid of encoding the variant CBH2 operably linked to a regulatory sequence.

In a ninth embodiment the invention is directed to a host cell transformed with the vector comprising a nucleic acid encoding a CBH2 variant.

In a tenth embodiment the invention is directed to a method of producing a CBH2 variant comprising the steps of:
(a) culturing a host cell transformed with the vector comprising a nucleic acid encoding a CBH2 variant in a suitable culture medium under suitable conditions to produce CBH2 variant;
(b) obtaining said produced CBH2 variant.

In an eleventh embodiment the invention is directed to a detergent composition comprising a surfactant and a CBH2 variant. In one aspect of this embodiment the detergent is a laundry detergent. In a second aspect of this embodiment the detergent is a dish detergent. In third aspect of this invention, the variant CBH2 cellulase is used in the treatment of a cellulose containing textile, in particular, in the stonewashing or indigo dyed denim.

In a twelfth embodiment the invention is directed to a feed additive comprising a CBH2 variant.

In a thirteenth embodiment the invention is directed to a method of treating wood pulp comprising contacting said wood pulp with a CBH2 variant.

In a fourteenth embodiment the invention is directed to a method of converting biomass to sugars comprising contacting said biomass with a CBH2 variant.

In an embodiment, the cellulase is derived from a fungus, bacteria or Actinomycete. In one aspect, the cellulase is derived from a fungus. In another aspect, the fungus is a filamentous fungus. It is preferred the filamentous fungus belong to Euascomycete, in particular, *Aspergillus* spp., *Gliocladium* spp., *Fusarium* spp., *Acremonium* spp., *Myceliophtora* spp., *Verticillium* spp., *Myrothecium* spp., or *Penicillium* spp. In a further aspect of this embodiment, the cellulase is a cellobiohydrolase.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 is the amino acid (SEQ ID NO: 2) sequence of the wild type Cel6A (CBH2) from *H. jecorina*. Amino acids 1-24 correspond to the signal peptide.

FIG. 2 is the nucleic acid (SEQ ID NO: 1) sequence of the wild type *H. jecorina* CBH2.

FIG. 3 shows the amino acid alignment of the Cel6 family members for which there were crystal structures available. The sequences are:—*Humicola insolens* CBH2, *Acremonium* CBH2, *Agaricus* CBH2, *Fusarium oxysporum* CBH2, *Hypocrea koningii* CBH2, *Phanerochaete chrysosporum* CBH2, *Talaromyces emersonii* CBH2, *T. reesei* (i.e., *Hypocrea jecorina* CBH2, and the consensus sequence. Alignment has been done by Clustal W with a gap penalty of 10 using Vector NTI Suite software program.

FIG. 4 is the pRAX1 vector. This vector is based on the plasmid pGAPT2 except a 5259 bp HindIII fragment of *Aspergillus nidulans* genomic DNA fragment AMA1 sequence (Aleksenko and Clutterbuck, Molecular Microbiology 1996 19:565-574) was inserted. Base 1 to 1134 contains *Aspergillus niger* glucoamylase gene promoter. Base 3098 to 3356 and 4950 to 4971 contains *Aspergillus niger* glucoamylase terminator. *Aspergillus nidulans* pyrG gene was inserted from 3357 to 4949 as a marker for fungal transformation. There is a multiple cloning site (MCS) into which genes may be inserted.

FIG. 5 is the pRAXdes2 vector backbone. This vector is based on the plasmid vector pRAX1. A Gateway cassette has been inserted into pRAX1 vector (indicated by the arrow on the interior of the circular plasmid). This cassette contains recombination sequence attR1 and attR2 and the selection marker catH and ccdB. The vector has been made according to the manual given in Gateway™ Cloning Technology: version 1 page 34-38 and can only replicate in *E. coli* DB3.1 from Invitrogen; in other *E. coli* hosts the ccdB gene is lethal. First a PCR fragment is made with primers containing attB1/2 recombination sequences. This fragment is recombined with pDONR201 (commercially available from Invitrogen); this vector contains attP1/2 recombination sequences with catH and ccdB in between the recombination sites. The BP clonase enzymes from Invitrogen are used to recombine the PCR fragment in this so-called ENTRY vector, clones with the PCR fragment inserted can be selected at 50 μg/ml kanamycin because clones expressing ccdB do not survive. Now the att sequences are altered and called attL1 and attL2. The second step is to recombine this clone with the pRAXdes2 vector (containing attR1 and attR2 catH and ccdB in between the recombination sites). The LR clonase enzymes from Invitrogen are used to recombine the insert from the ENTRY vector in the destination vector. Only pRAXCBH2 vectors are selected using 100 μg/ml ampicillin because ccdB is lethal and the ENTRY vector is sensitive to ampicillin. By this method the expression vector is now prepared and can be used to transform *A. niger*.

FIG. 6 provides an illustration of the pRAXdes2cbh2 vector which was used for expression of the nucleic acids encoding the CBH2 variants in *Aspergillus*. A nucleic acid encoding a CBH2 enzyme homolog or variant was cloned into the vector by homologous recombination of the att sequences.

FIG. 7 provides an illustration of the pENTRY-CBH2 vector.

DETAILED DESCRIPTION

Figure 8:
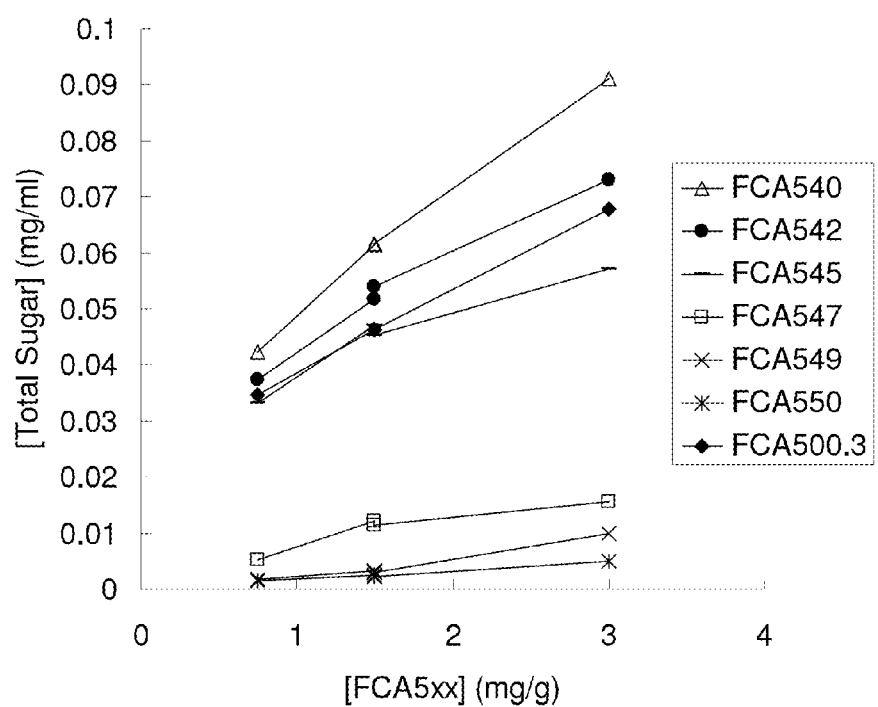
FIG. 8 is a graph of the dose dependent release of sugars from phosphoric acid swollen cellulose by different variants. The variants display a wide range of activity on this substrate.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., MOLECULAR CLONING: A LABORATORY MANUAL (Second Edition), Cold Spring Harbor Press, Plainview, N.Y., 1989, and Ausubel F M et al., Current Protocols in Molecular Biology, John Wiley & Sons, New York, N.Y., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. DEFINITIONS

The term "polypeptide" as used herein refers to a compound made up of a single chain of amino acid residues linked by peptide bonds. The term "protein" as used herein may be synonymous with the term "polypeptide".

"Variant" means a protein which is derived from a precursor protein (e.g., the native protein) by addition of one or more amino acids to either or both the C- and N-terminal end, substitution of one or more amino acids at one or a number of different sites in the amino acid sequence, or deletion of one or more amino acids at either or both ends of the protein or at one or more sites in the amino acid sequence. The preparation of an enzyme variant is preferably achieved by modifying a DNA sequence which encodes for the native protein, transformation of the modified DNA sequence into a suitable host, and expression of the modified DNA sequence to form the variant enzyme. The variant CBH2 enzyme of the invention includes peptides comprising altered amino acid sequences in comparison with a precursor enzyme amino acid sequence wherein the variant CBH2 enzyme retains the characteristic cellulolytic nature of the precursor enzyme but which may have altered properties in some specific aspect. For example, a variant CBH2 enzyme may have an increased pH optimum or increased temperature or oxidative stability but will retain its characteristic cellulolytic activity. It is contemplated that the variants according to the present invention may be derived from a DNA fragment encoding a cellulase variant CBH2 enzyme wherein the functional activity of the expressed cellulase variant is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained. The terms variant and derivative may be used interchangeably herein.

"Equivalent residues" may also be defined by determining homology at the level of tertiary structure for a precursor cellulase whose tertiary structure has been determined by x-ray crystallography. Equivalent residues are defined as those for which the atomic coordinates of two or more of the main chain atoms of a particular amino acid residue of a cellulase and *Hypocrea jecorina* CBH2 (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the *H. jecorina* CBH2. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *H. jecorina* CBH2 are defined as those amino acids of a cellulase which may adopt a conformation such that they either alter, modify or contribute to protein structure, substrate binding or catalysis in a manner defined and attributed to a specific residue of the *H. jecorina* CBH2. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *H. jecorina* CBH2. The crystal structure of *H. jecorina* CBH2 is shown in Zou et al. (1999) (Ref. 5, supra).

The term "nucleic acid molecule" includes RNA, DNA and cDNA molecules. It will be understood that, as a result of the degeneracy of the genetic code, a multitude of nucleotide sequences encoding a given protein such as CBH2 and/or variants thereof may be produced. The present invention contemplates every possible variant nucleotide sequence, encoding variant CBH2, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring, for example, antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode the variant CBH2 will hybridize, under moderate to high stringency conditions to the wild type sequence provided herein as SEQ ID NO:1. However, in some cases a CBH2-encoding nucleotide sequence is employed that possesses a substantially different codon usage, while the protein encoded by the CBH2-encoding nucleotide sequence has the same or substantially the same amino acid sequence as the native protein. For example, the coding sequence may be modified to facilitate faster expression of CBH2 in a particular prokaryotic or eukaryotic expression system, in accordance with the frequency with which a particular codon is utilized by the host. Te'o, et al. (FEMS Microbiology Letters 190:13-19, 2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° C. below the Tm of the probe); "high stringency" at about 5-10° C. below the Tm; "moderate" or "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "CBH2 expression" refers to transcription and translation of the cbh2 gene or variants thereof, the products of which include precursor RNA, mRNA, polypeptide, post-translationally processed polypeptides, and derivatives thereof, including CBH2 from related species such as *Trichoderma koningii, Hypocrea jecorina* (also known as *Trichoderma longibrachiatum, Trichoderma reesei* or *Trichoderma viride*) and *Hypocrea schweinitzii*. By way of example, assays for CBH2 expression include Western blot for CBH2 protein, Northern blot analysis and reverse transcriptase polymerase chain reaction (RT-PCR) assays for cbh2 mRNA, and Phosphoric Acid Swollen Cellulose and PAHBAH assays as described in the following: (a) PASC: (Karlsson, J. et al. (2001), Eur. J. Biochem, 268, 6498-6507, Wood, T. (1988) in Methods in Enzymology, Vol. 160. Biomass Part a Cellulose and Hemicellulose (Wood, W. & Kellog, S. Eds.), pp. 19-25, Academic Press, San Diego, Calif., USA) and (b) PAHBAH: (Lever, M. (1972) Analytical Biochemistry, 47, 273, Blakeney, A. B. & Mutton, L. L. (1980) Journal of Science of Food and Agriculture, 31, 889, Henry, R. J. (1984) Journal of the Institute of Brewing, 90, 37).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein that facilitates the secretion of the mature form of the protein outside the cell. The mature form of the extracellular protein lacks the signal sequence that is cleaved off during the secretion process.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*. It has now been demonstrated that the asexual industrial fungus *Trichoderma reesei* is a clonal derivative of the ascomycete *Hypocrea jecorina*. See Kuhls et al., PNAS (1996) 93:7755-7760.

The term "cellooligosaccharide" refers to oligosaccharide groups containing from 2-8 glucose units and having β-1,4 linkages, e.g., cellobiose.

The term "cellulase" refers to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

CBH2 from *Hypocrea jecorina* is a member of the Glycosyl Hydrolase Family 6 (hence Cel6) and, specifically, was the first member of that family identified in *Hypocrea jecorina* (hence Cel6A). The Glycosyl Hydrolase Family 6 contains both Endoglucanases and Cellobiohydrolases/exoglucanases, and that CBH2 is the latter. Thus, the phrases CBH2, CBH2-type protein and Cel6 cellobiohydrolases may be used interchangeably herein.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity. Cellulose binding domain and cellulose binding module may be used interchangeably herein.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the cbh2 gene" means that either that the cbh2 gene has been deleted from the genome and therefore cannot be expressed by the recombinant host microorganism; or that the cbh2 gene or transcript has been modified such that a functional CBH2 enzyme is not produced by the host microorganism.

The term "variant cbh2 gene" or "variant CBH2" means, respectively, that the nucleic acid sequence of the cbh2 gene from *H. jecorina* has been altered by removing, adding, and/or manipulating the coding sequence or the amino acid sequence of the expressed protein has been modified consistent with the invention described herein.

As used herein, the term "purifying" generally refers to subjecting transgenic nucleic acid or protein containing cells to biochemical purification and/or column chromatography.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

As used herein, the term "enriched" means that the CBH2 is found in a concentration that is greater relative to the CBH2 concentration found in a wild-type, or naturally occurring, fungal cellulase composition. The terms enriched, elevated and enhanced may be used interchangeably herein.

A wild type fungal cellulase composition is one produced by a naturally occurring fungal source and which comprises one or more BGL, CBH and EG components wherein each of these components is found at the ratio produced by the fungal source. Thus, an enriched CBH composition would have CBH at an altered ratio wherein the ratio of CBH to other cellulase components (i.e., EGs, beta-glucosidases and other endoglucanases) is elevated. This ratio may be increased by either increasing CBH or decreasing (or eliminating) at least one other component by any means known in the art.

The term "isolated" or "purified" as used herein refers to a nucleic acid or amino acid that is removed from at least one component with which it is naturally associated.

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified CBH may then be added to the enzymatic solution resulting in an enriched CBH solution. It is also possible to elevate the amount of CBH produced by a microbe using molecular genetics methods to overexpress the gene encoding CBH, possibly in conjunction with deletion of one or more genes encoding other cellulases.

Fungal cellulases may contain more than one CBH component. The different components generally have different isoelectric points which allow for their separation via ion exchange chromatography and the like. Either a single CBH component or a combination of CBH components may be employed in an enzymatic solution.

When employed in enzymatic solutions, the homolog or variant CBH2 component is generally added in an amount sufficient to allow the highest rate of release of soluble sugars from the biomass. The amount of homolog or variant CBH2 component added depends upon the type of biomass to be saccharified, which can be readily determined by the skilled artisan. when employed, the weight percent of the homolog or variant CBH2 component present in the cellulase composition is from preferably between 1 and 100 with illustrative examples being about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 60 weight percent, from about 15 to about 65 weight percent, from about 15 to about 70 weight percent, from about 15 to about 75 weight percent, from about 15 to about 80 weight percent, from about 15 to about 85 weight percent, from about 15 to about 95 weight percent. However, when employed, the weight percent of the homolog or variant CBH2 component relative to any EG type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. HOST ORGANISMS

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum, Trichoderma viride, Trichoderma koningii, Trichoderma harzianum; Penicillium* sp.; *Humicola* sp., including *Humicola insolens* and *Humicola grisea; Chrysosporium* sp., including *C. lucknowense; Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus*, or *Aspergillus nidulans* cell.

In another preferred embodiment, the filamentous fungal parent cell is a *Trichoderma reesei* cell.

III. CELLULASES

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., TIBTECH 5, 255-261, 1987; Schulein, 1988).

Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl β-D-glucosides such as methyl β-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Cellulases also find a number of uses in detergent compositions including to enhance cleaning ability, as a softening agent and to improve the feel of cotton fabrics (Hemmpel, ITB Dyeing/Printing/Finishing 3:5-14, 1991; Tyndall, Textile Chemist and Colorist 24:23-26, 1992; Kumar et al., Textile Chemist and Colorist, 29:37-42, 1997). While the mechanism is not part of the invention, softening and color restoration properties of cellulase have been attributed to the alkaline endoglucanase components in cellulase compositions, as exemplified by U.S. Pat. Nos. 5,648,263, 5,691,178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776,757).

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al., In Proc. Tappi Pulping Conf., Nashville, Tenn., 27-31, pp. 693-696, 1996), for use as a feed additive (WO 91/04673) and in grain wet milling.

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., .FEBS Lett. 204:223-227, 1986; Tomme et al., Eur. J. Biochem. 170:575-581, 1988). The CBDs are particularly important in the hydrolysis of crystalline cellulose. It has been shown that the ability of cellobiohydrolases to degrade crystalline cellulose clearly decreases when the CBD is absent (Linder and Teeri, J. Biotechnol. 57:15-28, 1997). However, the exact role and action mechanism of CBDs is still a matter of speculation. It has been suggested that the CBD enhances the enzymatic activity merely by increasing the effective enzyme concentration at the surface of cellulose (Stahlberg et al., Bio/Technol. 9:286-290, 1991), and/or by loosening single cellulose chains from the cellulose surface (Tormo et al., EMBO J. vol. 15, no. 21, pp. 5739-5751, 1996). Most studies concerning the effects of cellulase domains on different substrates have been carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei*: Shoemaker, S. et al., Bio/Technology, 1:691-696, 1983, which discloses CBH1; Teeri, T. et al., Gene, 51:43-52, 1987, which discloses CBH2. Cellulases from species other than *Trichoderma* have also been described e.g., Ooi et al., Nucleic Acids Research, vol. 18, no. 19, 1990, which discloses the cDNA sequence coding for endoglucanase F1-CMC produced by *Aspergillus aculeatus*; Kawaguchi T et al., Gene 173(2):287-8, 1996, which discloses the cloning and sequencing of the cDNA encoding beta-glucosidase 1 from *Aspergillus aculeatus*; Sakamoto et al., Curr. Genet. 27:435-439, 1995, which discloses the cDNA sequence encoding the endoglucanase CMCase-1 from *Aspergillus kawachii* IFO 4308; Saarilahti et al., Gene 90:9-14, 1990, which discloses an endoglucanase from *Erwinia carotovara*; Spilliaert R, et al., Eur J. Biochem. 224 (3):923-30, 1994, which discloses the cloning and sequencing of bglA, coding for a thermostable beta-glucanase from *Rhodothermus marinus*; and Halldorsdottir S et al., Appl Microbiol Biotechnol. 49(3):277-84, 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type, EG-type and BG-type cellulases is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-ethanol production); and/or (3) in feed compositions.

IV. MOLECULAR BIOLOGY

In one embodiment this invention provides for the expression of variant cbh2 genes under control of a promoter functional in a filamentous fungus. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

Methods for Identifying Homologous cbh2 Genes

The nucleic acid sequence for the wild type *H. jecorina* CBH2 is shown in FIG. 1. The invention, in one aspect, encompasses a nucleic acid molecule encoding a CBH2 homolog described herein. The nucleic acid may be a DNA molecule.

Techniques that can be used to isolate CBH2-encoding DNA sequences are well known in the art and include, but are not limited to, cDNA and/or genomic library screening with a homologous DNA probe and expression screening with activity assays or antibodies against CBH2. Any of these methods can be found in Sambrook, et al. or in CURRENT PROTOCOLS IN MOLECULAR BIOLOGY, F. Ausubel, et al., ed. Greene Publishing and Wiley-Interscience, New York (1987) ("Ausubel").

Methods of Mutating cbh2 Nucleic Acid Sequences

Any method known in the art that can introduce mutations is contemplated by the present invention.

The present invention relates to the expression, purification and/or isolation and use of variant CBH2. These enzymes are preferably prepared by recombinant methods utilizing the cbh2 gene from *H. jecorina*. The fermentation broth may be used with or without purification.

After the isolation and cloning of the cbh2 gene from *H. jecorina*, other methods known in the art, such as site directed mutagenesis, are used to make the substitutions, additions or deletions that correspond to substituted amino acids in the expressed CBH2 variant. Again, site directed mutagenesis and other methods of incorporating amino acid changes in expressed proteins at the DNA level can be found in Sambrook, et al. and Ausubel, et al.

DNA encoding an amino acid sequence variant of the *H. jecorina* CBH2 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *H. jecorina* CBH2.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488

(1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *H. jecorina* CBH2. See Higuchi, in PCR Protocols, pp. 177-183 (Academic Press, 1990); and Vallette et al., Nuc. Acids Res. 17:723-733 (1989). See, also, for example Cadwell et al., PCR Methods and Applications, Vol 2, 28-33 (1992). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a variant CBH 2 can be determined, and a nucleic acid sequence encoding such amino acid sequence variant can be generated synthetically.

The variant CBH2(s) so prepared may be subjected to further modifications, oftentimes depending on the intended use of the cellulase. Such modifications may involve further alteration of the amino acid sequence, fusion to heterologous polypeptide(s) and/or covalent modifications.

V. cbh2 NUCLEIC ACIDS AND CBH2 POLYPEPTIDES

A. Variant cbh2-Type Nucleic Acids

The nucleic acid sequence for the wild type *H. jecorina* cbh2 is shown in FIG. 1. The invention encompasses a nucleic acid molecule encoding the variant cellulases described herein. The nucleic acid may be a DNA molecule.

After the isolation and cloning of the cbh2, other methods known in the art, such as site directed mutagenesis, are used to make the substitutions, additions or deletions that correspond to substituted amino acids in the expressed CBH2 variant. Again, site directed mutagenesis and other methods of incorporating amino acid changes in expressed proteins at the DNA level can be found in Sambrook, et al. and Ausubel, et al.

After DNA sequences that encode the CBH2 variants have been cloned into DNA constructs, the DNA is used to transform microorganisms. The microorganism to be transformed for the purpose of expressing a variant CBH2 according to the present invention may advantageously comprise a strain derived from *Trichoderma* sp. Thus, a preferred mode for preparing variant CBH2 cellulases according to the present invention comprises transforming a *Trichoderma* sp. host cell with a DNA construct comprising at least a fragment of DNA encoding a portion or all of the variant CBH2. The DNA construct will generally be functionally attached to a promoter. The transformed host cell is then grown under conditions so as to express the desired protein. Subsequently, the desired protein product may be purified to substantial homogeneity.

However, it may in fact be that the best expression vehicle for a given DNA encoding a variant CBH2 may differ from *H. jecorina*. Thus, it may be that it will be most advantageous to express a protein in a transformation host that bears phylogenetic similarity to the source organism for the variant CBH2. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of a *Aspergillus* spp. expression system is provided for illustrative purposes only and as one option for expressing the variant CBH2 of the invention. One of skill in the art, however, may be inclined to express the DNA encoding variant CBH2 in a different host cell if appropriate and it should be understood that the source of the variant CBH2 should be considered in determining the optimal expression host. Additionally, the skilled worker in the field will be capable of selecting the best expression system for a particular gene through routine techniques utilizing the tools available in the art.

B. Variant CBH2 Polypeptides

The amino acid sequence for the wild type *H. jecorina* CBH2 is shown in FIG. 1. The variant CBH2 polypeptides comprises a substitution or deletion at a position corresponding to one or more of residues V94, P98, G118, M120, M134, T142, L144, M145, T148, T154, L179, Q204, V206, S210, I212, T214, L215, G231, T232, V250, Q276, N285, S291, G308, T312, S316, V323, N325, I333, G334, S343, T349, G360, S380, A381, S386, F411, S413, A416, Q426 and/or A429 in CBH2 from *Hypocrea jecorina* (SEQ ID NO: 95).

In one aspect the invention relates to an isolated CBH2 enzyme of the Cel6A family having at least one amino acid residue substitution or deletion in a region selected from the group consisting of (1) from position 92 to 100, (2) 115-123, (3) 140-155, (4) 160-180, (5) 198-218, (6) 228-235, (7) 240-260, (8) 275-295, (9) 305-318, (10) 322-335, (11) 340-350, (12) 360-370, (13) 378-390 and (14) 410-430. In another aspect the invention relates to an isolated CBH2 enzyme of the Cel6A family having at least one amino acid residue substitution in a region selected from the group consisting of (1) from position 92 to 100, (2) 115-123, (3) 140-155, (4) 160-180, (5) 198-218, (6) 228-235, (7) 240-260, (8) 275-295, (9) 305-318, (10) 322-335, (11) 340-350, (12) 360-370, (13) 378-390 and (14) 410-430.

The variant CBH2's of this invention have amino acid sequences that are derived from the amino acid sequence of a precursor CBH2. The amino acid sequence of the CBH2 variant differs from the precursor CBH2 amino acid sequence by the substitution, deletion or insertion of one or more amino acids of the precursor amino acid sequence. In a preferred embodiment, the precursor CBH2 is *Hypocrea jecorina* CBH2. The mature amino acid sequence of *H. jecorina* CBH2 is shown in FIG. 1. Thus, this invention is directed to CBH2 variants which contain amino acid residues at positions which are equivalent to the particular identified residue in *H. jecorina* CBH2. A residue (amino acid) of an CBH2 homolog is equivalent to a residue of *Hypocrea jecorina* CBH2 if it is either homologous (i.e., corresponding in position in either primary or tertiary structure) or is functionally analogous to a specific residue or portion of that residue in *Hypocrea jecorina* CBH2 (i.e., having the same or similar functional capacity to combine, react, or interact chemically or structurally). As used herein, numbering is intended to correspond to that of the mature CBH2 amino acid sequence as illustrated in FIG. 1. In addition to locations within the precursor CBH2, specific residues in the precursor CBH2 corresponding to the amino acid positions that are responsible for instability when the precursor CBH2 is under thermal stress are identified herein for substitution or deletion. The amino acid position number (e.g., +51) refers to the number assigned to the mature *Hypocrea jecorina* CBH2 sequence presented in FIG. 1.

Alignment of amino acid sequences to determine homology is preferably determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection, Visual inspection may utilize graphics packages such as, for example, MOE by Chemical Computing Group, Montreal Canada.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M'S, N'-4, and a comparison of both strands. The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

For purposes of the present invention, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polynucleotide sequence comparison: GAP creation penalty of 5.0 and GAP extension penalty of 0.3.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

Additional specific strategies for modifying stability of CBH2 cellulases are provided below:

(1) Decreasing the entropy of main-chain unfolding may introduce stability to the enzyme. For example, the introduction of proline residues may significantly stabilize the protein by decreasing the entropy of the unfolding (see, e.g., Watanabe, et al., Eur. J. Biochem. 226:277-283 (1994)). Similarly, glycine residues have no β-carbon, and thus have considerably greater backbone conformational freedom than many other residues. Replacement of glycines, preferably with alanines, may reduce the entropy of unfolding and improve stability (see, e.g., Matthews, et al., Proc. Natl. Acad. Sci. USA 84; 6663-6667 (1987)). Additionally, by shortening external loops it may be possible to improve stability. It has been observed that hyperthermophile produced proteins have shorter external loops than their mesophilic homologues (see, e.g., Russel, et al., Current Opinions in Biotechnology 6:370-374 (1995)). The introduction of disulfide bonds may also be effective to stabilize distinct tertiary structures in relation to each other. Thus, the introduction of cysteines at residues accessible to existing cysteines or the introduction of pairs of cysteines that could form disulfide bonds would alter the stability of a CBH2 variant.

(2) Decreasing internal cavities by increasing side-chain hydrophobicity may alter the stability of an enzyme. Reducing the number and volume of internal cavities increases the stability of enzyme by maximizing hydrophobic interactions and reducing packing defects (see, e.g., Matthews, Ann. Rev. Biochem. 62:139-160 (1993); Burley, et al., Science 229:23-29 (1985); Zuber, Biophys. Chem. 29:171-179 (1988); Kellis, et al., Nature 333:784-786 (1988)). It is known that multimeric proteins from thermophiles often have more hydrophobic sub-unit interfaces with greater surface complementarity than their mesophilic counterparts (Russel, et al., supra). This principle is believed to be applicable to domain interfaces of monomeric proteins. Specific substitutions that may improve stability by increasing hydrophobicity include lysine to arginine, serine to alanine and threonine to alanine (Russel, et al., supra). Modification by substitution to alanine or proline may increase side-chain size with resultant reduction in cavities, better packing and increased hydrophobicity. Substitutions to reduce the size of the cavity, increase hydrophobicity and improve the complementarity the interfaces between the domains of CBH2 may improve stability of the enzyme. Specifically, modification of the specific residue at these positions with a different residue selected from any of phenylalanine, tryptophan, tyrosine, leucine and isoleucine may improve performance.

(3) Balancing charge in rigid secondary structure, i.e., α-helices and β-turns may improve stability. For example, neutralizing partial positive charges on a helix N-terminus with negative charge on aspartic acid may improve stability of the structure (see, e.g., Eriksson, et al., Science 255:178-183 (1992)). Similarly, neutralizing partial negative charges on helix C-terminus with positive charge may improve stability. Removing positive charge from interacting with peptide N-terminus in β-turns should be effective in conferring tertiary structure stability. Substitution with a non-positively charged residue could remove an unfavorable positive charge from interacting with an amide nitrogen present in a turn.

(4) Introducing salt bridges and hydrogen bonds to stabilize tertiary structures may be effective. For example, ion pair interactions, e.g., between aspartic acid or glutamic acid and lysine, arginine or histidine, may introduce strong stabilizing effects and may be used to attach different tertiary structure elements with a resultant improvement in thermostability. Additionally, increases in the number of charged residue/non-charged residue hydrogen bonds, and the number of hydrogen-bonds generally, may improve thermostability (see, e.g., Tanner, et al., Biochemistry 35:2597-2609 (1996)). Substitution with aspartic acid, asparagine, glutamic acid or glutamine may introduce a hydrogen bond with a backbone amide. Substitution with arginine may improve a salt bridge and introduce an H-bond into a backbone carbonyl.

(5) Avoiding thermolabile residues in general may increase thermal stability. For example, asparagine and glutamine are susceptible to deamidation and cysteine is susceptible to oxidation at high temperatures. Reducing the number of these residues in sensitive positions may result in improved thermostability (Russel, et al., supra). Substitution or deletion by any residue other than glutamine or cysteine may increase stability by avoidance of a thermolabile residue.

(6) Stabilization or destabilization of binding of a ligand that confers modified stability to CBH2 variants. For example, a component of the matrix in which the CBH2 variants of this invention are used may bind to a specific surfactant/thermal sensitivity site of the CBH2 variant. By modifying the site through substitution, binding of the component to the variant may be strengthened or diminished. For example, a non-aromatic residue in the binding crevice of CBH2 may be substituted with phenylalanine or tyrosine to introduce aromatic side-chain stabilization where interaction of the cellulose substrate may interact favorably with the benzyl rings, increasing the stability of the CBH2 variant.

(7) Increasing the electronegativity of any of the surfactant/thermal sensitivity ligands may improve stability under surfactant or thermal stress. For example, substitution with phenylalanine or tyrosine may increase the electronegativity of D (aspartate) residues by improving shielding from solvent, thereby improving stability.

VI. EXPRESSION OF RECOMBINANT CBH2 VARIANTS

The methods of the invention rely on the use cells to express variant CBH2, with no particular method of CBH2 expression required. The CBH2 is preferably secreted from the cells.

The invention provides host cells which have been transduced, transformed or transfected with an expression vector comprising a variant CBH-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding CBH2, such that CBH2 is expressed in the cell line.

A. Nucleic Acid Constructs/Expression Vectors.

Natural or synthetic polynucleotide fragments encoding CBH2 ("CBH2-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of CBH2. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces*, 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for variant CBH2 may be produced by introducing a heterologous nucleic acid construct comprising the variant CBH2 coding sequence into the cells of a selected strain of the filamentous fungi.

Once the desired form of a variant cbh2 nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant cbh2 coding sequence may be inserted into a suitable vector according to well-known recombinant techniques and used to transform filamentous fungi capable of CBH2 expression. Due to the inherent degeneracy of the genetic code, other nucleic acid sequences which encode substantially the same or a functionally equivalent amino acid sequence may be used to clone and express variant CBH2. Therefore it is appreciated that such substitutions in the coding region fall within the sequence variants covered by the present invention. Any and all of these sequence variants can be utilized in the same way as described herein for a parent CBH2-encoding nucleic acid sequence.

The present invention also includes recombinant nucleic acid constructs comprising one or more of the variant CBH2-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for variant cbh2: (i) in isolation; (ii) in combination with additional coding sequences; such as fusion protein or signal peptide coding sequences, where the cbh2 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the cbh2 coding sequence is a heterologous gene.

In one aspect of the present invention, a heterologous nucleic acid construct is employed to transfer a variant CBH2-encoding nucleic acid sequence into a cell in vitro, with established filamentous fungal and yeast lines preferred. For long-term, production of variant CBH2, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a variant CBH2 polypeptide. Such linkage comprises positioning of the promoter with respect to the initiation codon of the DNA sequence encoding the variant CBH2 polypeptide in the disclosed expression vectors. The promoter sequence contains transcription and translation control sequence which mediate the expression of the variant CBH2 polypeptide. Examples include the promoters from the *Aspergillus niger, A. awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* (*T. reesei*) cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, Animal Cell Culture, 1987; Ausubel, et al., 1993; and Coligan et al., Current Protocols in Immunology, 1991.

B. Host Cells and Culture Conditions For CBH2 Production (i) Filamentous Fungi

Thus, the present invention provides filamentous fungi comprising cells which have been modified, selected and cultured in a manner effective to result in variant CBH2 production or expression relative to the corresponding non-transformed parental fungi.

Examples of species of parental filamentous fungi that may be treated and/or modified for variant CBH2 expression include, but are not limited to *Trichoderma*, e.g., *Trichoderma reesei, Trichoderma longibrachiatum, Trichoderma viride, Trichoderma koningii; Penicillium* sp., *Humicola* sp., including *Humicola insolens; Aspergillus* sp., *Chrysosporium* sp., *Fusarium* sp., *Hypocrea* sp., and *Emericella* sp.

CBH2 expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of CBH2 expression are achieved.

Preferred culture conditions for a given filamentous fungus may be found in the scientific literature and/or from the source of the fungi such as the American Type Culture Collection (ATCC; www.atcc.org/). After fungal growth has been established, the cells are exposed to conditions effective to cause or permit the expression of variant CBH2.

In cases where a CBH2 coding sequence is under the control of an inducible promoter, the inducing agent, e.g., a sugar, metal salt or antibiotics, is added to the medium at a concentration effective to induce CBH2 expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAP3-4 are known Ward et al (Ward, M, Wilson, L. J. and Kodama, K. H., 1993, Appl. Microbiol. Biotechnol. 39:738-743).

In another embodiment, the strain comprises *Trichoderma reesei*, which is a useful strain for obtaining overexpressed protein. For example, RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH2.

Where it is desired to obtain the variant CBH2 in the absence of potentially detrimental native cellulolytic activity, it is useful to obtain a *Trichoderma* host cell strain which has had one or more cellulase genes deleted prior to introduction of a DNA construct or plasmid containing the DNA fragment encoding the variant CBH2. Such strains may be prepared by the method disclosed in U.S. Pat. No. 5,246,853 and WO 92/06209, which disclosures are hereby incorporated by reference. By expressing a variant CBH2 cellulase in a host microorganism that is missing one or more cellulase genes, the identification and subsequent purification procedures are simplified. Any gene from *Trichoderma* sp. which has been cloned can be deleted, for example, the cbh1, cbh2, egl1, and egl2 genes as well as those encoding EG III and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of a *Aspergillus* sp. gene may be used which if lacking in the host strain results in the host strain displaying an auxotrophic phenotype. Similarly, selectable markers exist for *Trichoderma* sp.

In one embodiment, a pyrG⁻ derivative strain of *Aspergillus* sp. is transformed with a functional pyrG gene, which thus provides a selectable marker for transformation. A pyrG⁻ derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, Curr. Genet. 19:359-365 (1991), and van Hartingsveldt et al., (1986) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker.

In a second embodiment, a pyr4⁻ derivative strain of *Hyprocrea* sp. (*Hyprocrea* sp. (*Trichoderma* sp.)) is transformed with a functional pyr4 gene, which thus provides a selectable marker for transformation. A pyr4⁻ derivative strain may be obtained by selection of *Hyprocrea* sp. (*Trichoderma* sp.) strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4⁻ derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, 1991). Selection of derivative strains is easily performed using the FOA resistance technique referred to above, and thus, the pyr4 gene is preferably employed as a selectable marker.

To transform pyrG⁻ *Aspergillus* sp. or pyr4⁻ *Hyprocrea* sp. (*Trichoderma* sp.) so as to be lacking in the ability to express one or more cellulase genes, a single DNA fragment comprising a disrupted or deleted cellulase gene is then isolated from the deletion plasmid and used to transform an appropriate pyr⁻ *Aspergillus* or pyr⁻ *Trichoderma* host. Transformants are then identified and selected based on their ability to express the pyrG or pyr4, respectively, gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the appropriate pyr selectable markers.

Although the specific plasmid vectors described above relate to preparation of pyr transformants, the present invention is not limited to these vectors. Various genes can be deleted and replaced in the *Aspergillus* sp. or *Hyprocrea* sp. (*Trichoderma* sp.) strain using the above techniques. In addition, any available selectable markers can be used, as discussed above. In fact, any host, e.g., *Aspergillus* sp. or *Hyprocrea* sp., gene that has been cloned, and thus identified, can be deleted from the genome using the above-described strategy.

As stated above, the host strains used may be derivatives of *Hyprocrea* sp. (*Trichoderma* sp.) that lack or have a nonfunctional gene or genes corresponding to the selectable marker chosen. For example, if the selectable marker of pyrG is chosen for *Aspergillus* sp., then a specific pyrG⁻ derivative strain is used as a recipient in the transformation procedure. Also, for example, if the selectable marker of pyr4 is chosen for a *Hyprocrea* sp., then a specific pyr4⁻ derivative strain is used as a recipient in the transformation procedure. Similarly, selectable markers comprising *Hyprocrea* sp. (*Trichoderma* sp.) genes equivalent to the *Aspergillus nidulans* genes amdS, argB, trpC, niaD may be used. The corresponding recipient strain must therefore be a derivative strain such as argB⁻, trpC⁻, niaD⁻, respectively.

DNA encoding the CBH2 variant is then prepared for insertion into an appropriate microorganism. According to the present invention, DNA encoding a CBH2 variant comprises the DNA necessary to encode for a protein that has functional cellulolytic activity. The DNA fragment encoding the CBH2 variant may be functionally attached to a fungal promoter sequence, for example, the promoter of the glaA gene in *Aspergillus* or the promoter of the cbh1 or egl1 genes in *Trichoderma*.

It is also contemplated that more than one copy of DNA encoding a CBH2 variant may be recombined into the strain to facilitate overexpression. The DNA encoding the CBH2 variant may be prepared by the construction of an expression vector carrying the DNA encoding the variant. The expression vector carrying the inserted DNA fragment encoding the CBH2 variant may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker may also be contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences.

For example, in *Aspergillus*, pRAX is such a general-purpose expression vector. Genes or part thereof can be inserted downstream of the strong glaA promoter.

For example, in *Hypocrea*, pTEX is such a general-purpose expression vector. Genes or part thereof can be inserted downstream of the strong cbh1 promoter.

In the vector, the DNA sequence encoding the CBH2 variant of the present invention should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the CBH2 variant. The DNA encoding the signal sequence is preferably that which is naturally associated with the gene to be expressed, however the signal sequence from any suitable source, for example an exo-cellobiohydrolase or endoglucanase from *Trichoderma*, is contemplated in the present invention.

The procedures used to ligate the DNA sequences coding for the variant CBH2 of the present invention with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Hyprocrea* sp. (*Trichoderma* sp.) is very low. Accordingly, uptake of the desired DNA sequence, gene or gene fragment is at best minimal. There are a number of methods to increase the permeability of the *Hyprocrea* sp. (*Trichoderma* sp.) cell wall in the derivative strain (i.e., lacking a functional gene corresponding to the used selectable marker) prior to the transformation process.

The preferred method in the present invention to prepare *Aspergillus* sp. or *Hyprocrea* sp. (*Trichoderma* sp.) for transformation involves the preparation of protoplasts from fungal mycelium. See Campbell et al. Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host strain, (*Aspergillus* sp. or *Hyprocrea* sp. (*Trichoderma* sp.), is dependent upon the calcium ion concentration. Generally between about 10 mM $CaCl_2$ and 50 mM $CaCl_2$ is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the host cell, by way of example either *Aspergillus* sp. or *Hyprocrea* sp. strain, and the plasmid DNA is transferred to the nucleus. This fusion frequently leaves multiple copies of the plasmid DNA integrated into the host chromosome.

Usually a suspension containing the *Aspergillus* sp. protoplasts or cells that have been subjected to a permeability treatment at a density of $10^5$ to $10^6$/mL, preferably $2 \times 10^5$/mL are used in transformation. Similarly, a suspension containing the *Hyprocrea* sp. (*Trichoderma* sp.) protoplasts or cells that have been subjected to a permeability treatment at a density of $10^8$ to $10^9$/mL, preferably $2 \times 10^8$/mL are used in transformation. A volume of 100 μL of these protoplasts or cells in an appropriate solution (e.g., 1.2 M sorbitol; 50 mM $CaCl_2$) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0° C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and $CaCl_2$ solution. The protoplast suspension is then further added to molten aliquots of a growth medium. This growth medium permits the growth of transformants only. Any growth medium can be used in the present invention that is suitable to grow the desired transformants. However, if Pyr$^+$ transformants are being selected it is preferable to use a growth medium that contains no uridine.

The subsequent colonies are transferred and purified on a growth medium depleted of uridine.

At this stage, stable transformants may be distinguished from unstable transformants by their faster growth rate and, in *Trichoderma*, for example, the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the CBH2 variant(s) are recovered in active form from the host cell after growth in liquid media as a result of the appropriate post translational processing of the CBH2 variant.

(ii) Yeast The present invention also contemplates the use of yeast as a host cell for CBH2 production. Several other genes encoding hydrolytic enzymes have been expressed in various strains of the yeast *S. cerevisiae*. These include sequences encoding for two endoglucanases (Penttila et al., Yeast vol. 3, pp 175-185, 1987), two cellobiohydrolases (Penttila et al., Gene, 63: 103-112, 1988) and one beta-glucosidase from *Trichoderma reesei* (Cummings and Fowler, Curr. Genet. 29:227-233, 1996), a xylanase from *Aureobasidium pullulans* (Li and Ljungdahl, Appl. Environ. Microbiol. 62, no. 1, pp. 209-213, 1996), an alpha-amylase from wheat (Rothstein et al., Gene 55:353-356, 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (Bgl1) was successfully expressed in a laboratory strain of *S. cerevisiae* (Van Rensburg et al., Yeast, vol. 14, pp. 67-76, 1998).

C. Introduction of a CBH2-Encoding Nucleic Acid Sequence into Host Cells.

The invention further provides cells and cell compositions which have been genetically modified to comprise an exogenously provided variant CBH2-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

Other methods for introducing a heterologous nucleic acid construct (expression vector) into filamentous fungi (e.g., *H. jecorina*) include, but are not limited to the use of a particle or gene gun, permeabilization of filamentous fungi cells walls prior to the transformation process (e.g., by use of high concentrations of alkali, e.g., 0.05 M to 0.4 M $CaCl_2$ or lithium acetate), protoplast fusion or *Agrobacterium* mediated transformation. An exemplary method for transformation of filamentous fungi by treatment of protoplasts or spheroplasts with polyethylene glycol and $CaCl_2$ is described in Campbell, E. I. et al., Curr. Genet. 16:53-56, 1989 and Penttila, M. et al., Gene, 63:11-22, 1988.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

In addition, heterologous nucleic acid constructs comprising a variant CBH2-encoding nucleic acid sequence can be transcribed in vitro, and the resulting RNA introduced into the host cell by well-known methods, e.g., by injection.

The invention further includes novel and useful transformants of filamentous fungi such as *H. jecorina* and *A. niger* for use in producing fungal cellulase compositions. The invention includes transformants of filamentous fungi especially fungi comprising the variant CBH2 coding sequence, or deletion of the endogenous cbh coding sequence.

Following introduction of a heterologous nucleic acid construct comprising the coding sequence for a variant cbh2, the genetically modified cells can be cultured in conventional nutrient media modified as appropriate for activating promoters, selecting transformants or amplifying expression of a variant CBH2-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the variant CBH2-encoding nucleic acid sequence found in the heterologous nucleic acid construct.

The invention further includes novel and useful transformants of filamentous fungi such as *H. jecorina* for use in producing fungal cellulase compositions. *Aspergillus niger* may also be used in producing the variant CBH2. The invention includes transformants of filamentous fungi especially fungi comprising the variant cbh 2 coding sequence, or deletion of the endogenous cbh2 coding sequence.

Stable transformants of filamentous fungi can generally be distinguished from unstable transformants by their faster growth rate and, in *Trichoderma*, for example, the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VII. ANALYSIS FOR CBH2 NUCLEIC ACID CODING SEQUENCES AND/OR PROTEIN EXPRESSION

In order to evaluate the expression of a variant CBH2 by a cell line that has been transformed with a variant CBH2-encoding nucleic acid construct, assays can be carried out at the protein level, the RNA level or by use of functional bioassays particular to cellobiohydrolase activity and/or production.

In one exemplary application of the variant cbh2 nucleic acid and protein sequences described herein, a genetically modified strain of filamentous fungi, e.g., *Trichoderma reesei*, is engineered to produce an increased amount of CBH2. Such genetically modified filamentous fungi would be useful to produce a cellulase product with greater increased cellulolytic capacity. In one approach, this is accomplished by introducing the coding sequence for cbh2 into a suitable host, e.g., a filamentous fungi such as *Aspergillus niger*.

Accordingly, the invention includes methods for expressing variant CBH2 in a filamentous fungus or other suitable host by introducing an expression vector containing the DNA sequence encoding variant CBH2 into cells of the filamentous fungus or other suitable host.

In another aspect, the invention includes methods for modifying the expression of CBH2 in a filamentous fungus or other suitable host. Such modification includes a decrease or elimination in expression of the endogenous CBH2.

In general, assays employed to analyze the expression of variant CBH2 include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of variant CBH2 may be measured in a sample directly, for example, by assays for cellobiohydrolase activity, expression and/or production. Such assays are described, for example, in Karlsson, J. et al. (2001), Eur. J. Biochem, 268, 6498-6507, Wood, T. (1988) in Methods in Enzymology, Vol. 160. Biomass Part a Cellulose and Hemicellulose (Wood, W. & Kellog, S. Eds.), pp. 19-25, Academic Press, San Diego, Calif., USA) and, for the PAHBAH assay in (Lever, M. (1972) Analytical Biochemistry, 47, 273, Blakeney, A. B. & Mutton, L. L. (1980) Journal of Science of Food and Agriculture, 31, 889, Henry, R. J. (1984) Journal of the Institute of Brewing, 90, 37 Substrates useful for assaying cellobiohydrolase, endoglucanase or β-glucosidase activities include crystalline cellulose, filter paper, phosphoric acid swollen cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside.

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a CBH2 variant. The details of such methods are known to those of skill in the art and many reagents for practicing such methods are commercially available.

A purified form of a variant CBH2 may be used to produce either monoclonal or polyclonal antibodies specific to the expressed protein for use in various immunoassays. (See, e.g., Hu et al., Mol Cell Biol. vol. 11, no. 11, pp. 5792-5799, 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of cellobiohydrolase proteins.

VIII. ISOLATION AND PURIFICATION OF RECOMBINANT CBH2 PROTEIN

In general, a variant CBH2 protein produced in cell culture is secreted into the medium and may be purified or isolated, e.g., by removing unwanted components from the cell culture medium. However, in some cases, a variant CBH2 protein may be produced in a cellular form necessitating recovery from a cell lysate. In such cases the variant CBH2 protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatographic methods (Goyal et al., Bioresource Technol. 36:37-50, 1991; Fliess et al., Eur. J. Appl. Microbiol. Biotechnol. 17:314-318, 1983; Bhikhabhai et al., J. Appl. Biochem. 6:336-345, 1984; Ellouz et al., J. Chromatography 396:307-317, 1987), including ion-exchange using materials with high resolution power (Medve et al., J. Chromatography A 808:153-165, 1998), hydrophobic interaction chromatography (Tomaz and Queiroz, J. Chromatography A 865:123-128, 1999), and two-phase partitioning (Brumbauer, et al., Bioseparation 7:287-295, 1999).

Typically, the variant CBH2 protein is fractionated to segregate proteins having selected properties, such as binding affinity to particular binding agents, e.g., antibodies or receptors; or which have a selected molecular weight range, or range of isoelectric points.

Once expression of a given variant CBH2 protein is achieved, the CBH2 protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods in Enzymology, vol. 182, no. 57, pp. 779, 1990; Scopes, Methods Enzymol. 90: 479-91, 1982. The purification step(s) selected will depend, e.g., on the nature of the production process used and the particular protein produced.

IX. UTILITY OF cbh2 AND CBH2

It can be appreciated that the variant cbh nucleic acids, the variant CBH2 protein and compositions comprising variant CBH2 protein activity find utility in a wide variety applications, some of which are described below.

New and improved cellulase compositions that comprise varying amounts BG-type, EG-type and variant CBH-type cellulases find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

Variant (or mutant) CBHs with increased thermostability find uses in all of the above areas due to their ability to retain activity at elevated temperatures.

Variant (or mutant) CBHs with decreased thermostability find uses, for example, in areas where the enzyme activity is required to be neutralized at lower temperatures so that other enzymes that may be present are left unaffected. In addition, the enzymes may find utility in the limited conversion of cellulosics, for example, in controlling the degree of crystallinity or of cellulosic chain-length. After reaching the desired extent of conversion the saccharifying temperature can be raised above the survival temperature of the de-stabilized CBH. As the CBH activity is essential for hydrolysis of crystalline cellulose, conversion of crystalline cellulose will cease at the elevated temperature.

In one approach, the cellulase of the invention finds utility in detergent compositions or in the treatment of fabrics to improve the feel and appearance.

Since the rate of hydrolysis of cellulosic products may be increased by using a transformant having at least one additional copy of the cbh gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the variant CBH type cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive variant CBH and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase finds use in the hydrolysis of cellulose to its sugar components. In one embodiment, a variant cellobiohydrolase is added to the biomass prior to the addition of a fermentative organism. In a second embodiment, a variant cellobiohydrolase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

The major product of CBH2 action on cellulose is cellobiose which is available for conversion to glucose by BG activity (for instance in a fungal cellulase product). Either by the pretreatment of the cellulosic biomass or by the enzymatic action on the biomass, other sugars, in addition to glucose and cellobiose, can be made available from the biomass. The hemi-cellulose content of the biomass can be converted (by hemi-cellulases) to sugars such as xylose, galactose, mannose and arabinose. Thus, in a biomass conversion process, enzymatic saccharification can produce sugars that are made available for biological or chemical conversions to other intermediates or end-products. Therefore, the sugars generated from biomass find use in a variety of processes in addition to the generation of ethanol. Examples of such conversions are fermentation of glucose to ethanol (as reviewed by M. E. Himmel et al. pp 2-45, in "Fuels and Chemicals from Biomass", ACS Symposium Series 666, ed B. C. Saha and J. Woodward, 1997) and other biological conversions of glucose to 2,5-diketo-D-gluconate (U.S. Pat. No. 6,599,722), lactic acid (R. Datta and S-P. Tsai pp 224-236, ibid), succinate (R. R. Gokarn, M. A. Eiteman and J. Sridhar pp 237-263, ibid), 1,3-propanediol (A-P. Zheng, H. Biebl and W-D. Deckwer pp 264-279, ibid), 2,3-butanediol (C. S. Gong, N. Cao and G. T. Tsao pp 280-293, ibid), and the chemical and biological conversions of xylose to xylitol (B. C. Saha and R. J. Bothast pp 307-319, ibid). See also, for example, WO 98/21339.

The detergent compositions of this invention may employ besides the cellulase composition (irrespective of the cellobiohydrolase content, i.e., cellobiohydrolase-free, substantially cellobiohydrolase-free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH2 type components," which is incorporated herein by reference.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

In addition the variant CBH2 nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knockout (reverse genetics, targeted knock-out, viral induced gene silencing (VIGS, see Baulcombe, 100 Years of Virology, Calisher and Horzinek eds., Springer-Verlag, New York, N.Y. 15:189-201, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

All patents, patent applications, articles and publications mentioned herein, are hereby expressly incorporated herein by reference.

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein.

Example 1

Alignment of Known Cel6A Cellulases

The choice of several of the mutations was determined by first aligning *Hypocrea jecorina* Cel6A to eight (8) family members using structural information and a modeling program. FIG. 3 shows the alignment of CBH2 molecules derived from *Humicola insolens* (Q9C1S9), *Acremonium cellulolyticus* (O93837), *Agaricus bisporus* (P49075), *Hypocrea koningii* (AF315681), *Phanerochaete chrysosporium* (S76141), *Talaromyces emersonii* (Q8N1B5), *Lentinula edodes* (AF244369), *Hypocrea jecorina* (P07987). Alignments were done by Clustal W with a gap penalty of 10 using Vector NTI Suite software program.

Based on the alignments, various single and multiple amino acid mutations were made in the protein by site mutagenesis. Possible mutations were identified that might improve the thermostability of the enzyme by using the consensus sequence. See FIG. 3. A visual inspection of the 3D-structure was performed to check for their compatibility with the structure. All changes, which do either not fit into the CBH2 molecule for sterical reasons or are to close to the active site, were omitted from the set of initial mutations.

The consensus sequence for CBH2 was determined by aligning CBH2 sequences as described herein. The alignment of FIG. 3 served as basis for the determination of the so-called consensus sequence. The consensus sequence of an alignment is the sequence, which has at each position the amino acid, which is found in the majority of the amino acid sequences, which were used to construct the alignment. Those positions where the consensus sequence deviated from the CBH2 *T. reesei* amino acid sequence were evaluated by examining the 3D-structure of the protein (PDB-code 1QK2). The graphical inspection was done using the computer program BRAGI (D. Schomburg, J. Reichelt, J. Mol. Graphics, Vol 6, 161-165 (1988)) on a Silicon Graphics Indigo2 Solid Impact computer. Those mutations that—according to the 3D-model—fit into the structure without disturbance and were likely to improve the thermostability of the enzyme were selected as replacement for improved thermostability of *H. jecorina* CBH2. In some cases the visual inspection of the 3D-structure of the CBH2-molecule made it necessary to replace a non-conserved residue of *H. jecorina* CBH2 by another amino acid than the sequence alignment suggested. In some cases, the amino acid is glycosylated in the 3D-structure. The glycosylated positions, which were investigated based on the alignment, are S109 and N310. These positions were not changed. At position V94 the valine was replaced by a glutamic acid residue, because it might have stabilizing charge interactions with one or two arginines at position 213 and/or 237. At position T142 we decided to introduce a proline, which might fit according to the sequence alignment. This amino acid is found at many of the aligned sequences and can stabilize due to the entropic effect of the proline. At position L179 we decided to test the effect of an introduction of an alanine, which is the only alternative amino acid in the CBH2 molecules in this alignment. At position Q204, we decided to replace the glutamine by a glutamic acid residue and not by alanine as suggested by the consensus sequence, because the alanine introduction might destroy favorable interactions in the hydrophobic core, whereas the introduction of a charge through the Q to E mutation should improve the charge network on the surface of the molecule. We replaced V206 by leucine, because the fit in the hydrophobic core seems better than fitting isoleucine. In case of V250, we decided to replace it by leucine and not by the slightly bigger isoleucine due to space constraints. At position N285, we investigated the influence of the side chain length on stability by replacing the asparagine by glutamine. At position S291 we decided to test the effect of an introduction of a glycine, which is the only alternative amino acid in the CBH2 molecules in this alignment. At position S316 we decided to test the effect of an introduction of a proline, which is the only alternative amino acid in the CBH2 molecules in this alignment. At position S343 we decided to introduce a proline due to its stabilizing effect on the backbone and the fact that this amino acid is the most frequent one at this position in the alignment. At position T349 the threonine was replaced by a leucine and not by valine as suggested by the consensus sequence. At position S413 we decided to test the effect of an aromatic residue on stability at this position by replacing the serine by tyrosine.

Example 2

Preparation of cbh2 Constructs

The cDNA sequence of CBH2 presented in FIG. 2 served as the template for amplifying the gene. It also served as the template for the introduction of mutations.

The following DNA primers were constructed for use in amplification of mutant cbh2 genes from genomic DNA's isolated from various microorganisms. All symbols used herein for protein and DNA sequences correspond to IUPAC IUB Biochemical Nomenclature Commission codes.

Homologous 5' (FRG361) and 3' (FRG362) primers were developed based on the sequence of cbh2 from *Trichoderma reesei*. Both primers contained Gateway cloning sequences from Invitrogen® at the 5' of the primer. Primer 361 contained attB1 sequence and primer FRG362 contained attB2 sequence.

```
Sequence of FRG361 without the attB1:
                                    (SEQ ID NO: 3)
ATGATTGTCGGCATTCTCAC
(this primes the 5' end of the gene, encoding the
signal sequence of CBH2 H. jecorina)

Sequence of FRG362 without the attB2:
                                    (SEQ ID NO: 4) )
TTACAGGAACGATGGGTTTGCG
(this primes the 3' end of the gene encoding the
catalytic domain of CBH2 H. jecorina)
```

The *H. jecorina* cbh2 cDNA served as template. The cDNA used was derived from a cDNA library prepared as described by Pamela K. Foreman et al, Journal of Biological Chemistry Vol 278 No 34 2003 page 31989. The library was screened with specific CBH2 catalytic domain probe using primers:

TABLE 1

| cbh2 | forw. | FRG170 | ACG TAT TCA GGC AAC CC |
|------|-------|--------|------------------------|
|      | rev.  | FRG171 | GCA GTG GCC ATG GCT CC |

PCR conditions were as follows: 10 μL, of 10× reaction buffer (10× reaction buffer comprising 100 mM Tris HCl, pH 8-8.5; 250 mM KCl; 50 mM $(NH_4)_2SO_4$; 20 mM $MgSO_4$); 0.2 mM each of dATP, dTTP, dGTP, dCTP (final concentration), 1 μL, of 100 ng/μL genomic DNA, 0.5 μL of PWO polymerase (Boehringer Mannheim, Cat #1644-947) at 1 unit per μL, 0.2 μM of each primer, FRG361 and FRG362, (final concentration), 4 μl DMSO and water to 100 μL.

The fragments encoding the variants were purified from an agarose gel using the Qiagen Gel extraction KIT. The purified fragments were used to perform a clonase reaction with the pDONR™201 vector from Invitrogen® using the Gateway™ Technology instruction manual (version C) from Invitrogen®, hereby incorporated by reference herein. The thus prepared pENTRYCBH2 clone is given in FIG. 4.

Various sites in *H. jecorina* CBH2 may be involved in the thermostability of the variants and the *H. jecorina* cbh2 gene was therefore subjected to mutagenesis using the primers and reaction reagents described below.

The cycling parameters for each reaction (single site mutagenesis, random mutagenesis, regional mutagenesis or combinatorial) were the same:

TABLE 2

| Segment | Cycles | Temperature | Time |
|---------|--------|-------------|------|
| 1 | 1 | 95° C. | 1 minute |
| 2 | 30 | 95° C. | 1 minute |
|   |    | 55° C. | 1 minute |
|   |    | 65° C. | 12 minutes |
| 3 | 1 | 4° C. | 2 minutes |

The amplification products were isolated and characterized as described below (see Examples 3-6.

Genes (variant or wild type) having the correct sequence were then transferred from this ENTRY vector to the destination vector (pRAXdes2) to obtain the expression vector pRAXdesCBH2.

Cells were transformed with an expression vector comprising a variant CBH2 cellulase encoding nucleic acid. The constructs were transformed into *A. niger* var. *awamori* according to the method described by Cao et al (Cao Q-N, Stubbs M, Ngo K Q P, Ward M, Cunningham A, Pai E F, Tu G-C and Hofmann T (2000) Penicillopepsin-JT2 a recombinant enzyme from *Penicillium janthinellum* and contribution of a hydrogen bond in subsite S3 to kcat *Protein Science* 9:991-1001).

Example 3

Site Directed Mutagenesis

Based on the above rationale presented in Example 1, Site Directed CBH2 mutants were made with the following 5' phosphorylated primers that were developed and synthesized using techniques well known in the art:

TABLE 3

Primers for Single Site Directed Mutants

| mutation | Primer | bps | SEQ ID NO. |
|----------|--------|-----|------------|
| V94E | CAGGCAACCCTTTTGAAGGGGTCACTCCTTGGCG | 34 | |
| P98L | CAACCCTTTTGTTGGGGTCACTCTTTGGGCCAATGC | 36 | |
| G118P | GCTATTCCTAGCTTGACTCCAGCCATGGCCACTGCTG | 37 | |
| M120L | TCCTAGCTTGACTGGAGCCCTGGCCACTGCTGC | 33 | |
| M134V | GCTGTCGCAAAGGTTCCCTCTTTTTGTGTGGCTAGATACTCTTG | 43 | |
| T142V | GATACTCTTGACAAGGTCCCTCTCATGGAGCAAACCTTGGCC | 42 | |
| M145L | CAAGACCCCTCTCCTGGAGCAAACCTTGGCCGAC | 34 | |
| T148Y | GACCCCTCTCATGGAGCAATACTTGGCCGACATCCG | 36 | |
| T154A | CGACATCCGCGCCGCCAACAAGAATGGCGG | 30 | |
| L179A | CGATTGCGCTGCCGCTGCCTCGAATGGCG | 29 | |
| Q204E | CGACACCATTCGTGAAATTGTCGTGGAATATTCCGATATCCG | 42 | |

TABLE 3-continued

Primers for Single Site Directed Mutants

| mutation | Primer | bps | SEQ ID NO. |
|---|---|---|---|
| V206L | CGACACCATTCGTCAAATTCTCGTGGAATATTC CGATATCCG | 42 | |
| I212V | GAATATTCCGATGTCCGGACCCTCCTGGTTATT GAGCCTG | 40 | |
| L215I | GGAATATTCCGATATCCGGACCATCCTGGTTAT TGAGCCTGAC | 43 | |
| G231N | CTGGTGACCAACCTCAATACTCCAAAGTGTGCC AATGCTCAG | 42 | |
| T232V | GACCAACCTCGGTGTTCCAAAGTGTGCCAATGC TCAG | 37 | |
| V250I | TGAGTGCATCAACTACGCCATCACACAGCTGAA CCTTCC | 39 | |
| Q276L | CCGGCAAACCTAGACCCGGCCGCTCAGCTATT TG | 34 | |
| N285Q | GGCCGCTCAGCTATTTGCACAAGTTTACAAGAA TGCATCG | 40 | |
| S291G | GTTTACAAGAATGCAGGGTCTCCGAGAGCTCTT CGCGG | 38 | |
| G308A | GTCGCCAACTACAACGCGTGGAACATTACCAG CCC | 35 | |
| T312S | CAACGGGTGGAACATTAGCAGCCCCCCATCGT AC | 34 | |
| S316P | CATTACCAGCCCCCACCGTACACGCAAGGC | 31 | |
| V323N | CAAGGCAACGCTAACTACAACGAGAAGCTGTA CATCCACGC | 41 | |
| N325D | CAAGGCAACGCTGTCTACGACGAGAAGCTGTA CATCCAC | 39 | |
| I333L | GCTGTACATCCACGCTCTTGGACCTCTTCTTGC CAATCAC | 40 | |
| G334A | TACATCCACGCTATTGCACCTCTTCTTGCCAAT CACGG | 38 | |
| S343P | CCAATCACGGCTGGCCCAACGCCTTCTTCATC | 32 | |
| T349L | CAACGCCTTCTTCATCCTTGATCAAGGTCGATC GGGAAAG | 40 | |
| G360R | GAAAGCAGCCTACCAGACAGCAACAGTGGGGA GACTGG | 38 | |
| S380T | GGTATTCGCCCAACCGCAAACACTGGGGACTC G | 33 | |
| A381T | GGTATTCGCCCATCCACAAACACTGGGGACTC GTTG | 36 | |
| S386P | GACTCGTTGCTGGATGCGTTTGTCTGGGTCAAG CC | 35 | |
| F411Y | AGTGCGCCACGATATGACTCCCACTGTGCGCT C | 33 | |
| S413Y | GCCACGATTTGACTACCACTGTGCGCTCCCAG ATG | 35 | |
| A416G | TTTGACTCCCACTGTGGGCTCCCAGATGCCTTG | 33 | |
| Q426E | CAACCGGCGCCTGAAGCTGGTGCTTGGTTC | 30 | |
| A429T | GCGCCTCAAGCTGGTACTTGGTTCCAAGCCTA CTTTGTG | 39 | |

Codons encoding the mutation are underlined and in bold type.

To develop the Site Directed Mutants the QuikChange Multi Site-Directed Mutagenesis Kit (Stratagene, La Jolla, Calif.; Cat #200513) was used.

The mutagenesis reaction was carried out using the following reaction reagents:

TABLE 4

| component | concentration | amount |
|---|---|---|
| Phosphorylated primer (from Table 2, above) | 100 µM | 1 µl |
| pEntryCBH2 | 50 ng/µl | 1 µl |
| dNTP's | 10 mM | 1 µl |
| 10 * QC buffer | Stratagene | 2.5 µl |
| QC enzyme | Stratagene | 1 µl |
| Sterile MilliQ water | | 18.5 µl |

The amplification products were recovered (purified from primers, nucleotides, enzymes, mineral oil, salts, and other impurities) were digested with Dpn I. One microliter Dpn I (10 U/µl) was added to the PCR mixture and incubated at 37° C. for 90 min. The PCR reaction products were purified using QIAquick PCR purification Kit (250) (Qiagen, Cat. No. 28106) according to manufacturer's instruction. The elution volume was 35 µl elution buffer.

To remove double stranded non-mutated DNA, the eluted sample was digested a second time with Dpn I restriction enzyme. 1 µl Dpn I from Invitrogen (Cat. No. 15242-019) and 4 µl reaction buffer (React 4 is supplied with Dpn I as a 10× solution; dilute 1:10 in final reaction mixture) were added to the sample and incubated at 37° C. for 90 minutes. Two microliters of the reaction sample was used for transformation of 10 µl One-Shot Top10 electro-competent cells (Invitrogen, Cat. No. C4040-50). After 1 hour of growth at 37° C. in SOC medium (See Hanahan (1983) J. Mol. Biol. 166:557-580), the cells have been plated on selective Kanamycin plates, and incubated at 37° C. overnight. Positive clones were grown in 2*TY medium with 100 µg/ml ampicillin, and plasmid DNA was isolated with QIAprep Spin Miniprep Kit (Cat. No. 27106). The plasmids were sequenced to confirm that the mutation sequence had been incorporated correctly.

Mutants with the right sequence were transferred to the A. niger expression vector pRAXdest#2 with the LR reaction, according the Gateway Cloning procedure (Invitrogen; Cat. No. 11791019). After protoplast transformation of the expression clones to A. niger AP4, the Site Directed Mutants (SDM) were screened for altered thermostability (Table 14).

Example 4

Combinatorial Libraries

Two QuikChange libraries (QC2C and QC2D) were developed, based on the results for single site mutations that were identified during the SDM screening: 98, 134, 206, 212, 312, 316, 411 and 413.

The mutations P98L, M134V, V206L, I212V, T312S, S316P, F411Y and S413Y were randomly combined in libraries using the quick-change (QC) method. To develop QC libraries the Multi Site-Directed Mutagenesis Kit (Cat #200513 from Strategene) was used.

The primers were prepared as listed in the table below:

TABLE 5

| Name | Primer |
|---|---|
| 98 FP | CAACCCTTTTGTTGGGGTCACTCTTTGGGCCAATGC |
| 134 FP | GCTGTCGCAAAGGTTCCCTCTTTTGTGTGGCTAGATACTCTTG |
| 206 FP | CGACACCATTCGTCAAATTCTCGTGGAATATTCCGATATCCG |
| 212 FP | GAATATTCCGATGTCCGGACCCTCCTGGTTATTGAGCCTG |
| 206/212 FP | CGTCAAATTCTCGTGGAATATTCCGATGTCCGGACCCTCC |
| 312 FP | CAACGGGTGGAACATTAGCAGCCCCCCATCGTAC |
| 316 FP | CATTACCAGCCCCCCACCGTACACGCAAGGC |
| 312/316 FP | GGTGGAACATTAGCAGCCCCCCACCGTACACGCAAGGC |
| 411 FP | AGTGCGCCACGATATGACTCCCACTGTGCGCTC |
| 413 FP | GCCACGATTTGACTACCACTGTGCGCTCCCAGATG |
| 411/413 FP | GTGCGCCACGATATGACTACCACTGTGCGCTCCCAGATG |

A primer mix was prepared as follows:

Thirty microliters of primers 98 and 134 (see above table) were mixed with the 10 μl of each other primer (see above table). Two different primer concentrations were tested resulting in two libraries of which one contained an average of 2 amino acid substitutions and the second 6 amino acids substitutions per molecule.

The mutagenesis reaction was carried out using the following reaction reagents:

TABLE 6

| component | concentration | | QC2C | QC2D |
|---|---|---|---|---|
| Phosphorylated primermix | 10 μM | | 1 μl | 10 |
| pEntryCBH2 | 250 ng/μl | | 1 μl | 1 μl |
| dNTP's | 10 mM | | 1 μl | 1 μl |
| 10 * QC buffer | Stratagene | | 2.5 μl | 2.5 μl |
| QC enzyme | Stratagene | | 1 μl | 1 μl |
| Sterile MilliQ water | | | 18.5 μl | 9.5 μl |

The amplification products were digested with Dpn I. 1 μl DpnI (10 U/μl) was added to the PCR mixture and incubated at 37° C. for 90 min. The PCR reaction products were purified using QIAquick PCR purification Kit (250) (Qiagen, Cat. No. 28106) according to manufacturer's instruction. The elution volume was 35 μl elution buffer.

To remove double stranded non-mutated DNA, the eluted sample was digested a second time with Dpn I restriction enzyme. 1 μl Dpn I from Invitrogen (Cat. No. 15242-019) and 4 μl reaction buffer (React 4 is supplied with Dpn I as a 10× solution; dilute 1:10 in final reaction mixture) were added to the sample and incubated at 37° C. for 90 minutes. Two microliters of the reaction sample was used for transformation of 10 μl One-Shot Top10 electro-competent cells (Invitrogen, Cat. No. C4040-50). After 1 hour of growth at 37° C. in SOC medium (See Hanahan (1983) J. Mol. Biol. 166:557-580), the cells were plated on selective Kanamycin plates, and incubated at 37° C. overnight.

Positive clones were grown in 2*TY medium with 100 μg/ml ampicillin, and plasmid DNA was isolated with QIAprep Spin Miniprep Kit (Cat. No. 27106). The plasmids were sequenced to confirm that the mutation sequence had been incorporated correctly.

Mutants with the right sequence were transferred to the A. niger expression vector pRAXdest#2 with the LR reaction, according the Gateway Cloning procedure (Invitrogen; Cat. No. 11791019). After protoplast transformation of the expression clones to A. niger AP4, the QC libraries were screened for altered thermostability (Tables 15, 16).

Example 5

Regional Mutagenesis

As described below, based on the results for single site mutations that were identified during the SDM screening, regions were identified in the 3D-structure of CBH2, randomly mutated and screened in a thermostability assay. The amino acids, which make up such a spatial region are (in groups): [210, 214], [253, 255, 257, 258], [411, 413, 415], [412, 414, 416], [312, 313], 323, [212, 149, 152], [134, 144] and 98.

Fully randomized libraries at the positions above (i.e., [210, 214], [253, 255, 257, 258], [411, 413, 415], [412, 414, 416], [312, 313], 323, [212, 149, 152], [134, 144] and 98) were screened. The amino acids in the list above between brackets (e.g., [210, 214]) were randomized together, the amino acids 323 and 98 were randomized alone. The variants CBH2-S316P or CBH2-V206L-S316P served as the backbone for these libraries.

NNS primers were constructed and ordered from Invitrogen:

TABLE 7

| RL number | Sites | Primers |
|---|---|---|
| 1 | 210/214 for | CGTCAAATTCTCGTGGAATATNNSGATATCCGGNNSCTCCTGGTTATTG |
| | 210/214 rev | CAATAACCAGGAGSNNCCGGATATCSNNATATTCCACGAGAATTTGACG |
| 2 | 253/255/257/258 for | GTCACACAGNNSAACNNSCCANNSNNSGCGATGTATTTG |
| | 253/255/257/258 rev | CAAATACATCGCSNNSNNTGGSNNGTTSNNCTGTGTGAC |

TABLE 7-continued

| RL number | Sites | Primers |
|---|---|---|
| 3 | 411/413/415 for | GCGCCACGANNSGACNNSCACNNSGCGCTCCCAGATGCC |
|   | 411/413/415 rev | GGCATCTGGGAGCGCSNNGTGSNNGTCSNNTCGTGGCGC |
| 4 | 412/414/416 for | GCGCCACGATTTNNSTCCNNSTGTNNSCTCCCAGATGCCTTG |
|   | 412/414/416 rev | CAAGGCATCTGGGAGSNNACASNNGGASNNAAATCGTGGCGC |
| 5 | 312/313 for | CAACGGGTGGAACATTNNSNNSCCCCCACCGTACACGCAAGGC |
|   | 312/313 rev | GCCTTGCGTGTACGGTGGGGGSNNSNNAATGTTCCACCCGTTG |
| 6 | 323 for | CCCCCACCGTACACGCAAGGCAACGCTNNSTACAACGAGAAG |
|   | 323 rev | CTTCTCGTTGTASNNAGCGTTGCCTTGCGTGTACGGTGGGGG |
| 7 | 212 for | GAATATTCCGATNNSCGGACCCTCCTGGTTATTGAGCCTG |
|   | 212 rev | CAGGCTCAATAACCAGGAGGGTCCGSNNATCGGAATATTC |
|   | 149/152 for | CCTCTCATGGAGCAAACCNNSGCCGACNNSCGCACCGC |
|   | 149/152 rev | GGCGGTGCGSNNGTCGGCSNNGGTTTGCTCCATGAGAGG |
| 8 | 134/144 for | CCCTCTTTTNNSTGGCTAGATACTCTTGACAAGACCCCTNNSATGGAGCAAACC |
|   | 134/144 rev | GGTTTGCTCCATSNNAGGGGTCTTGTCAAGAGTATCTAGCCASNNAAAAGAGGG |
| 9 | 98 for | CAACCCTTTTGTTGGGGTCACTNNSTGGGCCAATGC |
|   | 98 rev | GCATTGGCCCASNNAGTGACCCCAACAAAAGGGTTG |

PCR was performed according to the following protocol, with Pfu Ultra DNA polymerase (Strategene; Cat. No. 600380):

TABLE 8

| component | concentration | amount |
|---|---|---|
| Forward primer | 10 µM | 2 µl |
| Reverse primer | 10 µM | 2 µl |
| Backbone sequence | — | 1 µl |
| dNTP's | 10 mM | 1 µl |
| 10 * Pfu buffer | Stratagene | 5 µl |
| Pfu Ultra enzyme | Stratagene | 0.5 µl |
| DMSO | — | 2 µl |
| Sterile MilliQ water | | 36.5 µl |

PCR fragments were put on a 1% LMT gel, and purified with a Qiagen Gel Extraction Kit (Strategene Cat. No. 28706). The purified fragments were fused with Pfu Ultra (see above) and the cbh2 primers with attB flanking-sequences.

Purified cbh2 genes were transferred into the Gateway Entry-Vector pDON201 with the BP reaction, according the manual (Invitrogen; Cat. No. 11789013). Positive clones were selected on 2*TY plates with kanamycin. (50 µg/ml), and the plates scraped for preparation of the plasmids for transfer to pRAXdest#2 (expressionvector), with the Gateway LR reaction (Invitrogen; Cat. No. 11791019). This vector was digested with NotI, to optimize the transformation frequency of the LR reaction. Protoplast transformation has been used to create 9 CBH2 Regional Libraries in *A. niger* AP4 that were screened for altered thermostability (Table 17).

Example 6

Multiple Mutants

Based on the expression and thermostability results of the single site mutations, a set of multiple mutants was designed, which were produced in shake flasks only.

Mutations from CBH2 mutant FCA557 (P98L/M134V/S316P/S413Y) (from QC-libraries, Example 4) were combined (TABLE 9) with those from CBH2 mutants FCA 564 (S316P/V323Y), FCA568 (V206L/S210R/T214Y/S316P) and FCA570 (M134L/L144R/S316P) (from Region Libraries, Example 5), to obtain CBH2 molecules with improved thermal stability.

TABLE 9

| | P98L | M134L | M134V | L144R | V206L | S210R | S210L | T214Y | S316P | V323Y | S413Y |
|---|---|---|---|---|---|---|---|---|---|---|---|
| FCA572 | + | − | + | − | + | + | − | + | + | − | + |
| FCA573 | + | + | − | + | − | − | − | + | + | − | + |
| FCA574 | + | + | − | + | + | + | − | + | + | − | + |
| FCA575 | + | − | + | − | − | − | − | + | + | + | + |

TABLE 9-continued

|        | P98L | M134L | M134V | L144R | V206L | S210R | S210L | T214Y | S316P | V323Y | S413Y |
|--------|------|-------|-------|-------|-------|-------|-------|-------|-------|-------|-------|
| FCA576 | +    | −     | +     | −     | +     | +     | −     | +     | +     | +     | +     |
| FCA577 | +    | +     | −     | +     | −     | −     | −     | −     | +     | +     | +     |
| FCA578 | +    | +     | −     | +     | +     | +     | −     | +     | +     | +     | +     |
| FCA579 | +    | +     | −     | +     | −     | −     | +     | +     | +     | +     | +     |
| FCA580 | +    | +     | −     | +     | −     | +     | −     | +     | +     | +     | +     |

Primers were constructed and ordered from Invitrogen:

TABLE 10

| Primername | bps |
|---|---|
| S316P/V323Y-for | CCAGCCCCCCACCGTACACGCAAGGCAACGCTTACTACAAC GAGAAG |
| S316P/V323Y-rev | CTTCTCGTTGTAGTAAGCGTTGCCTTGCGTGTACGGTGGGG GGCTGG |
| S210R-for | CGTCAAATTGTCGTGGAATATCGCGATATCCGGTACCTCCTG GTTATTG |
| S210R-rev | CAATAACCAGGAGGTACCGGATATCGCGATATTCCACGACAA TTTGACG |
| S210L-for | CGTCAAATTGTCGTGGAATATCTCGATATCCGGTACCTCCTG GTTATTG |
| S210L-rev | CAATAACCAGGAGGTACCGGATATCGAGATATTCCACGACAA TTTGACG |
| V206L/S210R/T214Y-for | CGTCAAATTCTCGTGGAATATCGCGATATCCGGTACCTCCTG GTTATTG |
| V206L/S210R/T214Y-rev | CAATAACCAGGAGGTACCGGATATCGCGATATTCCACGAGAA TTTGACG |
| M134L/L144R-for | CCCTCTTTTCTGTGGCTAGATACTCTTGACAAGACCCCTCGC ATGGAGCAAACC |
| M134L/L144R-rev | GGTTTGCTCCATGCGAGGGGTCTTGTCAAGAGTATCTAGCCA CAGAAAAGAGGG |

PCR was performed using the reaction reagents in Table 11 (below), to obtain all fragments (A-M) needed to construct all 9 CBH2 combinatorials. The DNA polymerase Phusion (Finnzymes; Cat. No. F-530) was used. The primer concentration was 10 μM. The cycling conditions are given in Table 2 (above).

TABLE 11

|   |   | A | B | C | D | E | F | G | H | I | J | K | L | M |
|---|---|---|---|---|---|---|---|---|---|---|---|---|---|---|
|   | Template FCA557 (μl) | 1 | 1 | 1 | 1 | 1 | 1 | 1 | 1 | 1 | 1 | 1 | 1 | 1 |
|   | dNTP (10 mM) (μl) | 1 | 1 | 1 | 1 | 1 | 1 | 1 | 1 | 1 | 1 | 1 | 1 | 1 |
|   | 5* HF buffer (μl) | 10 | 10 | 10 | 10 | 10 | 10 | 10 | 10 | 10 | 10 | 10 | 10 | 10 |
|   | DMSO (μl) | 1.5 | 1.5 | 1.5 | 1.5 | 1.5 | 1.5 | 1.5 | 1.5 | 1.5 | 1.5 | 1.5 | 1.5 | 1.5 |
|   | Phusion enzyme (μl) | 0.5 | 0.5 | 0.5 | 0.5 | 0.5 | 0.5 | 0.5 | 0.5 | 0.5 | 0.5 | 0.5 | 0.5 | 0.5 |
| PRIMERS | CBH2-attB1 Forward | 2 | — | 2 | — | — | 2 | — | — | — | — | — | — | — |
|   | CBH2-attB2 Reverse | — | 2 | — | 2 | — | — | 2 | — | — | — | — | — | — |
|   | M134L/L144R-for | — | — | — | 2 | 2 | — | — | — | 2 | 2 | 2 | — | — |
|   | M134L/L144R-rev | — | — | 2 | — | — | — | — | — | — | — | — | — | — |
|   | S316P/V323Y-for | — | — | — | — | — | — | — | 2 | — | — | — | — | — |
|   | S316P/V323Y-rev | — | — | — | — | — | 2 | — | 2 | 2 | — | — | 2 | 2 |
|   | V206L/S210R/T214Y-for | — | 2 | — | — | — | — | — | 2 | — | — | — | — | — |
|   | V206L/S210R/T214Y-rev | 2 | — | — | — | 2 | — | — | — | — | — | — | — | — |
|   | 210R forward | — | — | — | — | — | — | — | — | — | — | — | — | 2 |
|   | 210R reverse | — | — | — | — | — | — | — | — | — | 2 | — | — | — |
|   | 210L Forward | — | — | — | — | — | — | — | — | — | — | — | 2 | — |
|   | 210L Reverse | — | — | — | — | — | — | — | — | — | — | 2 | — | — |
|   | Sterile MilliQ water | 32 | 32 | 32 | 32 | 32 | 32 | 32 | 32 | 32 | 32 | 32 | 32 | 32 |

PCR fragments were put on a 1% LMT gel, and purified with a Qiagen Gel Extraction Kit (Strategene Cat. No. 28706). The purified fragments were fused using Phusion DNA polymerase (see above) with the CBH2-attB primers (above), to obtain the complete CBH2 combinatorials according to Table 12.

TABLE 12

| Mutant nr. | PCR nr. | Final mutations |
|---|---|---|
| FCA572 | A | P98L + M134V + V206L + S210R + T214Y + S316P + S413Y |
|  | B |  |
| FCA573 | C | P98L + M134L + L144R + S316P + S413Y |
|  | D |  |
| FCA574 | C | P98L + M134L + L144R + V206L + S210R + T214Y + S316P + S413Y |
|  | E |  |
|  | B |  |
| FCA575 | F | P98L + M134V + S316P + V323Y + S413Y |
|  | G |  |
| FCA576 | A | P98L + M134V + V206L + S210R + T214Y + S316P + V323Y + S413Y |
|  | H |  |
|  | G |  |
| FCA577 | C | P98L + M134L + L144R + S316P + V323Y + S413Y |
|  | I |  |
|  | G |  |
| FCA578 | C | P98L + M134L + L144R + V206L + S210R + T214Y + S316P + V323Y + S413Y |
|  | E |  |
|  | H |  |
|  | G |  |
| FCA579 | C | P98L + M134L + L144R + S210L + T214Y + S316P + V323Y + S413Y |
|  | K |  |
|  | L |  |
|  | G |  |
| FCA580 | C | P98L + M134L + L144R + S210R + T214Y + S316P + V323Y + S413Y |
|  | J |  |
|  | M |  |
|  | G |  |

Complete CBH2-attB molecules were purified from 1% LMT agarose and transferred to the *A. niger* AP4 expression vector pRAXdest#2. The method used was the "One-tube Protocol for cloning attB-PCR products directly into destination vectors" (according Invitrogen's manual).

Three microliters μl of the reaction sample was used for transformation of 100 μl DH5α max. efficiency competent cells (Invitrogen Cat. No. 18258012), according the manual. After 1 hour of growth at 37° C. in SOC medium, the cells were plated on selective ampicillin plates (100 μg/ml), and incubated at 37° C. overnight. Positive clones were grown in 2*TY medium and 100 μg/ml ampicillin. Plasmid DNA was isolated with QIAprep Spin Miniprep Kit (Qiagen Cat. No. 27106) and sequenced.

Mutants with the right sequence were transferred to the *A. niger* expression vector pRAXdest#2 with the LR reaction, according the Gateway Cloning procedure (Invitrogen; Cat. No. 11791019). After protoplast transformation of the expression clones to *A. niger* AP4, the Multiple Mutants were expressed and isolated (as in Example 7), and analyzed for thermostability (Tables 18, 19).

Example 7

Expression and Isolation of CBH2 and its Variants from Shake Flask Growths

To provide materials for Tm measurements in thermal denaturation studies (Example 9), expression clones were grown in shake flasks and then the CBH2 molecules purified, as follows:

Cells were transformed with an expression vector comprising a variant CBH2 cellulase encoding nucleic acid. The constructs were transformed into *A. niger* var. *awamori* according to the method described by Cao et al (Cao Q-N, Stubbs M, Ngo K Q P, Ward M, Cunningham A, Pai E F, Tu G-C and Hofmann T (2000) Penicillopepsin-JT2 a recombinant enzyme from *Penicillium janthinellum* and contribution of a hydrogen bond in subsite S3 to kcat Protein Science 9:991-1001).

*A. niger* var *awamori* transformants were grown on minimal medium lacking uridine (Ballance et al. 1983). Transformants were grown by inoculating 1 cm² of spore suspension from the sporulated grown agar plate into 100 ml shake flasks for 3 days at 37° C. as described by Cao et al. (2000), and then screened for cellulase activity.

The CBH2 activity assay was based on the hydrolysis of the Phosphoric Acid Swollen Cellulose (PASC: 0.5% PASC in 0.5 mM Na acetate, pH 4.85). Reducing sugars were measured by PAHBAH assay. (PAHBAH: 2.975 g PAHBAH, 9.75 g Na—K-tartrate in 195 ml 2% NaOH). PASC: (Karlsson, J. et al. (2001), Eur. J. Biochem, 268, 6498-6507, Wood, T. (1988) in Methods in Enzymology, Vol. 160. Biomass Part a Cellulose and Hemicellulose (Wood, W. & Kellog, S. Eds.), pp. 19-25, Academic Press, San Diego, Calif., USA) and PAHBAH: (Lever, M. (1972) Analytical Biochemistry, 47, 273, Blakeney, A. B. & Mutton, L. L. (1980) Journal of Science of Food and Agriculture, 31, 889, Henry, R. J. (1984) Journal of the Institute of Brewing, 90, 37)

Cel6A wild type and variants were then purified from cell-free supernatants of these cultures by hydrophobic interaction chromatography (HIC) by one of two procedures:

For SDM variants (Example 3), Bio-RAD Poly-Prep Columns CAT#731-1550 were used with Pharmacia Phenyl Sepharose resin (1.6 ml=1 ml column) CAT #17-0973-05. The resin was allowed to settle before washing with 1-2 column volume (CV) water, then equilibrated with 5 CV of 0.020 M sodium phosphate, 0.5 M ammonium sulfate, pH6.8 (Buffer A). 4M Ammonium sulfate was added to the supernatants to a final concentration of approximately 0.5 M. 2 CV of supernatant was loaded and the column then washed with 5 CV of Buffer A, before elution with 4 CV of 0.020 M sodium phosphate, pH6.8. The filtrate contained purified CBH2.

For Multiple Mutants (Example 6), columns were run on Novagen vacuum manifold using Poros® 20 HP2 resin made by Applied Biosystems. HIC columns were equilibrated with 5 CV of Buffer A. Ammonium sulfate was added to the supernatants to a final concentration of approximately 0.5 M and the pH adjusted to 6.8. After filtration, the supernatant was loaded, the column washed with 10 CV of Buffer A and then eluted with a 10 CV of 0.020 M sodium phosphate, pH 6.80. Fractions were collected and pooled on the basis of the presence of CBH2, as detected by reduced, SDS-PAGE gel analysis.

When desired, CBH2 molecules are de-glycosylated prior to purification by treatment of the supernatant with Endoglycosidase H according to the supplied protocol (Sigma-Aldrich).

Example 8

Thermostability of CBH2 Variants by Thermal Inactivation

CBH2 molecules with altered stability to irreversible thermal inactivation compared to wild type CBH2 were identified by measurement of the PASC activity of equal aliquots of cell-free supernatants before and after incubation at elevated temperature under stringent conditions. The stringent conditions used were 1 hour incubation at either 61° C. or 65° C. (as indicated) of a 1:1 dilution of supernatant in 0.1 M sodium acetate, pH4.85, followed by cooling on ice for 10 minutes. The % residual activity (% remaining activity after incubation at elevated conditions) was calculated by dividing the residual activity by the initial activity (CBH2 activity on PASC before stringency incubation).

Screening of CBH2 variants and wild type for stability to thermal inactivation was performed according to the following protocols:

A. Solutions and Media

The following solutions/media were used in the determination of the CBH2 mutants stability to irreversible thermal inactivation:

1. Minimal medium plus maltose (MM medium) was prepared as shown in Table 13:

TABLE 13

| | Minimal medium + maltose for *A. niger* | | |
|---|---|---|---|
| 1 | MM maltose medium minimal (liquid medium with maltose) | 6 g<br>0.52 g<br>1.52 g | $NaNO_3$<br>KCl<br>$KH_2PO_4$ |
| | | \multicolumn{2}{l}{Adjust to ca. 800 ml with MilliQ water, autoclave and cool to 50° C.} |
| | | \multicolumn{2}{l}{Add per liter the following sterilized solutions:} |
| | | 1 ml | Trace-elements-LW solution (see 2) |
| | | 2.5 ml | 20% $MgSO_4 \cdot 7H_2O$ stock solution |
| | | 50 ml | 50% maltose stock solution (final conc.: 2.5%) |
| | | 20 ml | 100 $mg/ml$ arginine stock (final conc.: 2 $g/l$) |
| | | 20 ml | methionine (50 g/l)/ biotine(0.2 g/l) stock |
| | | 20 ml | 1M phosphate buffer pH 5.8 (see 3) |
| | | \multicolumn{2}{l}{Optional: addition of 1 ml 50 $mg/ml$ streptomycine} |
| | | \multicolumn{2}{l}{For *A. niger* host: add 10 ml 200 $mg/ml$ uridine stock (final conc.: 2 $g/l$).} |
| | | \multicolumn{2}{l}{Adjust to 1 liter with distilled water and filter sterilize (0.2 µm)} |
| 2 | Trace-elements-LW (L. Wilson) | 1 g<br>8.8 g<br>0.4 g<br>0.15 g<br>0.1 g<br>50 mg<br>250 ml<br>0.20 ml | $FeSO_4 \cdot 7H_2O$<br>$ZnSO_4 \cdot 7H_2O$<br>$CuSO_4 \cdot 5H_2O$<br>$MnSO_4 \cdot 4H_2O$<br>$Na_2B_4O_7 \cdot 10H_2O$<br>$(NH_4)_6Mo_7O_{24} \cdot 4H_2O$<br>distilled water, swirl and add:<br>concentrated HCl to dissolve crystals (4N) |
| | | \multicolumn{2}{l}{Adjust to 1 liter with distilled water and filter sterilize (0.2 µm)} |
| 3 | Phosphate buffer pH 5.8 | | 1M $K_2HPO_4$<br>1M $KH_2PO_4$ |
| | | \multicolumn{2}{l}{Mix both solutions until the pH = 5.8 and filter sterilize (0.2 µm)} |

2. 0.5% PASC solution in 50 mM NaAc pH 4.85:
   i. Add 5 gram Avicel PH101 (Fluka 11365) to a 1 liter beaker glass and add ~12 ml water to make a thick slurry.
   ii. Place beaker on ice.
   iii. Add 150 ml ice-cold 85% ortho-phosphoric acid (Art. 1000573 Merck) and mix with the ultra turrax at high speed (prevent splashing) for about 1 hour.
   iv. Add 100 ml ice-cold acetone, which causes a slow precipitation of the amorphous cellulose to a very thick slurry. Eventually use a spatula for better mixing.
   v. Dilute the very thick slurry to ~1 liter with water to make it fluid enough to transfer it to 6×250 ml Sorvall containers.
   vi. Spin down 15 minutes at 10 k and discard the supernatant.
   vii. Mix pellets with as much water as the beakers can contain and spin down again.
   viii. Repeat step 5 and 6 at least for 3 times until the pH has increased to pH4.0-5.0.
   ix. To increase the washing of the phosphoric acid a drop of NaOH 4N can be added to the water.
   x. Mix the last pellets with water to ~300 ml and homogenize.
   xi. Determine the concentration of the slurry with dry weight measurement.

Sterilize the slurry for 20 minutes at 121° C. Cool down and store in the refrigerator.

3. PAHBAH reagents were prepared as follows: 1.5 g PAHBAH+5 g Sodium-Potassium-tartrate in 100 ml 2% NaOH 4. Cellobiose stock solutions; In MQ water prepare a 0, 0.01, 0.05, 0.1, 0.2, 0.5, 0.7 and a 1 mg/ml solution.

B. Sample Preparation

1. Grow *A. niger* variants in 96 W filter MTP's (Millipore, # MAGVS2210), containing 200 μl minimal medium +maltose (above) per well for 7 days at 33° C., on an orbital shaker (225 rpm) with 80-90% humidity.

2. After growth incubation, filter the cultures using a vacuum manifold, collecting the filtrate (supernatant) in a fresh 96 W flat MTP's (Greiner, #655101), store at 4° C.

C. Stringency Incubation at Elevated Temperatures

1. Dilute 60 μl supernatant (sup) per well with 60 μl 100 mM NaAc pH 4.85 (1:1).

(Optional: When remaining supernatant needs to be checked for residual sugars, add 190 μl 100 mM NaAcpH4.8 to 10 μl sup per well and transfer 20 μl of this diluted supernatant to 150 μl PAHBAH reagents to do the PAHBAH reducing sugar assay (see E)

2. Transfer 20 μl diluted supernatant to a fresh flat 96 W MTP and store at 4° C. (for initial activity)

3. Incubate remain diluted supernatant (ca. 1000) for 1 hr at 61° C. (or 65° C.) (for residual activity)

4. Cool down on ice for 10'.

D. PASC Incubation; Small Scale Conversion (SSC) Assay

1. Prepare in fresh flat MTP's: 180 μl/well of a well-stirred 0.5% PASC-solution in 50 mM NaAc, pH4.85.

2a. In one plate designed to measure residual activity, transfer (with mixing up and down) per well 200 treated diluted supernatant (sup) after pre-incubation to the PASC-MTP's.

2b. In a second plate designed to measure initial activity, transfer (with mixing up and down) per well 1800 PASC-solution to the stored 20 μl untreated diluted supernatant.

3. Seal the sup-PASC MTP's and incubate for 2 hrs at 50°, stirring 900 rpm.

4. Cool down on ice for 10'.

5. Transfer the sup-PASC mix to a fresh filter MTP, filter in a vacuum manifold and collect the filtrate.

E. PAHBAH Reducing Sugar Assay

1. Prepare a fresh 96 W flat MTP with 150 μl PAHBAH reagents per well.

2. Transfer 20 μl of the sup-PASC filtrate to the PAHBAH (mixing up and down)

3. Put a calibration line in column 1 in first MTP; 20 μl of the cellobiose stock solutions (see A4, above)

4. Incubate for 1 hr at 69° C., 900 rpm, cool down to room temperature and spin down at 2000 rpm for 2'.

5. Measure endpoint OD410 in MTP reader directly in SpectraMax spectrophotometer (Spectra, Sunnyvale, Calif., U.S.A.)

F. Data Processing (Spad-it)

1. From the readings on the cellobiose dilution wells, plot a cellobiose calibration line in mg/ml cellobiose vs. OD410

2. Use calibration curve and the readings from the sample wells to calculate, in mg/ml cellobiose, the initial and residual values for each sup 3. Calculate % residual activity Residual Activity Measurements for CBH2 Variants from Site Directed Mutagenesis

TABLE 14

Cel6A Wild-Type and Variants Residual Activity

| mutation | % res. 1 hr 61° C. | stdev | % res. 1 hr 65° C. | stdev |
|---|---|---|---|---|
| V94E | 18.9 | 1.4 | 10.8 | 4.8 |
| P98L | 30.1 | 0.6 | 11.2 | 1.8 |
| G118P | 10.4 | 0.6 | 7.4 | 1.7 |
| w.t. | 21.1 | 4.1 | 8.6 | 0.4 |
| M120L | 19.8 | 0.3 | 9.9 | 2.2 |
| M134V | 27.5 | 2.1 | 9.7 | 1.3 |
| T142V | 22.5 | 1.0 | 6.1 | 1.4 |
| T148Y | 16.8 | 2.9 | 13.7 | 2.7 |
| L179A | 20.0 | 0.5 | 4.7 | 0.2 |
| V206L | 21.1 | 2.8 | 7.7 | 1.6 |
| I212V | 23.3 | 1.9 | 11.6 | 4.1 |
| w.t. | 20.0 | 1.5 | 5.6 | 1.2 |
| L215I | 26.6 | 1.3 | 5.2 | 1.0 |
| G231N | 23.2 | 0.5 | 5.3 | 1.1 |
| T232V | 24.1 | 1.4 | 4.3 | 0.5 |
| V250I | 17.8 | 0.6 | 5.7 | 0.5 |
| N285Q | 15.7 | 3.9 | 6.6 | 2.5 |
| S291G | 18.3 | 0.2 | 4.6 | 0.0 |
| T312S | 15.7 | 0.2 | 6.8 | 0.3 |
| w.t. | 21.1 | 1.3 | 5.7 | 0.7 |
| S316P | 37.7 | 0.5 | 9.5 | 1.5 |
| V323N | 10.3 | 0.6 | 6.7 | 0.2 |
| N325D | 20.8 | 0.6 | 5.2 | 0.1 |
| I333L | 14.6 | 1.8 | 14.7 | 1.1 |
| T349L | 13.0 | 2.8 | 10.1 | 2.9 |
| A381T | 17.1 | 1.0 | 4.7 | 0.4 |
| S386P | 21.5 | 0.7 | 4.3 | 1.0 |
| w.t. | 20.2 | 1.1 | 5.3 | 1.1 |
| F411Y | 24.4 | 2.2 | 5.2 | 1.3 |
| S413Y | 39.1 | 1.0 | 8.2 | 0.6 |
| A416G | 7.0 | 0.7 | 5.8 | 0.4 |
| A429T | 15.8 | 1.8 | 6.3 | 0.5 |
| M145L | 9.3 | 2.2 | 9.5 | 3.4 |
| Q204E | 21.7 | 0.9 | 6.4 | 0.9 |
| Q276L | 10.1 | 1.4 | 4.8 | 0.6 |
| w.t. | 22.9 | 1.6 | 7.5 | 1.1 |
| G308A | 20.0 | 2.1 | 4.5 | 0.1 |
| G334A | 22.8 | 2.1 | 4.3 | 0.9 |
| S343P | 23.8 | 0.3 | 4.6 | 0.1 |
| G360R | 8.5 | 0.2 | 6.1 | 0.6 |
| S380T | 15.8 | 0.2 | 4.5 | 0.8 |
| Q426E | 28.7 | 1.5 | 3.7 | 0.5 |
| T312S | 18.9 | 2.7 | 9.2 | 3.7 |
| w.t. | 23.3 | 2.3 | 6.7 | 0.9 |
| S316P | 43.9 | 2.2 | 8.1 | 0.8 |
| I333L | 13.2 | 0.5 | 11.1 | 0.9 |
| S413Y | 43.0 | 1.4 | 6.1 | 1.4 |
| A416G | 9.6 | 0.7 | 6.1 | 0.3 |

Each Wild Type (w.t.) and variant % residual activity number is the average of 3 determinations. stdev = calculated standard deviation for the determinations.

The above table shows the % residual activity remaining for the single site directed mutants (SDM, Example 3) after 1 hour stringency incubation at 61° C., or at 65° C. The residual activities of the WT clones are shown in every subset of the data (there was one WT reference on every plate). The average value for the WT was 21.4% and 6.6% at 61° C. and 65° C., respectively. It is clear that every mutant with a residual activity higher than WT is a molecule with improved thermostability under the screening conditions.

Residual Activity Measurements for CBH2 Combinatorial Mutants

The two results columns in Tables 15 and 16 show the % residual activities after incubation at two different temperatures for the variants produced as in Example 4.

Two tables (Tables 15 AND 16) are presented below because the values were generated in two independent experiments.

It is clear that every mutant with a residual activity higher than WT is a molecule with improved thermostability under the screening conditions.

TABLE 15

Residual Activities for Cel6A Wild Type and Variants

| | % res. 1 hr 61° C. | stdev | % res. 1 hr 65° C. | stdev |
|---|---|---|---|---|
| P98L/M134V/T154A/V206L/I212V/S316P/F411Y/S413Y | 51.8 | 2.5 | 10.6 | 2.2 |
| P98L/T154A/I212V/F411Y | 12.1 | 1.0 | 0.0 | 0.6 |
| P98L/M134V/I212V/T312S/S316P/S413Y | 51.0 | 3.8 | 9.6 | 0.9 |
| P98L/M134V/T154A/I212V/T312S/S316P/S413Y | 41.0 | 5.2 | 0.0 | 1.0 |
| S316P/S413Y | 46.5 | 4.6 | 6.8 | 0.7 |
| P98L/M134V/T154A/V206L/S316P | 43.0 | 2.3 | 0.0 | 2.3 |
| P98L/M134V/S316P/S413Y | 50.6 | 2.0 | 12.4 | 1.7 |
| P98L/M134V/V206L/S316P/S413Y | 54.4 | 3.3 | 13.3 | 2.4 |
| P98L/M134V/T154A/I212V/S316P/F411Y/S413Y | 44.6 | 0.4 | 0.0 | 1.2 |
| P98L/M134V/S316P | 40.6 | 4.4 | 0.0 | 1.3 |
| P98L/M134V/T154A/T312S | 37.7 | 4.6 | 0.0 | 2.2 |
| w.t. | 14.9 (8) | 4.5 | 0 (8) | 1.5 |
| P98L/M134V/T154A/I212V/S316P/S413Y | 51.2 (8) | 2.7 | 12.1 (8) | 2.1 |

Unless otherwise indicated, the average % residual activities were calculated from 4 determinations. Where indicated, "(8)", 8 determinations were made. stdev = calculated standard deviation for the determinations.

TABLE 16

Residual Activities for Cel6A Wild Type and Variants

| | % res. 1 hr 61° C. | stdev | % res. 1 hr 65° C. | stdev |
|---|---|---|---|---|
| P98L/M134V/I212V/S316P/S413Y | 56.7 (1) | | 13.2 (1) | |
| w.t. | 19.1 (8) | 2.6 | 0.3 (8) | 1 |
| P98L/M134V/T154A/I212V/S316P/S413Y | 63.9 (8) | 3.6 | 23.4 (8) | 7.5 |

The average % residual activities were calculated from the number of determinations indicated in parentheses. stdev = calculated standard deviation for the determinations.

Residual Activity Measurements for CBH2 Variants from Regional Mutagenesis

Table 17 shows the % residual activity after incubation at 61° C. for the variants produced as in Example 5.

TABLE 17

Residual Activities for Cel6A Wild Type and Variants

| | % res. 1 hr 61° C. | stdev |
|---|---|---|
| S316P/V323L | 44.4 | 10.0 |
| S316P/V323Y | 49.0 | 12.1 |
| V206L/S210R/S316P | 49.2 | 5.0 |
| V206L/S316P | 49.2 | 5.0 |
| V206L/S210L/T214M/S316P | 84.0 | 19.7 |
| V206L/S210R/T214Y/S316P | 69.3 | 15.9 |
| M134G/L144G/S316P | 93.5 | 6.1 |
| M134L/L144R/S316P | 70.6 | 4.2 |
| M134L/L144S/S316P | 62.0 | 15.0 |
| w.t. | 23.9 (32) | 4.8 |
| S316P | 44.2 (32) | 7.7 |

Unless otherwise indicated, each % residual activity number is the average of three determinations. Where indicated, "(32)", 32 determinations were made. stdev = calculated standard deviation for the determinations.

It is obvious that every mutant with a residual activity higher than WT and/or S316P is a molecule with improved thermostability under the screening conditions.

Example 9

Thermostability of CBH2 Variants by Tm Measurements

CBH2 cellulase mutants were cloned, expressed and purified as above (Example 7). Thermal denaturation data was collected on a VP-DSC microcalorimeter from Microcal (Nothampton, Mass., US). Buffer conditions were 50 mM Bis Tris Propane/50 mM ammonium acetate/glacial acetic acid at pH 5.5 or at pH5.0, as indicated. The protein concentrations were approximately 0.25 mgs/ml. Three thermal scans were performed from 25° C.-80° C. at a scan rate of 90 (° C./hr). The first scan showed thermal denaturation of the CBH2 and was used to determine the apparent mid-point of thermal denaturation, Tm: The instrument software generates a Cp (cal/° C.) versus Temperature (° C.) curve and the Tm was determined manually from this curve. The thermal denaturation was irreversible in all cases, as shown by the absence of thermal denaturation in the second and third thermal scans.

TABLE 18

Tm's by DSC at pH 5.5.

| FCA | Variant | Tm G | Tm DG | ΔTm |
|---|---|---|---|---|
| 500 | WT | 66.6 | | |
| 500 | WT | 66.5 | | |
| 502 | P98L | 67.1 | | 0.6 |
| 502 | P98L | 66.9 | | 0.4 |
| 505 | M134V | 66.9 | | 0.3 |
| 505 | M134V | 66.7 | | 0.2 |
| 522 | T312S | 64.1 | | −2.4 |
| 522 | T312S | 64.5 | | −2.1 |
| 522 | T312S | 64.1 | | −2.5 |
| 523 | S316P | 68.0 | | 1.5 |
| 523 | S316P | 67.9 | | 1.3 |
| 523 | S316P | 67.6 | | 1.0 |
| 535 | S413Y | 66.8 | | 0.2 |
| 535 | S413Y | 66.7 | | 0.2 |
| 536 | A416G | 65.9 | | −0.6 |
| 536 | A416G | 65.6 | | −1.0 |
| 540 | P98L/M134V/V206L/F411Y | 67.2 | | 0.6 |
| 541 | P98L/M134V/V206L/I212V/S316P/F411Y | 68.5 | | 1.9 |
| 542 | I212V/S316P/F411Y | 67.6 | | 1.1 |
| 543 | P98L/M134V/T154A/I212V/S316P/S413Y | 71.4 | | 4.9 |
| 543 | P98L/M134V/T154A/I212V/S316P/S413Y | 71.8 | | 5.2 |
| 544 | V206L/I212V/S316P | 68.2 | | 1.7 |
| 545 | V206L/I212V/T312S/S316P | 67.8 | | 1.3 |
| 546 | V206L/I212V/T312S/S316P/S413Y | 69.8 | | 3.2 |
| 547 | V206L/I212V/T312S/S316P/F411Y/S413Y | 69.0 | | 2.5 |
| 548 | M134V/V206L/I212V/T312S/S316P/F411Y/S413Y | 69.2 | | 2.7 |
| 549 | P98L/V206L/I212V/T312S/S316P/F411Y/S413Y | 69.5 | | 3.0 |
| 550 | P98L/M134V/V206L/I212V/T312S/S316P/S413Y | 69.9 | | 3.4 |
| 509 | T154A | | 66.8 | 0.2 |
| 543 | P98L/M134V/T154A/I212V/S316P/S413Y | | 71.0 | 4.4 |
| 546 | V206L/I212V/T312S/S316P/S413Y | | 69.6 | 3.0 |
| 551 | P98L/M134V/T154A/V206L/I212V/S316P/F411Y/S413Y | | 71.2 | 4.6 |
| 552 | P98L/T154A/I212V/F411Y | | 66.4 | −0.2 |
| 555 | S316P/S413Y | | 70.5 | 3.9 |
| 556 | P98L/M134V/T154A/V206L/S316P | | 68.9 | 2.3 |
| 557 | P98L/M134V/S316P/S413Y | | 71.3 | 4.7 |
| 558 | P98L/M134V/V206L/S316P/S413Y | | 71.2 | 4.6 |
| 559 | P98L/M134V/T154A/I212V/S316P/F411Y/S413Y | | 69.8 | 3.2 |
| 560 | P98L/M134V/S316P | | 68.7 | 2.1 |
| 561 | P98L/M134V/T154A/T312S | | 69.1 | 2.5 |
| 562 | P98L/M134V/I212V/S316P/S413Y | | 71.2 | 4.6 |
| 563 | S316P/V323L | | 67.9 | 1.3 |
| 564 | S316P/V323Y | | 68.7 | 2.1 |
| 565 | V206L/S210R/S316P | | 68.3 | 1.7 |

TABLE 18-continued

Tm's by DSC at pH 5.5.

| FCA | Variant | Tm G | Tm DG | ΔTm |
|---|---|---|---|---|
| 566 | V206L/S316P | | 68.3 | 1.7 |
| 567 | V206L/S210L/T214M/S316P | | 68.7 | 2.1 |
| 568 | V206L/S210R/T214Y/S316P | | 69.1 | 2.5 |
| 569 | M134G/L144G/S316P | | 66.1 | −0.5 |
| 570 | M134L/L144R/S316P | | 69.7 | 3.1 |
| 571 | M134L/L144S/S316P | | 69.4 | 2.8 |
| 573 | P98L/M134L/L144R/S316P/S413Y | | 71.8 | 5.2 |
| 575 | P98L/M134V/S316P/V323Y/S413Y | | 70.8 | 4.2 |
| 577 | P98L/M134L/L144R/S316P/V323Y/S413Y | | 71.8 | 5.2 |

All of the variant data is referenced to the still glycosylated FCA500 (rCBH2 wild type) Tm. "Tm G" = Tm measured on recombinant protein as purified. "Tm DG" = Tm measured on recombinant protein de-glycosylated with EndoH before being purified.

TABLE 19

Tm's by DSC at pH 5.0.

| FCA | Variant | Tm G | Tm DG | ΔTm |
|---|---|---|---|---|
| 500 | WT | 67.2 | 66.9 | |
| 500 | WT | 67.1 | | |
| 502 | P98L | 67.7 | | 0.6 |
| 505 | M134V | 67.5 | | 0.3 |
| 522 | T312S | 64.9 | | −2.2 |
| 523 | S316P | 68.4 | | 1.3 |
| 523 | S316P | 68.4 | | 1.3 |
| 535 | S413Y | 67.5 | | 0.3 |
| 536 | A416G | 66.4 | | −0.7 |

All of the variant data is referenced to the still glycosylated FCA500 (rCBH2 wild type) Tm. "Tm G" = Tm measured on recombinant protein as purified. "Tm DG" = Tm measured on recombinant protein de-glycosylated with EndoH before being purified.

The mutations introduced into the CBH2 cellulase mutants affected the thermal stability of the mutant CBH2 cellulase compared to wild type.

De-glycosylated proteins used in this Example and the following Examples were prepared using procedures well known in the art for removal of N-linked glycans (see, for example, Biochem. J. (2001) 358:423-430). See also Tai, T., et al. *J. Biol. Chem.* (1975) 250, 8569.

Example 10

Specific Activity of CBH2 Variants on PASC

This example examines the specific performance on phosphoric acid swollen cellulose of CBH2 variants as compared to wild-type *H. jecorina* CBH2 that had been cloned into *A. niger*.

Phosphoric acid swollen cellulose (PASC)—PASC was prepared from Avicel according to the method described in Walseth (1971) Tappi 35: 228 (1971) and Wood Biochem J. 121:353 (1971). This material was diluted with buffer and water to achieve a 1% w/v mixture such that the final concentration of sodium acetate was 50 mM, pH 5.0.

The relative specific performance of these variants on cellulosic substrates was determined by techniques known in the art. See, for example, Baker et al, Appl Biochem Biotechnol 1998 Spring; 70-72( ):395-403.

A standard cellulosic conversion assay was used in the experiments. See Baker, supra. In this assay enzyme and buffered substrate were placed in containers and incubated at a temperature over time. The reaction was quenched with enough 100 mM Glycine, pH 11.0 to bring the pH of the reaction mixture to at least pH10. Once the reaction was quenched, an aliquot of the reaction mixture was filtered through a 0.2 micron membrane to remove solids. The filtered solution was then assayed for soluble sugars by HPLC according to the methods described in Baker et al., Appl. Biochem. Biotechnol. 70-72:395-403 (1998).

The relative specific activity of these variants was determined with 1% PASC in 50 mM NaOAc pH 5.0 at 53° C. with 1400 rpm shaking for 3.5 hours. The enzymes were dosed at 0.75, 1.5, and 3 mg/gram of cellulose. The protein concentration was determined by OD 280 as in Leach and Scheraga 1960 (J. Am. Chem. Soc. 82:4790-4792). Variants that were compared were FCA500.3, FCA523, FCA536, and FCA540-550. For simplicity, FIG. 8 only shows FCA540, FCA542, FCA545, FCA547, FCA549, and FCA550. All other variant samples had specific activities bounded by the lines defined by the FCA542 and FCA545 results.

Several of the new CBH2 variants from the temperature stability screen are as active as wild type.

Figure 9:
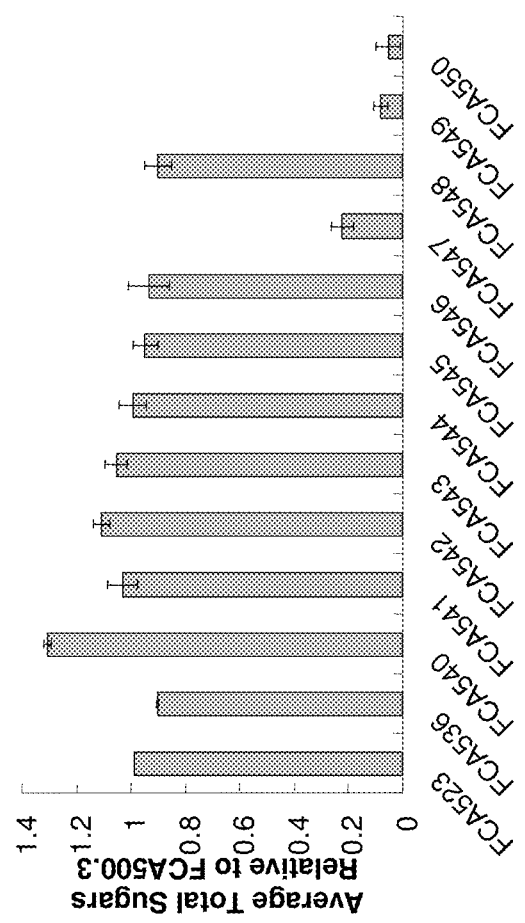
FIG. 9 is a bar graph of the ratio of the (average) total sugar produced by a variant and (average) total sugar produced by wild-type CBH2 as measured on PASC.

To compare the numbers from the dose dependent data above (as shown in FIG. 8), the ratio of the (average) total sugar produced by a variant and (average) total sugar produced by FCA500.3 (wild-type) at the same dose were averaged. These ratios, presented in FIG. 9, are all very similar except for the much less active FCA547, FCA549 and FCA550. The error bars are single standard deviation of the average of the ratios. A ratio of 1 would indicate that the variant has similar activity to the wild-type in this assay. All of the stabilized variants retained activity on this substrate.

Example 11

Specific Activity of CBH2 Variants on PCS

This example compares the specific activity on pretreated corn stover of the CBH2 variants as compared to wild-type *H. jecorina* CBH2 that had been cloned into *A. niger*.

Figure 10:
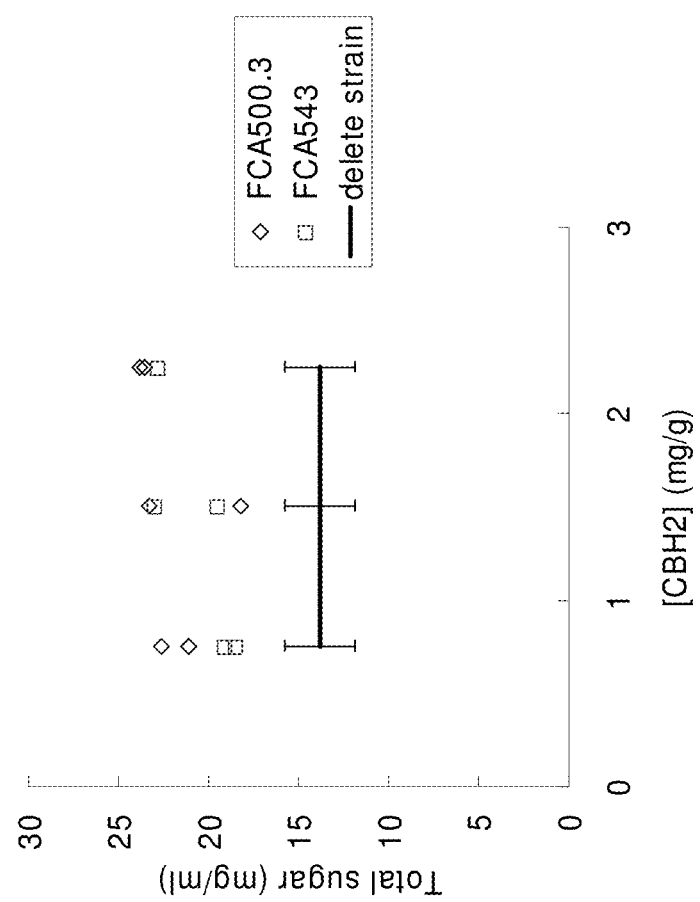
FIG. 10 is a graph showing the amount of sugar released by varying amounts of enzyme. Wild-type enzyme is denoted as FCA500.3 (open diamonds) and the variant is FCA543 (P98L/M134V/T154A/I212V/S316P/S413Y) (open squares). The broth from a CBH2-deleted strain served as a control.

Pretreated corn stover (PCS)—Corn stover was pretreated with 2% w/w $H_2SO_4$ as described in Schell, D. et al., J. Appl. Biochem. Biotechnol. 105:69-86 (2003) and followed by multiple washes with deionized water to obtain a paste having a pH of 4.5. Sodium acetate buffer (pH 5.0) was then added (to a final concentration of 50 mM sodium acetate) and, if necessary, this mixture was then titrated to pH 5.0 using 1N NaOH. The cellulose concentration in the reaction mixture was approximately 7%. The specific performance of the CBH2 was tested using PCS at 53° C. with 700 rpm for 20 hours. Three different doses of CBH2 variants, 0.75, 1.5 and 2.5 mg/g cellulose (in the PCS) were added to 8.5 mg CBH2-deleted cellulase strain broth/g cellulose. (For a discussion of deleting the CBH2 gene in *Hypocrea jecorina* (also referred to as *Trichoderma reesei*) see U.S. Pat. Nos. 5,861,271 and 5,650,322.) Results are shown in FIG. 10. The baseline activity of the CBH2-deleted strain (with no CBH2 added back) is shown. The CBH2 variant has similar activity to the CBH2 wild-type in a reconstituted whole cellulase on PCS. This shows that wild-type when added back to a deleted strain gives a certain activity above the deleted strain. The variant reaches approximately the same activity under similar conditions.

Figure 11:
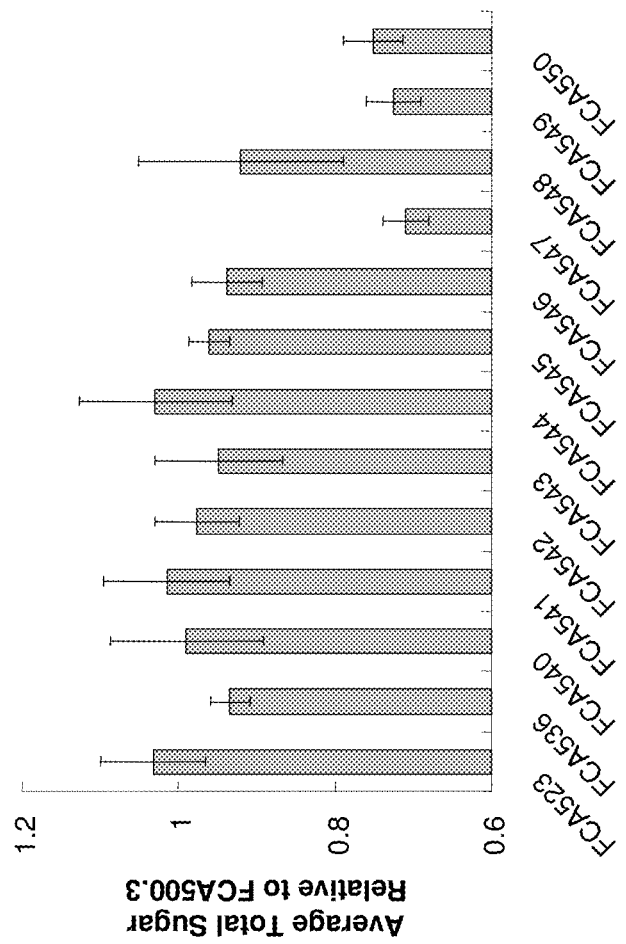
FIG. 11 is a bar graph of the ratio of the (average) total sugar produced by a variant and (average) total sugar produced by wild-type CBH2 as measured on pre-treated corn stover. The minimum scale value of the y-axis is 0.6 representing the value of the (average) total sugar produced by CBH2-delete strain divided by the (average) total sugar produced by the wild-type CBH2 in combination with the CBH2-delete strain. A value of 1 represents a level of activity similar to wild-type.

Similar assays were run for other variants as described above. The values of total sugar for duplicates were averaged at each dose then divided this value by the average of the corresponding duplicates for FCA500.3 (wild-type). These ratios, presented in FIG. 11, are all very similar except for the much less active FCA547, FCA549 and FCA550. The error bars are single standard deviation of the ratios at different doses. A ratio of 1 would indicate that the variant has similar

Example 12

CBH2 Variant Specific Activity at Various Temperatures

This example demonstrates how long each of the enzymes (stabilized variants and wild-type) remained active at various temperatures.

The assays described in Example 10 were used in this Example as modified below. Total sugar produced by CBH2 (0.5 mg/g cellulose) in 1% PASC at 53, 65, and 75° C. with 300 RPM shaking over various incubation times was used to determine how long each of these enzymes (stabilized variants and wild-type) remained active at these temperatures.

Figure 12:
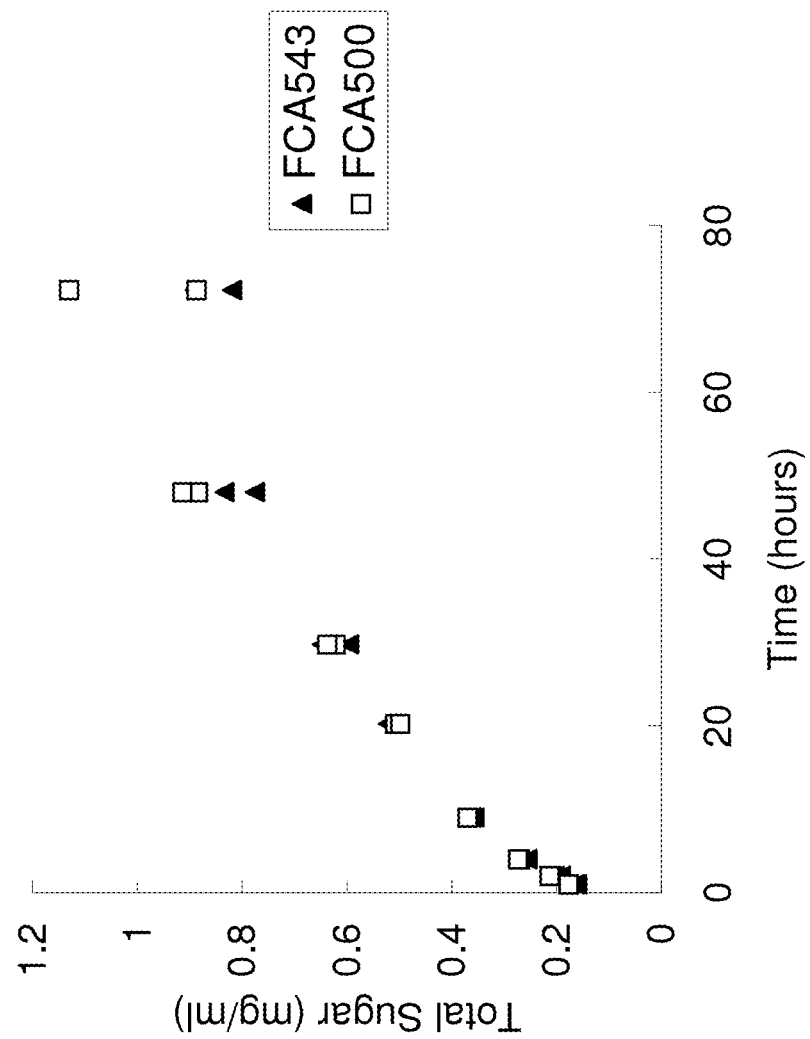
FIG. 12 is a graph of a time course experiment. Total sugar released from PASC by a CBH2 molecule over time at 53° C. is shown. Variant is shown as filled triangles (▲); wild-type as open squares (□).
Figure 13:
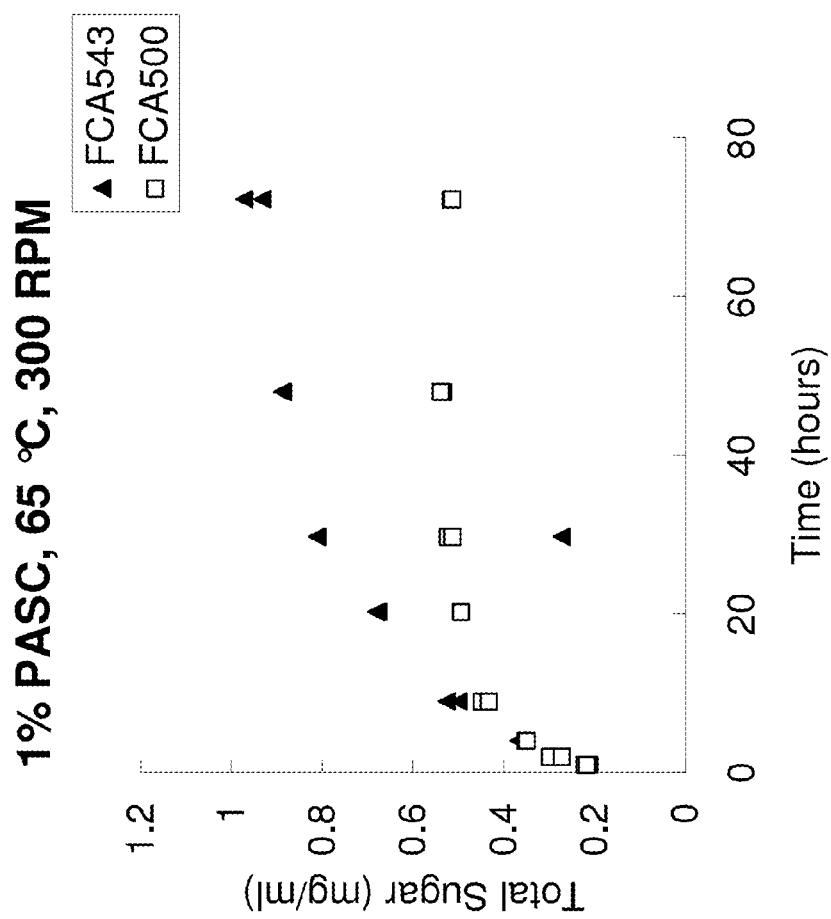
FIG. 13 is a graph of a time course experiment. Total sugar released from PASC by a CBH2 molecule over time at 65° C. is shown. Variant is shown as filled triangles (▲); wild-type as open squares (□).
Figure 14:
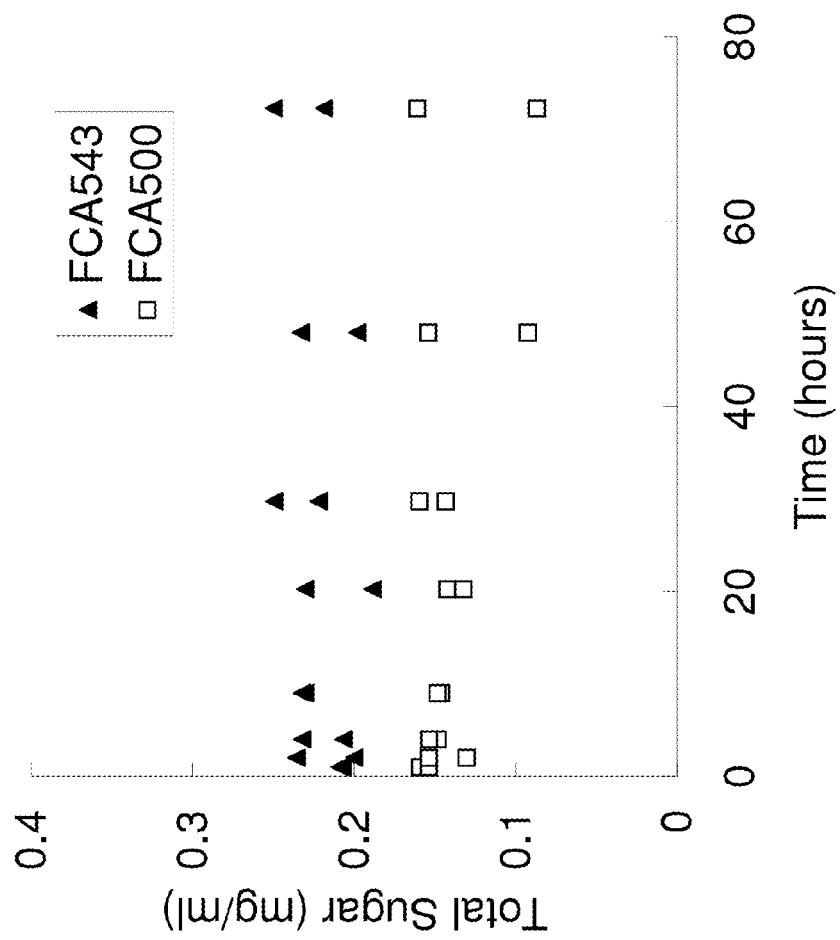
FIG. 14 is a graph of a time course experiment. Total sugar released from PASC by a CBH2 molecule over time at 75° C. is shown. Variant is shown as filled triangles (▲); wild-type as open squares (□).

At 53° C. the variant possessed approximately the same activity as wild-type enzyme over time (see FIG. 12). Due to the stability of the enzymes at 53 C the half-lives of the enzymes could not be determined from the data. At 65° C., the total sugar produced by FCA543 and FCA500 shows that FCA543 is active for a longer period of time than FCA500 (FIG. 13). The half-life of the variant was determined to be approximately 24 hours whereas the wild-type half-life was approximately 4 hours. However, both enzymes begin to fail within the 72-hour incubation time. At 75° C., FCA543 produces more sugar than FCA500 in the first hour (see FIG. 14).

Example 13

CBH2 Variant Specific Activity with Other Cellulases

This example demonstrates the use of the variant (i.e., stabilized) CBH2 in biomass conversion in combination with other cellulases.

A three enzyme mixture with *Acidothermus cellulolyticus* E1 core (see WO 05/093050) plus either wild-type CBH1 and 2 (FCA301 and FCA500, respectively) or stabilized CBH1 and 2 (FCA469 and FCA543, respectively) was tested at both 5 mg/g cellulose and 10 mg/g cellulose and at 38, 53 and 65° C. in the standard conversion assay using PCS as a substrate (see Example 11). Samples were quenched at one, two and five days.

CBH1 variants are described in US Patent Publication No. 20050054039, herein incorporated by reference. The E1 enzyme from *Acidothermus cellulolyticus* is disclosed in U.S. Pat. No. 5,712,142. Reference is also made to the following patent documents WO 91/05039; WO 93/15186; U.S. Pat. No. 5,275,944; WO 96/02551; U.S. Pat. No. 5,536,655 and WO 00/70031. Also reference is made to GenBank U33212.

Figure 15:
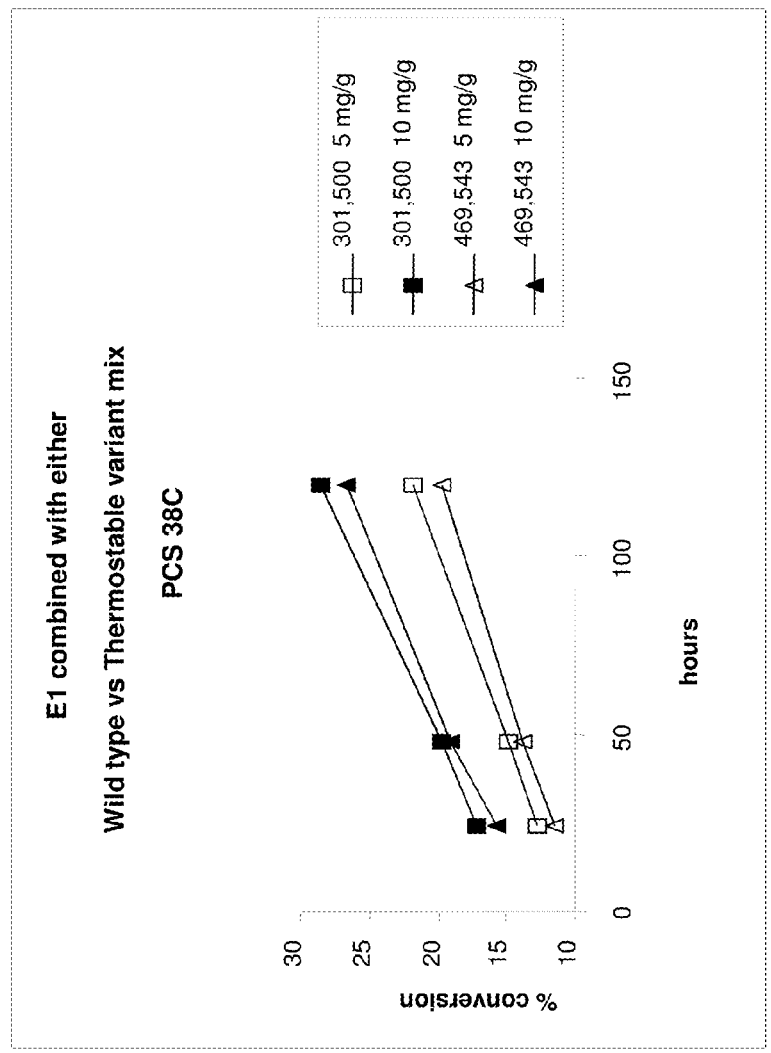
FIG. 15 is a graph depicting the specific performance of a cellulase mixture at 38° C. The mixture contains the *Acidothermus cellulolyticus* E1 catalytic core and either wild-type or variant cellobiohydrolases. The wild-type is designated as 301, 500 which indicates that the wild-type CBH1 (i.e., 301) and wild-type CBH2 (i.e., 500) were used. The variant is designated as 469, 543 which indicates that the variant CBH1 (i.e., 469) and variant CBH2 (i.e., 543) were used.

The results show that the specific performance of the variant mix is about the same as that of the wild type mix at 38° C. (See FIG. 15) A similar pattern for performance is seen at 53° C. (data not shown).

Figure 16:
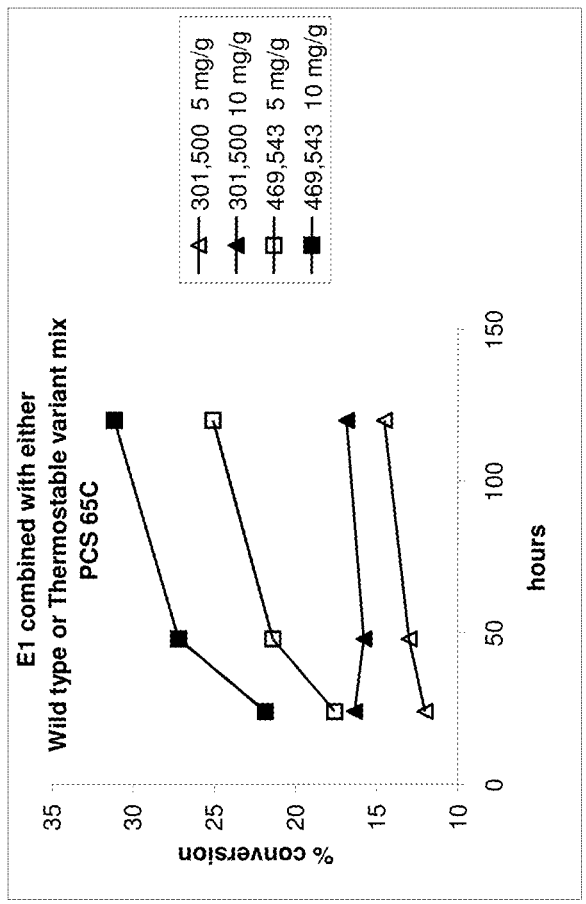
FIG. 16 is a graph depicting the specific performance of a cellulase mixture at 65° C. The mixture contains the *Acidothermus cellulolyticus* E1 catalytic core and either wild-type or variant cellobiohydrolases. The wild-type is designated as 301, 500 which indicates that the wild-type CBH1 (i.e., 301) and wild-type CBH2 (i.e., 500) were used. The variant is designated as 469, 543 which indicates that the variant CBH1 (i.e., 469) and variant CBH2 (i.e., 543) were used.

The stabilized variant mix shows a significant increase in specific performance over the wild type mix at 65° C. (See FIG. 16)

Figure 17:
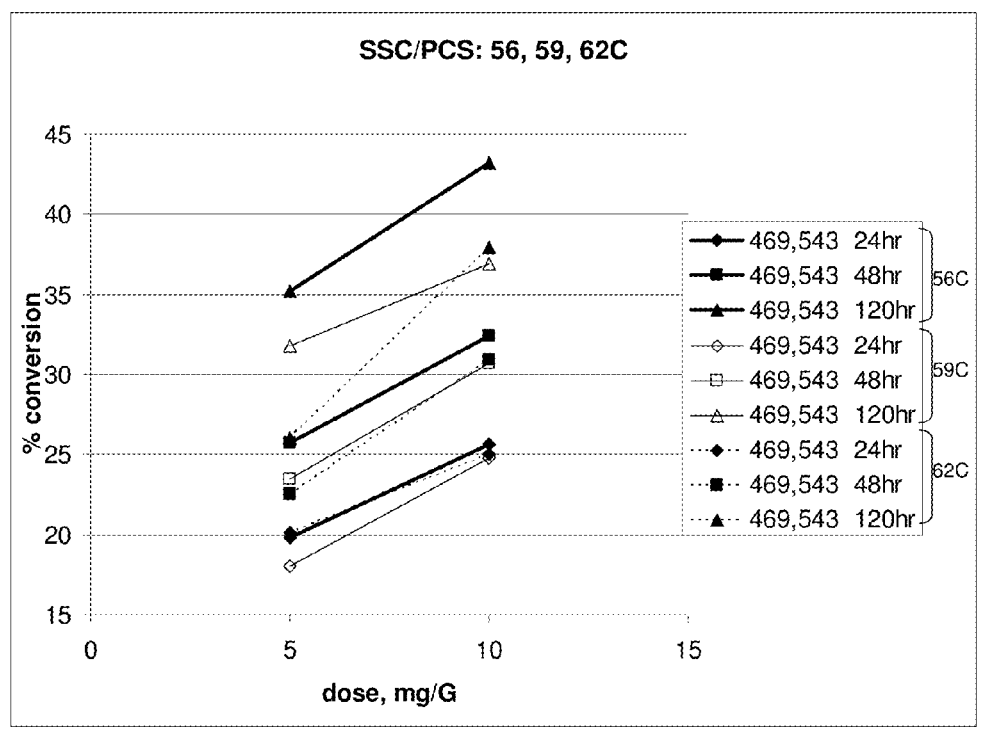
FIG. 17 is a graph of small scale saccharification conversion assay results at varying temperatures of the variant cellulase mixture described above in FIG. 16.

Using the same standard conversion assay as described in Example 11 the specific performance of the stabilized variant mix was tested at 56, 59 and 62° C. at 5 and 10 mg/g cellulose and samples quenched at 24, 48 and 120 hours. At all three times 56° C. was better than the higher temperatures. See FIG. 17. The optimum temperature is below 59° C. at all times tested.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

---

What is claimed:

1. An isolated nucleic acid sequence encoding a variant of a CBH2 cellulase comprising SEQ ID NO:2 or SEQ ID NO:95, wherein the variant consists one or more substitutions as compared to SEQ ID NO:2 or SEQ ID NO:95, respectively, wherein said one or more substitutions are selected, in the context of SEQ ID NO:95, from the group consisting of: V94E, P98L, G118P, M120L, M134(G/L/V), T142V, L144 (G/R/S), M145L, T148Y, T154A, L179A, Q204E, V206L, S210(L/R), I212V, T214(M/Y), L215I, G231N, T232V, V250I, Q276L, N285Q, S291G, G308A, T312S, S316P, V323(L/N/Y), N325D, I333L, G334A, S343P, T349L, G360R, S380T, A381T, S386P, F411Y, S413Y, A416G, Q426E and A429T.

2. The nucleic acid sequence of claim 1, wherein the variant of the CBH2 cellulase consists, in the context of SEQ ID NO:95, the substitution S316P and optionally one or more further substitutions selected from the group consisting of:
   i. I212V/F411Y;
   ii. M134G/L144G;
   iii. M134L/L144R;
   iv. M134L/L144S;
   v. M134V/V206L/I212V/T312S/F411Y/S413Y;
   vi. P98L/M134L/L144R/S210L/T214Y/V323Y/S413Y;
   vii. P98L/M134L/L144R/S210R/T214Y/V323Y/S413Y;
   viii. P98L/M134L/L144R/S413Y;
   ix. P98L/M134L/L144R/V323Y/S413Y;
   x. P98L/M134L/L144R/V206L/S210R/T214Y/S413Y;
   xi. P98L/M134L/L144R/V206L/S210R/T214Y/V323Y/S413Y;
   xii. P98L/M134V/I212V/S413Y;
   xiii. P98L/M134V/I212V/T312S/S413Y;
   xiv. P98L/M134V;
   xv. P98L/M134V/S413Y;
   xvi. P98L/M134V/V323Y/S413Y;
   xvii. P98L/M134V/T154A/I212V/F411Y/S413Y;
   xviii. P98L/M134V/T154A/I212V/S413Y;
   xix. P98L/M134V/T154A/I212V/T312S/S413Y;
   xx. P98L/M134V/T154A/V206L/I212V/F411Y/S413Y;
   xxi. P98L/M134V/T154A/V206L;
   xxii. P98L/M134V/V206L/I212V/F411Y;
   xxiii. P98L/M134V/V206L/I212V/T312S/S413Y;
   xxiv. P98L/M134V/V206L/S210R/T214Y/S413Y;
   xxv. P98L/M134V/V206L/S210R/T214Y/V323Y/S413Y;
   xxvi. P98L/M134V/V206L/S413Y;

xxvii. P98L/V206L/I212V/T312S/F411Y/S413Y;
xxviii. S413Y;
xxix. V323L;
xxx. V323Y;
xxxi. V206L/I212V;
xxxii. V206L/I212V/T312S;
xxxiii. V206L/I212V/T312S/F411Y/S413Y;
xxxiv. V206L/I212V/T312S/S413Y;
xxxv. V206L/S210L/T214M;
xxxvi. V206L/S210R;
xxxvii. V206L/S210R/T214Y; and
xxxviii. V206L.

3. The nucleic acid sequence of claim 1, wherein the CBH2 cellulase variant comprises the substitutions I212V/S316P/F411Y.

4. The nucleic acid sequence of claim 1, wherein the CBH2 cellulase variant comprises the substitutions M134G/L144G/S316P.

5. The nucleic acid sequence of claim 1, wherein the CBH2 cellulase variant comprises the substitutions M134L/L144R/S316P.

6. The nucleic acid sequence of claim 1, wherein the CBH2 cellulase variant comprises the substitutions M134L/L144S/S316P.

7. The nucleic acid sequence of claim 1, wherein the CBH2 cellulase variant comprises the substitutions M134V/V206L/I212V/T312S/S316P/F411Y/S413Y.

8. The nucleic acid sequence of claim 1, wherein the CBH2 cellulase variant comprises the substitutions P98L/M134L/L144R/S210L/T214Y/S316P/V323Y/S413Y.

9. The nucleic acid sequence of claim 1, wherein the CBH2 cellulase variant comprises the substitutions P98L/M134L/L144R/S210R/T214Y/S316P/V323Y/S413Y.

10. The nucleic acid sequence of claim 1, wherein the CBH2 cellulase variant comprises the substitutions P98L/M134L/L144R/S316P/S413Y.

11. The nucleic acid sequence of claim 1, wherein the CBH2 cellulase variant comprises the substitutions P98L/M134L/L144R/S316P/V323Y/S413Y.

12. The nucleic acid sequence of claim 1, wherein the CBH2 cellulase variant comprises the substitutions P98L/M134L/L144R/V206L/S210R/T214Y/S316P/S413Y.

13. The nucleic acid sequence of claim 1, wherein the CBH2 cellulase variant comprises the substitutions P98L/M134L/L144R/V206L/S210R/T214Y/S316P/V323Y/S413Y.

14. The nucleic acid sequence of claim 1, wherein the CBH2 cellulase variant comprises the substitutions P98L/M134V/I212V/S316P/S413Y.

15. The nucleic acid sequence of claim 1, wherein the CBH2 cellulase variant comprises the substitutions P98L/M134V/I212V/T312S/S316P/S413Y.

16. The nucleic acid sequence of claim 1, wherein the CBH2 cellulase variant comprises the substitutions P98L/M134V/S316P.

17. The nucleic acid sequence of claim 1, wherein the CBH2 cellulase variant comprises the substitutions P98L/M134V/S316P/S413Y.

18. The nucleic acid sequence of claim 1, wherein the CBH2 cellulase variant comprises the substitutions P98L/M134V/S316P/V323Y/S413Y.

19. The nucleic acid sequence of claim 1, wherein the CBH2 cellulase variant comprises the substitutions P98L/M134V/T154A/I212V/S316P/F411Y/S413Y.

20. The nucleic acid sequence of claim 1, wherein the CBH2 cellulase variant comprises the substitutions P98L/M134V/T154A/I212V/S316P/S413Y.

21. The nucleic acid sequence of claim 1, wherein the CBH2 cellulase variant comprises the substitutions P98L/M134V/T154A/I212V/T312S/S316P/S413Y.

22. The nucleic acid sequence of claim 1, wherein the CBH2 cellulase variant comprises the substitutions P98L/M134V/T154A/V206L/I212V/S316P/F411Y/S413Y.

23. The nucleic acid sequence of claim 1, wherein the CBH2 cellulase variant comprises the substitutions P98L/M134V/T154A/V206L/S316P.

24. The nucleic acid sequence of claim 1, wherein the CBH2 cellulase variant comprises the substitutions P98L/M134V/V206L/I212V/S316P/F411Y.

25. The nucleic acid sequence of claim 1, wherein the CBH2 cellulase variant comprises the substitutions P98L/M134V/V206L/I212V/T312S/S316P/S413Y.

26. The nucleic acid sequence of claim 1, wherein the CBH2 cellulase variant comprises the substitutions P98L/M134V/V206L/S210R/T214Y/S316P/S413Y.

27. The nucleic acid sequence of claim 1, wherein the CBH2 cellulase variant comprises the substitutions P98L/M134V/V206L/S210R/T214Y/S316P/V323Y/S413Y.

28. The nucleic acid sequence of claim 1, wherein the CBH2 cellulase variant comprises the substitutions P98L/M134V/V206L/S316P/S413Y.

29. The nucleic acid sequence of claim 1, wherein the CBH2 cellulase variant comprises the substitutions P98L/V206L/I212V/T312S/S316P/F411Y/S413Y.

30. The nucleic acid sequence of claim 1, wherein the CBH2 cellulase variant comprises the substitutions S316P/S413Y.

31. The nucleic acid sequence of claim 1, wherein the CBH2 cellulase variant comprises the substitutions S316P/V323L.

32. The nucleic acid sequence of claim 1, wherein the CBH2 cellulase variant comprises the substitutions S316P/V323Y.

33. The nucleic acid sequence of claim 1, wherein the CBH2 cellulase variant comprises the substitutions V206L/I212V/S316P.

34. The nucleic acid sequence of claim 1, wherein the CBH2 cellulase variant comprises the substitutions V206L/I212V/T312S/S316P.

35. The nucleic acid sequence of claim 1, wherein the CBH2 cellulase variant comprises the substitutions 206L/I212V/T312S/S316P/F411Y/S413Y.

36. The nucleic acid sequence of claim 1, wherein the CBH2 cellulase variant comprises the substitutions V206L/I212V/T312S/S316P/S413Y.

37. The nucleic acid sequence of claim 1, wherein the CBH2 cellulase variant comprises the substitutions V206L/S210L/T214M/S316P.

38. The nucleic acid sequence of claim 1, wherein the CBH2 cellulase variant comprises the substitutions V206L/S210R/S316P.

39. The nucleic acid sequence of claim 1, wherein the CBH2 cellulase variant comprises the substitutions V206L/S210R/T214Y/S316P.

40. The nucleic acid sequence of claim 1, wherein the CBH2 cellulase variant comprises the substitutions V206L/S316P.

41. A vector comprising the nucleic acid sequence of claim 1.

42. An isolated host cell transformed with the vector of claim 41.

43. A method of producing a CBH2 variant comprising the steps of:

(a) culturing the host cell according to claim 42 in a suitable culture medium under suitable conditions to produce CBH2 variant;
(b) obtaining said produced CBH2 variant.

* * * * *